US012234255B2

(12) United States Patent
Montgomery et al.

(10) Patent No.: US 12,234,255 B2
(45) Date of Patent: Feb. 25, 2025

(54) METHODS FOR GLYCOSYLATION

(71) Applicant: THE REGENTS OF THE UNIVERSITY OF MICHIGAN, Ann Arbor, MI (US)

(72) Inventors: John Montgomery, Ann Arbor, MI (US); Girish Chandra Sati, Ann Arbor, MI (US); Joshua Lane Martin, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 644 days.

(21) Appl. No.: 17/610,996

(22) PCT Filed: May 14, 2020

(86) PCT No.: PCT/US2020/032793
§ 371 (c)(1),
(2) Date: Nov. 12, 2021

(87) PCT Pub. No.: WO2020/232194
PCT Pub. Date: Nov. 19, 2020

(65) Prior Publication Data
US 2022/0267362 A1    Aug. 25, 2022

Related U.S. Application Data

(60) Provisional application No. 62/847,587, filed on May 14, 2019.

(51) Int. Cl.
| C07H 1/00 | (2006.01) |
| C07F 7/18 | (2006.01) |
| C07H 15/10 | (2006.01) |
| C07H 15/18 | (2006.01) |
| C07H 15/203 | (2006.01) |

(52) U.S. Cl.
CPC ............. *C07H 1/00* (2013.01); *C07F 7/1804* (2013.01); *C07H 15/10* (2013.01); *C07H 15/18* (2013.01); *C07H 15/203* (2013.01)

(58) Field of Classification Search
None
See application file for complete search history.

(56) References Cited

U.S. PATENT DOCUMENTS

| 2006/0051812 A1 | 3/2006 | Helin et al. |
| 2019/0055253 A1 | 2/2019 | Clarke et al. |

OTHER PUBLICATIONS

Nippon Kagaku Kaishi (10), 2040-7; 1985. (Year: 1985).*
Mishra, J. Org. Chem. 2018, 83, 4204-4212. (Year: 2018).*
Christensen, Carbohydrate Research 408 (2015) 51-95. (Year: 2015).*
International Search Report and Written Opinion, Corresponding International Application No. PCT/US2020/032792, mailing date Sep. 17, 2020.
Pubchem, Substance Record for SID 230964669, Feb. 12, 2015. <https://pubchem.ncbi.nlm.nih.gove/substance/230964669>.
Kim et al., Rare earth perchlorate catalyzed glycosidation of glycosyl fluorides with trimethylsilyl ethers, Tetrahedron Lett., 36(25):4443-4446(1995).
Kong et al., Synthesis of substituted 2,7-dioxabicyclo[4.1.0]heptanes: 1,2-anhydro-3,4,6-tri-O-benzyl- and 1,2-anhydro-3,4,6-tri-O-(p-bromobenzyl)-a-d-galactopyranose, Carbohydrate Research, 162(2):217-225(1987).
Konradsson et al., Iodonium ion generated in situ from N-iodosuccinimide and trifluoromethanesulphonic acid promotes direct linkage of 'disarmed' pent-4-enyl glycosides, Journal of the Chemical Society, Chemical Communications, (3):270-272(1990).
Koto et al., Synthesis of O-ß-d-Glucopyranosyl-(1?2)-O-ß-d-glucopyranosyl-(1?6)-d-glucopyranose; Dehydrative ß-d-Glucosylation Using 2-O-Acetyl-3,4,6-tri-O-benzyl-d-glucopyranose, Bulletin of the Chemical Society of Japan, 58 (1):120-122(1985).
Koto et al., The Synthesis of Methyl 2,4,6-Tri-O-benzyl-a-D-glucopyranoside, Bull. Chem. Soc. Jpn., 45(1):291-293 (1972).
Kova et al., The Reaction of 2,3,4-Thi-O-Bknzyl-D-Glucose with Diethylaminosulfur Trifluoride (Dast), Journal of Carbohydrate Chemistry , 6(3):423-439(1987).
Krasnova et al., Oligosaccharide Synthesis and Translational Innovation, J. Am. Chem. Soc, 141(9): 3735-3754 (2019).
Kulkarni et al., "One-Pot" Protection, Glycosylation, and Protection-Glycosylation Strategies of Carbohydrates, Chem. Rev, 118(1): 8025-8104(2018).
Kumar et al., Introducing Oxo-Phenylacetyl (OPAc) as a Protecting Group for Carbohydrates, J. Org. Chem., 84 (7):4131-4148(2019).
Kunz et al., Stereoselective Glycosylation of Alcohols and Silyl Ethers Using Glycosyl Fluorides and Boron-Trifluoride Etherate, Helv. Chim. Acta, 68(1): 283-287(1985).
Lee et al., Stereoselective Synthesis of ?eta-L-Rhamnopyranosides, J. Am. Chem. Soc, 130(1): 6330-6331(2008).
Levi et al., Catalytic Activation of Glycosyl Phosphates for Stereoselective Coupling Reactions, Proc. Natl. Acad. Sci, 116(1): 35-39(2019).
Levin et al., A Catalytic Fluoride-Rebound Mechanism for C(sp3)-CF3 Bond Formation, Science, 356(1): 1272-1275 (2017).
Ley et al., A Facile One-Pot Synthesis of a Trisaccharide Unit from the Common Polysaccharide Antigen of Group-B Streptococci Using Cyclohexane-1,2-Diacetal (Cda) Protected Rhamnosides, Angew. Chem. Int, 33(1): 2292-2294 (1994).
Lin et al., Long-Range Corrected Hybrid Density Functionals with Improved Dispersion Corrections, J. Chem. Theory Comput., 9(1):263-272(2013).
Love et al., Automated Solid-Phase Synthesis of Protected Tumor-Associated Antigen and Blood Group Determinant Oligosaccharides, Angewandte Chemie International Edition, 43(5):602-605(2004).

(Continued)

*Primary Examiner* — Layla D Berry
(74) *Attorney, Agent, or Firm* — MARSHALL, GERSTEIN & BORUN LLP

(57) ABSTRACT

Provided herein are methods of glycosylation in the formation of disaccharides, trisaccharides, and oligosaccharides using fluoroglycosides, silyl ether glycosides and a triaryl borane catalyst.

22 Claims, 3 Drawing Sheets

(56) References Cited

OTHER PUBLICATIONS

Mallick et al., AuIII-Halide/Phenylacetylene-Catalysed Glycosylations Using 1-O-Acety••furanoses and Pyranose 1,2-Orth••esters as Glycosyl Donors, Eur. J. Org. Chem, 2016(3):579-588(2016).

Manabe et al., Hafnium(IV) Tetratriflate as a Glycosyl Fluoride Activation Reagent, The Journal of Organic Chemistry, 78(9):4568-4572(2013).

Marenich et al., Self-Consistent Reaction Field Model for Aqueous and Nonaqueous Solutions Based on Accurate Polarized Partial Charges, J. Chem. Theory Comput, 3(6):2011-2033(2007).

Micheli et al., A new approach to the synthesis of ß-glycosidically linked oligosaccharides containing 2-acetamido-2-deoxy-d-mannose residues, Carbohydrate Research, 139:C1-C3(1985).

Mootoo et al., Armed and Disarmed N-Pentenyl Glycosides in Saccharide Couplings Leading to Oligosaccharides, J. Am. Chem. Soc, 110(1): 5583-5584(1988).

Mugunthan et al., A facile and convenient synthesis of disarmed glycosyl fluorides using in situ-generated iodine monofluoride (see Ref. 1, 38, 39, 40, 41, 42, 43), Tetrahedron Letters, 53(42):5631-5634(2012).

Mukaiyama et al., A Highly Stereoselective Synthesis of a-Glucosides from 1-O-Acetyl Glucose by Use of Tin(IV) Chloride—Silver Perchlorate Catalyst System, Chem. Lett., 20(4):533-536(1991).

Mukhopadhyay et al., From Solution Phase to "On-Column" Chemistry: Trichloroacetimidate-Based Glycosylation Promoted by Perchloric Acid-Silica, The Journal of Organic Chemistry, 70(222):9059-9062(2005).

Myers et al., BF3•OEt2 and TMSOTf: A synergistic combination of Lewis acids, Chem. Commun., 42:4434-4436 (2006).

Neese F., The ORCA program system, WIREs Comput. Mol. Sci., 2(1):73-78(2012).

Nguyen, Synthesizing mothers' milk: Scientists are seeking ways to make benefical but elusive sugars found in breast milk, Biocatalysis, 96(27):1-7(Jul. 2018).

Nicolaou et al., Reactions of Glycosyl Fluorides—Synthesis of O-Glycosides, S-Glycosides, and N-Glycosides, J. Chem. Soc.-Chem. Commun, 1155-1156(1984).

Nielsen et al., Catalytic Glycosylations in Oligosaccharide Synthesis, Chem. Rev, 118(1): 8285-8358(2018).

Nielsen et al., Vessel Effect in C-F Bond Activation Prompts Revised Mechanism and Reveals an Autocatalytic Glycosylation, Eur. J. Org. Chem, 140-144(2019).

Nishi et al., Stereospecific ?eta-L-Rhamnopyranosylation through an SNI-Type Mechanism by Using Organoboron Reagents, Angew. Chem. Int, 57(1): 13858-13862(2018).

Padungros et al., Glycosyl Dithiocarbamates: ß-Selective Couplings without Auxiliary Groups, The Journal of Organic Chemistry, 79(6):2611-2624(2014).

Palomino et al., Synthesis of the Trisaccharide a-l-Rha-(1-2)-a-l-Rha-(1-2)-a-L-Rha with a Dioxolane-Type Spacer-Arm1, J. Carbohydr., 15(2):137-146(1996).

Panza et al., Automated Chemical Oligosaccharide Synthesis: Novel Approach to Traditional Challenges, Chem. Rev, 118(17): 8105-8150(2018).

Park et al., Macrocyclic Bis-Thioureas Catalyze Stereospecific Glycosylation Reactions, Science, 355(6321): 162-166 (2017).

Partridge et al., A Streamlined Strategy for Aglycone Assembly and Glycosylation, Angew. Chem. Int, 52(51): 13647-13650(2013).

Piers et al., Mechanistic Aspects of Bond Activation with Perfluoroarylboranes, Inorg. Chem, 50(1): 12252-12262 (2011).

Plante et al., Automated Solid-Phase Synthesis of Oligosaccharides, Science, 291(5508):1523-1527(2001).

Prudden et al., Synthesis of Asymmetrical Multiantennary Human Milk Oligosaccharides, Proc. Natl. Acad. Sci, 114(1): 6954-6959(2017).

Raghavan et al., One-Step Synthesis of the Ciclamycin Trisaccharide, J. Am. Chem. Soc, 115(1): 1580-1581(1993).

Ravida et al., Synthesis of Glycosyl Phosphates from 1,2-Orthoesters and Application to in Situ Glycosylation Reactions, Organic Letters, 8(9):1815-1818(2006).

Sati et al., Fluoride Migration Catalysis Enables Simple, Stereoselective, and Iterative Glycosylation, J. Am. Chem. Soc., 142(15):7235-7242(2020).

Schmidt, New Methods for the Synthesis of Glycosides and Oligosaccharides—Are There Alternatives to the Koenigs-Knorr Method, Angew. Chem. Int, 25(1): 212-235(1986).

Schofield et al., Synthetic GPI as a candidate anti-toxic vaccine in a model of malaria, Nature, 418:785-789(2002).

Seeberger, The Logic of Automated Glycan Assembly, Acc. Chem. Res, 48(1): 1450-1463(2015).

Shao et al., Advances in molecular quantum chemistry contained in the Q-Chem 4 program package, Mol. Phys., 113 (2): 184-215(2015).

Shi et al., C2-Acyloxyglycosylation with Glycal Donors, J. Am. Chem. Soc., 123(28):6939-6940(2001).

Shimizu et al., Chemistry of Glycosyl Fluorides, Synthesis, 799-822(1998).

Shu et al., Interrupted Pummerer Reaction in Latent-Active Glycosylation: Glycosyl Donors with a Recyclable and Regenerative Leaving Group, J. Angew. Chem., Int. Ed. Engl., 54(48):14432-14436(2015).

Singh et al., Achiral 2-Hydroxy Protecting Group for the Stereocontrolled Synthesis of 1,2-cis-a-Glycosides by Six-Ring Neighboring Group Participation, J. Org. Lett., 17(17):4376-4379 (2015).

Stephan D. W., The Broadening Reach of Frustrated Lewis Pair Chemistry, Science, 354(1248): (2016).

Stork et al., Stereocontrolled synthesis of disaccharides via the temporary silicon connection, Journal of the American Chemical Society, 114(3):1087-1088(1992).

Stork et al., Stereoselective Synthesis of ß-Mannopyranosides via the Temporary Silicon Connection Method, J. Am. Chem. Soc., 118(1):247-248(1996).

Tang et al., Automated Fluorous-Assisted Solution-Phase Synthesis of ?-1,2-, 1,3-, and 1,6-Mannan Oligomers, Carbohydr. Res, 430(1): 8-15(2016).

Tang et al., Automated Solution-Phase Synthesis of ß-1,4-Mannuronate and ß-1,4-Mannan, Organic Letters, 17 (11):2642-2645(2015).

Trumtel et al., The synthesis of 2'-deoxy-ß-disaccharides: Novel approaches, Carbohydr. Res., 191(1):29-52(1989).

Vic et al., Glycosidase-catalysed synthesis of glycosides by an improved procedure for reverse hydrolysis: application to the chemoenzymatic synthesis of galactopyranosyl-(1->4)-O-a-galactopyranoside derivatives, Tetrahedron: Asymmetry, 7(7):1973-1984(1996).

Vidadala et al., Orthogonal Activation of Propargyl and n-Pentenyl Glycosides and 1,2-Orthoesters, J. Org. Chem., 74 (23):9233-9236(2009).

Wadzinski et al., Rapid Phenolic O-Glycosylation of Small Molecules and Complex Unprotected Peptides in Aqueous Solvent, Nat. Chem, 10(6): 644-652(2018).

Walk J. T., Sugar Silanes: Versatile Reagents for Stereocontrolled Glycosylation via Intramolecular Aglycone Delivery, Chem. Sci, 6(1): 3448-3453(2015).

Wang et al., Regioselective one-pot protection of carbohydrates, Nature, 446:896-899(2007).

Wang et al., Regioselective one-pot protection of glucose, Nat. Protoc., 3(1):97-113(2008).

Wen et al., Blue Light Photocatalytic Glycosylation without Electrophilic Additives, Organic Letters, 19(9):2402-2405 (2017).

Wen et al., Toward Automated Enzymatic Synthesis of Oligosaccharides, Chem. Rev, 118(1): 8151-8187(2018).

Xiao et al., Remote Activation of Disarmed Thioglycosides in Latent-Active Glycosylation via Interrupted Pummerer Reaction, J. Am. Chem. Soc., 138(40):13402-13407(2016).

Yang et al., Stereoselective Oxidative Glycosylation of Anomeric Nucleophiles with Alcohols and Carboxylic Acids, Nat. Commun, 9(3650): (2018).

Yu et al., Phenanthroline-Catalyzed Stereoretentive Glycosylations, Angew. Chem. Int, 58(1): 6957-6961(2019).

Zhang et al., Programmable One-Pot Oligosaccharide Synthesis, J. Am. Chem. Soc, 121(1): 734-753(1999).

(56) References Cited

OTHER PUBLICATIONS

Zhou et al., Matching Glycosyl Donor Reactivity to Sulfonate Leaving Group Ability Permits SN2 Glycosylations, J. Am. Chem. Soc, 141(42): 16743-16754(2019).

Zhu et al., A Two Directional Glycosylation Strategy for the Convergent Assembly of Oligosaccharides, Tetrahedron Lett, 39(1): 2187-2190(1998).

Zimmerman P. M., Automated discovery of chemically reasonable elementary reaction steps, J. Comput. Chem., 34 (16): 1385-1392(2013).

Zimmerman P. M., Growing string method with interpolation and optimization in internal coordinates: Method and examples, J. Chem. Phys., 138(18):184102(2013).

Zimmerman P. M., Navigating molecular space for reaction mechanisms: an efficient, automated procedure, Mol. Simulat., 41(1-3):43-54(2015).

Zimmerman P. M., Single-Ended Transition State Finding with the Growing String Method, J. Comput. Chem, 36(1): 601-611(2015).

Zimmerman P., Reliable Transition State Searches Integrated with the Growing String Method, J. Chem. Theory Comput., 9(7):3043-3050(2013).

Adero et al., The Experimental Evidence in Support of Glycosylation Mechanisms at the SN1-SN2 Interface, Chem. Rev, 118(17): 8242-8284(2018)., Aug. 19, 2024.

Adhikari et al., Studies of S-But-3-ynyl and gem-Dimethyl S-But-3-ynyl Thioglycoside Donors in Gold-Catalyzed Glycosylations, Journal of Carbohydrate Chemistry, 32(5-6):336-359(2013).

Agre et al., Training the Next Generation of Biomedical Investigators in Glycosciences, J. Clin. Invest, 126(2): 405-408 (2016).

Akhtar et al., Unusual synthesis of carbohydrate sec-sec ether-linked pseudodisaccharides, Carbohydr. Res., 343 (12), 2094-2100(2008).

Aloui et al., Stereoselective 1,2-cis Glycosylation of 2-O-Allyl Protected Thioglycosides, Chemistry A European Journal, 8(11):2608-2621(2002).

Arbués et al., Trisaccharides of Phenolic Glycolipids Confer Advantages to Pathogenic Mycobacteria through Manipulation of Host-Cell Pattern-Recognition Receptors, ACS Chem. Biol., 11(10):2865-2875(2016).

Backinowsky et al., Reactions of sugar thio-orthoesters: Nucleophilic substitution of an arylthio group during zemplén deacylation, Carbohydr. Res., 98(2):181-193(1981).

Baeschlin et al., Rapid assembly of oligosaccharides: 1,2-diacetal-mediated reactivity tuning in the coupling of glycosyl fluorides, Tetrahedron: Asymmetry 11(1):173-197(2000).

Balmond et al., a-Selective Organocatalytic Synthesis of 2-Deoxygalactosides, Angew. Chem. Int. Ed., 51 (36):9152-9155(2012).

Barresi et al., Synthesis of .beta.-mannopyranosides by intramolecular aglycon delivery, Journal of the American Chemical Society, 113(24):9376-9377(1991).

Barresi et al., The synthesis of ß-mannopyranosides by intramolecular aglycon delivery: scope and limitations of the existing methodology, Canadian Journal of Chemistry, 72(6):1447-1465(1994).

Barrett et al., Reactions of relevance to the chemistry of aminoglycoside antibiotics Part 13. A novel synthesis of benzyl ethers, J. Chem. Soc., Perkin Trans., 2(0):2184-2190(1980).

Bergquist et al., Aqua, Alcohol, and Acetonitrile Adducts of Tris(perfluorophenyl)borane: Evaluation of Brønsted Acidity and Ligand Lability with Experimental and Computational Methods, Journal of the American Chemical Society, 122(43):10581-10590(2000).

Bertozzi et al., Chemical Glycobiology Science, 291(1): 2357-2364(2001).

Blackwell et al., B(C6F5)3-Catalyzed Silation of Alcohols: A Mild, General Method for Synthesis of Silyl Ethers, J. Org. Chem, 64(13): 4887-4892(1999).

Bock et al., A study of 13CH coupling constants in hexopyranoses, J. Chem. Soc., Perkin Trans., 2(3):293-297(1974).

Bock et al., Reaction of Sugar Esters with Hydrogen Fluoride. XIV. Rearrangement of D-Xylose and D-Lyxose Derivatives, Acta Chemica Scandinavica, 30B:727-732(1976).

Bols M., Stereocontrolled Synthesis of Alpha-Glucosides by Intramolecular Glycosidation, J. Chem. Soc. Chem. Commun, 913-914(1992).

Buchan et al., Ketone Hydrosilylation with Sugar Silanes Followed by Intramolecular Aglycone Delivery: An Orthogonal Glycosylation Strategy, Angew. Chem. Int, 48(26): 4840-4844(2009).

Caputo et al., Activation of Alkyl C-F Bonds by B(C6F5)3: Stoichiometric and Catalytic Transformations, Organometallics, 31(1): 27-30(2012).

Chatterjee et al., An Empirical Understanding of the Glycosylation Reaction, J. Am. Chem. Soc, 140(38): 11942-11953 (2018).

Chayajarus et al., Stereospecific Synthesis of 1,2-cis Glycosides by Vinyl-Mediated IAD, Organic Letters, 6 (21):3797-3800(2004).

Chitnis et al., Phosphorus Coordination Chemistry in Catalysis: Air Stable P(III)-Dications as Lewis Acid Catalysts for the Allylation of C-F Bonds, Organometallics, 37(1): 4540-4544(2018).

Crich et al., Direct Formation of Beta-Mannopyranosides and Other Hindered Glycosides from Thioglycosides, J. Am. Chem. Soc, 120(1): 435-436(1998).

Crich et al., Direct Synthesis of the Beta-L-Rhamnopyranosides, Org. Lett, 5(5): 781-784(2003).

Crich et al., Stereocontrolled Synthesis of D- and L-Beta-Rhamnopyranosides with 4-O-6-S-a-Cyanobenzylidene-Protected 6-Thiorhamnopyranosyl Thioglycosides, J. Org. Chem, 74(2): 773-781(2009).

Cumpstey et al., Allyl Protecting Group Mediated Intramolecular Aglycon Delivery (IAD) of Glycosyl Fluorides, Monatsh. Chem., 133(4):449-466(2002).

Cumpstey et al., Stereospecific Synthesis of 1,2-cis Glycosides by Allyl-Mediated Intramolecular Aglycon Delivery. 2. The Use of Glycosyl Fluorides, Organic Letters, 3(15):2371-2374(2001).

Daragics et al., Regio- and chemoselective reductive cleavage of 4,6-O-benzylidene-type acetals of hexopyranosides using BH3. THF—TMSOTf, Tetrahedron Lett., 50(24):2914-2916(2009).

Du et al., MPTGs: Thioglycoside Donors for Acid-Catalyzed O-Glycosylation and Latent-Active Synthetic Strategies, 21(4):980-983(2019).

Dulery et al., a and ßl-Fucopyranosyl oxyamines: key intermediates for the preparation of fucose-containing glycoconjugates by oxime ligation, Carbohydrate Research, 342(7):894-900(2007).

Elie et al., Synthesis of 1-O-(1,2-Di-O-palmitoyl-SN-glycero-3-phosphoryl)-2-O-a-D-mannopyranosyl-D-MYO-inositol: a fragment of mycobacterial phospholipids, Tetrahedron, 45(11):3477-3486(1989).

Fügedi et al., Thioglycosides as Glycosylating Agents in Oligosaccharide Synthesis, Glycoconjugate Journal, 4(1): 97-108(1987).

Glycoscience Retrived from https://commonfund.nih.gov/ Glycoscience (2019).

Goswami et al., Bismuth(V)-Mediated Thioglycoside Activation, Angew. Chem. Int, 52(32): 8441-8445(2013).

Grimme S., Semiempirical GGA-type density functional constructed with a long-range dispersion correction, J. Comput. Chem., 27(15):1787-1799(2006).

Gyöomöre, Moisture-Tolerant Frustrated Lewis Pair Catalyst for Hydrogenation of Aldehydes and Ketones, ACS Catal., 5:5366-5372 (2015).

Hansen et al., Defining the SN1 Side of Glycosylation Reactions: Stereoselectivity of Glycopyranosyl Cations, ACS Cent. Sci, 5(1): 781-788(2019).

Hashimoto et al., Glycosylation Using Glucopyranosyl Fluorides and Silicon-Based Catalysts—Solvent Dependency of the Stereoselection, Tetrahedron Lett, 25(1): 1379-1382(1984).

Hinklin et al., Glycosyl Sulfonylcarbamates: New Glycosyl Donors with Tunable Reactivity, J. Am. Chem. Soc., 123 (14)-3379-3380(2001).

Hoang et al., Programmable Synthesis of 2-Deoxyglycosides, J. Am. Chem. Soc, 141(1): 8098-8103(2019).

Huang et al., Iterative One-Pot Synthesis of Oligosaccharides, Angew. Chem. Int, 43(1): 5221-5224(2004).

(56) References Cited

OTHER PUBLICATIONS

Ikeshita et al., Synthesis of lipooligosaccharide nodulation signals NodBj-V(RCO, MeFuc) and NodBj-IV(RCO, MeFuc) of Bradyrhizobium japonicum, Glycoconj J., 11(3):257-261(1994).

Ishihara et al., Tris(Pentafluorophenyl) Boron as an Efficient, Air-Stable, and Water Tolerant Lewis-Acid Catalyst, Bull. Chem. Soc. Jpn, 68(1): 1721-1730(1995).

Izumi et al., Regio- and Stereoselective Synthesis of 1,2-cis-Glycosides by Anomeric O-Alkylation with Organoboron Catalysis, Organic Letters, 21(3):665-670(2019).

Jayakanthan et al., Glycosyl trichloroacetylcarbamate: a new glycosyl donor for O-glycosylation, Carbohydrate Research, 340(17):2688-2692(2005).

Karimi et al., Mild and Highly Efficient Method for the Silylation of Alcohols Using Hexamethyldisilazane Catalyzed by Iodine under Nearly Neutral Reaction Conditions, The Journal of Organic Chemistry, 65(21):7228-7230(2000).

Karimov et al., Rapid Assembly of the Doubly-Branched Pentasaccharide Domain of the Immunoadjuvant Jujuboside a via Convergent B(C6f5)3-Catalyzed Glycosylation of Sterically-Hindered Precursors, Chem. Commun, 53(43): 5838-5841(2017).

Kiessling et al., Chemistry-Driven Glycoscience, Bioorg. Med. Chem, 26(1): 5229-5238(2018).

Kihlberg et al., Synthetic receptor analogues: preparation of the 3-O-methyl, 3-C-methyl, and 3-deoxy derivatives of methyl 4-O-a-d-galactopyranosyl-ß-d-galactopyranoside (methyl ß-d-galabioside), Carbohydr. Res., 152:113-130 (1986).

\* cited by examiner

METHODS FOR GLYCOSYLATION

CROSS REFERENCE TO RELATED APPLICATIONS

This application is the U.S. National phase of International Patent Application No. PCT/US20/32793 filed May 14, 2020, which in turn claims the priority benefit of U.S. Provisional 62/847,587 filed on May 14, 2019, the respective disclosures of which are hereby incorporated by reference in their entireties.

STATEMENT OF GOVERNMENT SUPPORT

This invention was made with government support under grant number GM125274, awarded by the National Institute of Health (NIH). The government has certain rights in the invention.

BACKGROUND

Synthetic sugars, particularly oligosaccharides, have been elusory for years. Human milk contains a gold mine of health-boosting molecules including the human milk oligosaccharides. These highly complex molecules are only beginning to be synthesized today. Researchers are using various methods from classical synthetic methods to genetically engineered bacteria. Mothers' milk holds a mixture of over 200 oligosaccharides and are constantly changing. Analytical chemists have identified about ¾ of the sugars' structures yet only a fraction of those have actually been synthesized.

SUMMARY

Provided herein are methods of forming a glycoside bond between a fluoroglycoside and a silylether glycoside. More particularly, the disclosed methods comprise admixing at least one fluoroglycoside of formula (I) and a silyl ether glycoside, in the presence of a catalyst having a formula $B(Ar^1)(Ar^2)(Ar^3)$ under conditions sufficient to form a glycoside product:

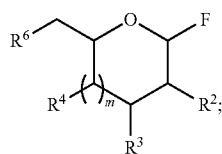
(I)

wherein each of $R^2$, $R^3$, $R^4$, and $R^6$ is independently H, $C_{1-6}$ alkyl, $-N(R^1)_2$, $-N_3$, $CO_2H$, $CO_2C_{1-6}$alkyl, or $-OR^{PG}$, or two of $R^2$, $R^3$, $R^4$, and $R^6$, together with the atoms to which they are attached form a five to eight membered heterocycloalkyl having 1 to 3 ring heteroatoms selected from O, N, and S; each of $Ar^1$, $Ar^2$, $Ar^3$ is independently a halophenyl; each $R^1$ is independently H, $C(O)C_{1-6}$alkyl, or an amino protecting group; each $R^{PG}$ is independently a hydroxyl protecting group or a saccharide; and m is 0 or 1.

In some cases, the silyl ether glycoside has a structure of Formula (II):

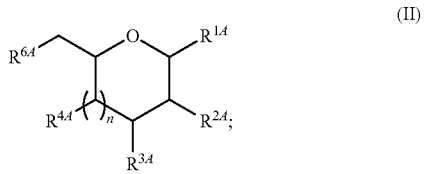
(II)

wherein each of $R^{1A}$, $R^{2A}$, $R^{3A}$, $R^{4A}$, and $R^{6A}$ independently is H, an O-silyl ether, $OR^{PG}$, $CO_2H$, $CO_2C_{1-6}$alkyl, or $C_{1-6}$alkyl, each $R^{PG}$ is independently a hydroxyl protecting group or a saccharide, and n is 0 or 1; with the proviso that at least one of $R^{1A}$, $R^{2A}$, $R^{3A}$, $R^{4A}$, and $R^{6A}$ comprises an O-silyl ether. In some cases, the silyl ether glycoside comprises a structure

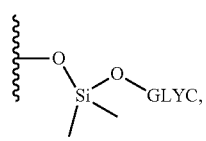

wherein the wavy bond indicates attachment of the silyl ether is to the rest of the glycoside and GLYC is another glycoside moiety. In some cases the GLYC has a structure selected from the group consisting of:

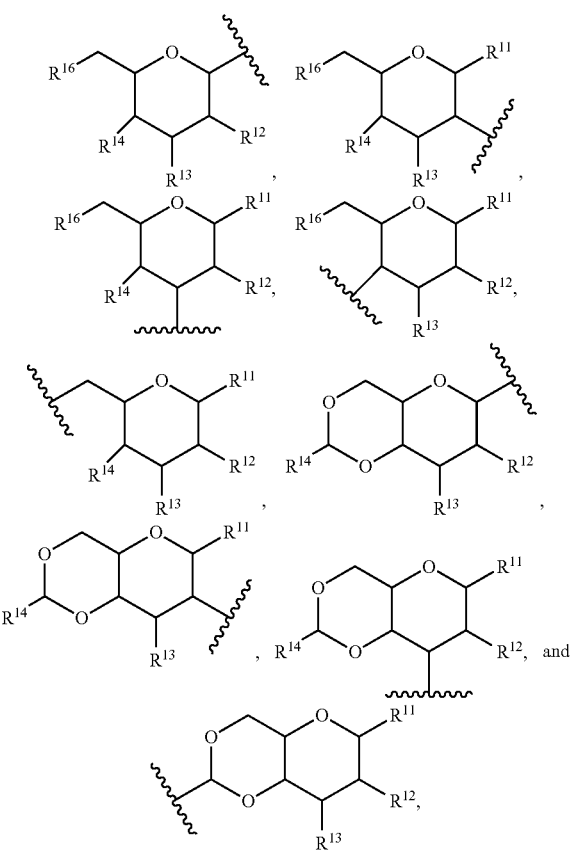

and each of $R^{11}, R^{12}, R^{13}, R^{14}, R^{15}$, and $R^{16}$ is independently H, $-OR^{PG}$, $C_{1-6}$ alkyl, $CO_2H$, $CO_2C_{1-6}$alkyl, $Ar^4$, or $N(R^1)_2$, or two of $R^{11}, R^{12}, R^{13}, R^{14}, R^{15}$, and $R^{16}$, together with the atoms to which they are attached form a five to eight member heterocycloalkyl comprising 1 to 3 ring heteroatoms selected from O, N, and S, and each $Ar^4$ is independently selected from $C_6$-$C_{22}$ aryl or a 5-12 membered heteroaryl comprising from 1 to 3 ring heteroatoms selected from O, N, and S.

DETAILED DESCRIPTION

Figure 1:
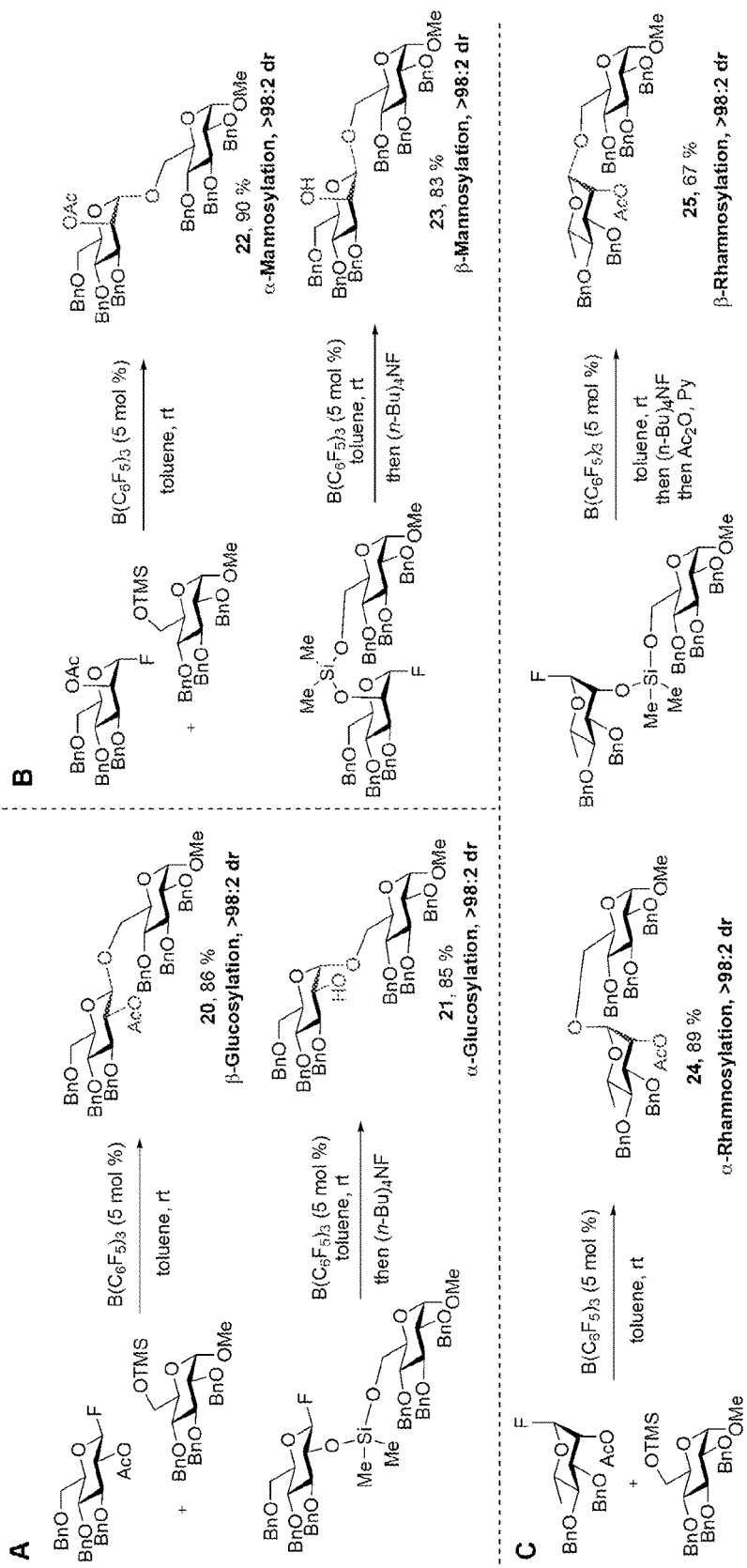
FIG. 1 depicts the evaluation of inter- and intramolecular glycosylations for divergent stereoselectivity using the methods as described herein; A) depicts the stereoselective synthesis of β- and α-glucosides; B) depicts the stereoselective synthesis of α- and β-mannosides; and C) depicts the stereoselective synthesis of α- and β-L-rhamnoside.
Figure 2:
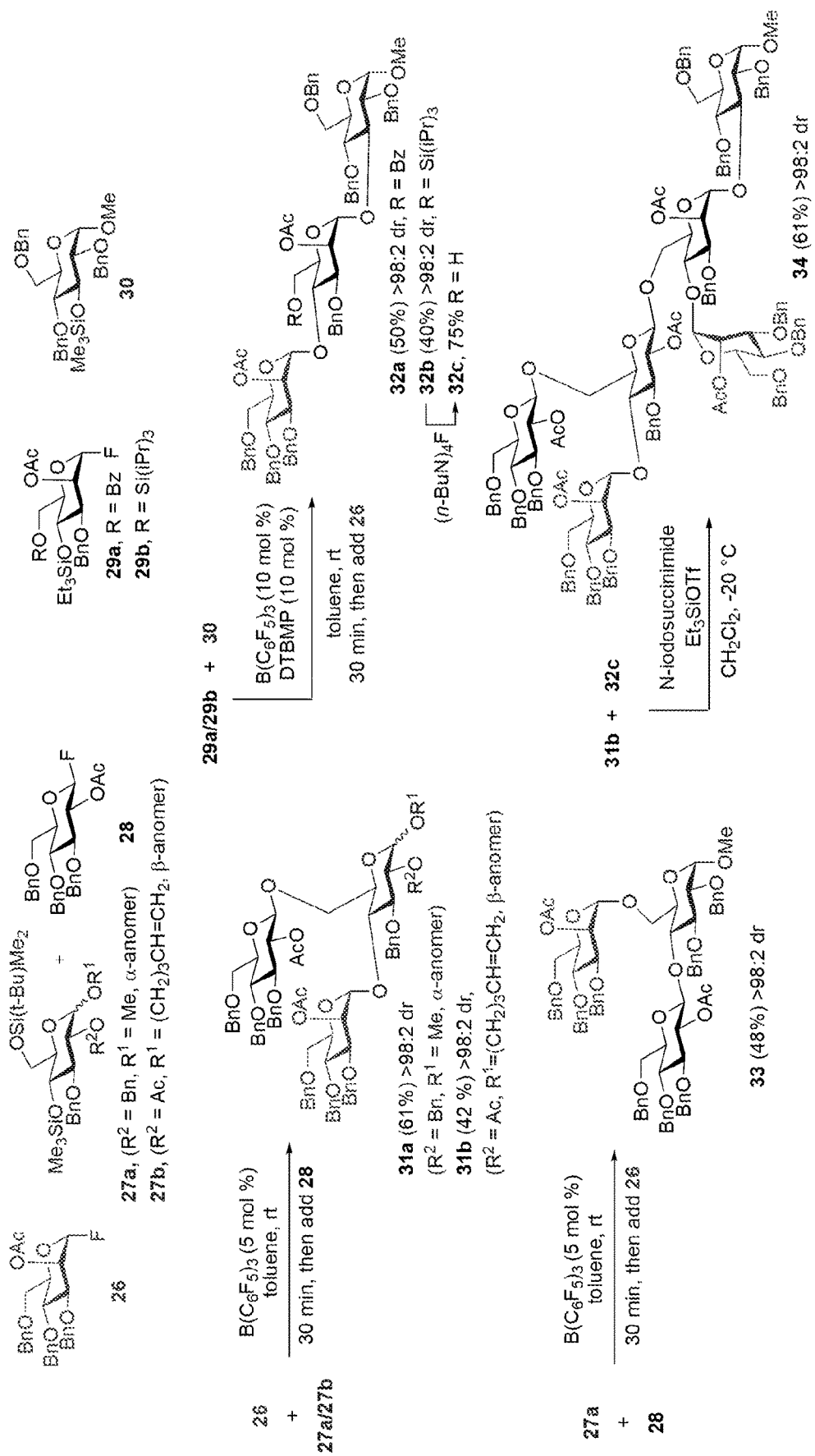
FIG. 2 depicts the iterative assembly of oligosaccharides as described herein, wherein $B(C_6F_5)_3$-catalyzed reactions were conducted using 5 mol % $B(C_6F_5)_3$ in toluene at room temperature. Single diastereomer of products was obtained.

Provided herein are methods for formation of glycosidic bonds. The method comprises coupling of fluoroglycosides and silyl ether glycosides in the presence of a boron catalyst.

Many modifications and other embodiments disclosed herein will come to mind to one skilled in the art to which the disclosed compositions and methods pertain having the benefit of the teachings presented in the foregoing descriptions. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

Methods of Forming Glycoside Products

The disclosure provides methods for glycosylation. The methods can be used for the synthesis of disaccharides, trisaccharides, tetrasaccharides, and oligosaccharides. Saccharides that can be coupled using the disclosed methods include any known or derivatized sugar, that comprises a C-1 fluoro group and one that comprises a O-silyl ether. The saccharide can be a pentose, hexose, heptose, an aminopentose, aminohexose, aminoheptose, or a neuraminic acid. Some contemplated saccharides include, but are not limited to, allose, altrose, glucose, mannose, gulose, idose, galactose, talose, sialic acid, glucosamine, galactosamine, fructose, sorbose, psicose, tagatose, sucrose, lactose, maltose, trehalose, cellobiose, chitobiose, lactulose, kojibiose, nigerose, isomaltose, sophorose, laminaribose, gentiobiose, turanose, matlulose, plaltinose, gentiobiulose, mannobiose, melibiose, melibiulose, rutinose, rutinulose, N-acetylglucosamine, fucose, N-acetylneuraminic acid, sialic acid, and xylobiose. For the avoidance of doubt, the terms "carbohydrate," "sugar," and "saccharide" are all used interchangeably.

In general, the methods disclosed herein comprise admixing at least one fluoroglycoside of formula (I) and a silyl ether glycoside, in the presence of a catalyst having a formula $B(Ar^1)(Ar^2)(Ar^3)$ under conditions sufficient to form a glycoside product:

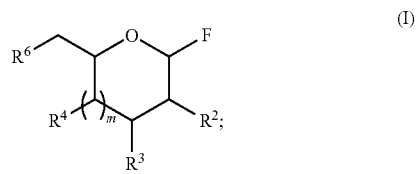

(I)

wherein each of $R^2, R^3, R^4$, and $R^6$ is independently H, $C_{1-6}$ alkyl, $-N(R^1)_2$, $-N_3$, $CO_2H$, $CO_2C_{1-6}$alkyl, or $-OR^{PG}$, or two of $R^2, R^3, R^4$, and $R^6$, together with the atoms to which they are attached form a five to eight membered heterocycloalkyl having 1 to 3 ring heteroatoms selected from O, N, and S; each of $Ar^1, Ar^2, Ar^3$ is independently a halophenyl; each $R^1$ is independently H, $C(O)C_{1-6}$alkyl, or an amino protecting group; each $R^{PG}$ is independently a hydroxyl protecting group or is a saccharide; and m is 0 or 1. $R^{PG}$ comprising a saccharide is meant to indicate that the fluoroglycoside is, e.g., a disaccharide, trisaccharide, a tetrasaccharide, or oligosaccharide, and the method of forming the glycoside bond creates a higher order saccharide—e.g., the fluoroglycoside having a monosaccharide at one $R^{PG}$ (i.e., the fluoroglycoside is a disaccharide) and silyl ether glycoside monosaccharide react to form a glycoside product that is a trisaccharide (two sugar units from the fluoroglycoside starting material and one sugar unit from the silyl ether glycoside). More than one $R^{PG}$ of the fluoroglycoside can comprise a saccharide (and each saccharide present can be the same or different from each other). In some cases, m is 0. In some cases, m is 1.

In general, each of $R^2$, $R^3$, $R^4$, and $R^6$ can comprise independently H, $C_{1-6}$ alkyl, —$N(R^1)_2$, —$N_3$, $CO_2H$, $CO_2C_{1-6}$alkyl, or —$OR^{PG}$, or two of $R^2$, $R^3$, $R^4$, and $R^6$, together with the atoms to which they are attached form a five to eight membered heterocycloalkyl having 1 to 3 ring heteroatoms selected from O, N, and S. In embodiments, at least one $R^2$, $R^3$, $R^4$, and $R^6$ can be —$OR^{PG}$. In embodiments, at least one $R^2$, $R^3$, $R^4$, and $R^6$ can be —$OR^{PG}$ and at least one $R^{PG}$ is benzyl, acetyl, or methyl. In embodiments, at least one of $R^2$, $R^3$, $R^4$, and $R^6$ can be $C_{1-6}$alkyl. In embodiments, each $R^2$, $R^3$, $R^4$, and $R^6$ can be —$OR^{PG}$. In embodiments, each $R^2$, $R^3$, $R^4$, and $R^6$ can be —$OR^{PG}$, and each $R^{PG}$ is benzyl, acetyl, or methyl. In embodiments, each $R^2$, $R^3$, $R^4$, and $R^6$ can be —$OR^{PG}$, and at least one $R^{PG}$ comprises a saccharide. In some embodiments, at least one $R^2$, $R^3$, $R^4$, and $R^6$ can be $C_1$alkyl and the alkyl chain is optionally substituted with 1, 2, or 3 OH or $OR^{PG}$ groups (e.g., a —CH(OH)CH(OH)CH$_2$OH chain, or a derivative thereof where the OH groups are present as a protected version, using a hydroxyl protecting group as discussed herein).

In general, $R^{PG}$ can be a hydroxyl protecting group. Hydroxyl protecting groups include, but are not limited to, —$R^{aa}$, —$N(R^{aa})_2$, —C(=O)$SR^{aa}$, —C(=O)$R^{aa}$, —$CO_2R^{aa}$, —C(=O)$N(R^{aa})_2$, —C(=$NR^{aa}$)$R^{aa}$, —C(=$NR^{aa}$)$OR^{aa}$, —C(=$NR^{aa}$)$N(R^{aa})_2$, —S(=O)$R^{aa}$, —$SO_2R^{aa}$, and —Si$(R^{aa})_3$ wherein each instance of $R^{aa}$ is as described herein. Hydroxyl protecting groups are well known to those of skill in the art and are further described in detail throughout *Protecting Groups in Organic Synthesis*, T. W. Greene and P. G. M. Wuts, 3rd edition, John Wiley & Sons, 1999, incorporated herein by reference.

Exemplary hydroxyl protecting groups include, but are not limited to, methyl, benzyl, acetyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris(benzoyloxyphenyl)methyl, 3-(imidazol-1-yl)bis(4',4"-dimethoxyphenypmethyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEI PS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, tri phenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In embodiments, at least one $R^{PG}$ can comprise a connection to a solid support or to a fluorinated alkyl chain. In such embodiments, it is contemplated that the disclosed glycoside product formation occurs on the solid support, and iterative processes can occur to introduce successive saccharide moieties via additional glycoside bond formation using the disclosed fluoroglycoside and silyl ether glycoside coupling in the presence of a triaryl borane catalyst. When the fluorinated alkyl chain is present, as similar type iterative process is contemplated, wherein the purification of the glycoside product can occur through affinity chromatography due to the fluoroalkyl (typically perfluoroalkyl) chain. In either case, whether solid support or fluorinated alkyl chain, it is further contemplated that the solid support or fluorinated alkyl chain is cleaved from the desired glycoside product. Discussion of use of solid supports for automated synthesis can be found, e.g., in Plate et al., *Science,* 291: 1523-1527 (2001); Love and Seeberger, *Angew. Chem. Int. Ed.,* 43:602-605 (2004); and Schofield et al, *Nature,* 418: 785-789 (2002), each of which is incorporated by references in its entirety. Discussion of use of a fluorinated alkyl chain for automated solution phase synthesis can be found in Tang and Pohl, *Org. Lett.,* 17:2642-2645 (2015), the disclosure of which is incorporated by reference in its entirety.

In cases where OR$^{PG}$ itself on a fluoroglycoside used in the disclosed methods comprises a O-silyl ether, it is contemplated that the silyl ether can act as a point of glycoside bond formation either concurrent with the glycoside bond formation of the silyl ether glycoside added to the fluoroglycoside, or can simply act as a protecting group for the relevant hydroxyl group on the fluoroglycoside. An example of such a coupling is shown below:

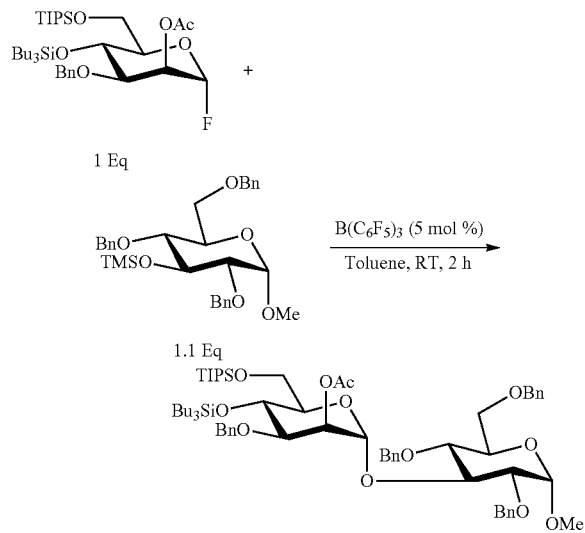

In some cases, the OR$^{PG}$ where R$^{PG}$ is a silyl ether on the fluoroglycoside is the silyl ether glycoside used in the method for glycoside product formation—and the fluoroglycoside/silyl ether glycoside reaction forms a glycoside bond at the C1 carbon and at the carbon of a second molecule where the silyl ether was on the fluoroglycoside. In such cases, the fluoroglycoside compound can go on to further react and form a polymerized or dendrimer product from additional reactions between the fluoroglycoside and the OR$^{PG}$ silyl ether.

In cases where the OR$^{PG}$ silyl ether on the fluoroglycoside acts as a protecting group for one reaction with a different silyl ether glycoside, it can be the point of attachment of a subsequent reaction of another fluoroglycoside. Selection of silyl ether, where the bulkier the substituent on the silicon atom, the less reactive that silicon is and where a primary C6 silyl ether will be more reactive than a secondary C2, C3, or C4 silyl ether, allows for differentiation of the silyl ethers and controls where and in what order the glycoside bonds are formed. For example, a trimethyl silyl (TMS) group at C2 and a tri-isopropyl silyl (TIPS) group at C6 will direct glycoside bond formation at the C2 position first. After an amount of time to allow for reaction between the fluoroglycoside and the silyl ether at C2 to form that glycoside bond, a second fluoroglycoside can be added to the reaction mixture which will then create a glycoside bond at the less reactive C6 TIPS silyl ether to form a second glycoside bond.

In general, each R$^1$ can be independently H, C(O)C$_{1-6}$alkyl, or an amino protecting group. Amino protecting groups can include, but are not limited to, —R$^{aa}$, —N(R$^{aa}$)$_2$, —C(=O)SR$^{aa}$, —C(=O)R$^{aa}$, CO$_2$R$^{aa}$, —C(=O)N(R$^{aa}$)$_2$, —C(=NR$^{aa}$)R$^{aa}$, —C(=NR$^{aa}$)OR$^{aa}$, C(=NR$^{aa}$)N(R$^{aa}$)$_2$, S(=O)R$^{aa}$, SO$_2$R$^{aa}$, and —Si(R$^{aa}$)$_3$, C$_{1-10}$ alkyl, C$_{2-10}$ alkenyl, C$_{2-10}$ alkynyl, C$_{3-10}$ cycloalkyl, C$_{3-14}$ heterocycle, or C$_{6-14}$ aryl, wherein each instance of R$^{aa}$ is independently selected from C$_{1-10}$ alkyl, C$_{2-10}$ alkenyl, C$_{2-10}$ alkynyl, C$_{3-10}$ cycloalkyl, C$_{3-14}$ heterocycle, or C$_{6-14}$ aryl. In embodiments, two R$^1$ can together with the atoms to which they are attached form a five to eight membered heterocycloalkyl having 1 to 3 ring heteroatoms selected from O, N, and S. In embodiments, N(R$^1$)$_2$ is

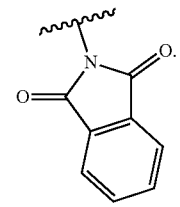 [SMILES: *N1C(=O)c2ccccc2C1=O]

Amino protecting groups are well known to those of skill in the art and are further described in detail throughout *Protecting Groups in Organic Synthesis*, T. W. Greene and P. G. M. Wuts, 3rd edition, John Wiley & Sons, 1999, incorporated herein by reference.

The reactions disclosed herein are catalyzed by a friaryl borane catalyst having a structure of B(Ar$^1$)(Ar$^2$)(Ar$^3$). In general, each of Ar$^1$, Ar$^2$, Ar$^3$ is independently a halophenyl. In some cases, the halophenyl can be a perhalophenyl. In embodiments, at least one of Ar$^1$, Ar$^2$, and Ar$^3$ can be a fluorophenyl. In embodiments, at least two of Ar$^1$, Ar$^2$, and Ar$^3$ can be a fluorophenyl. In embodiments, each of Ar$^1$, Ar$^2$, and Ar$^3$ can be a fluorophenyl. In embodiments, at least one of Ar$^1$, Ar$^2$, and Ar$^3$ can be C$_6$F$_5$. In embodiments, at least two of Ar$^1$, Ar$^2$, and Ar$^3$ can be C$_6$F$_5$. In embodiments, each of Ar$^1$, Ar$^2$, and Ar$^3$ can be a C$_6$F$_5$. In embodiments, at least one Ar$^1$, Ar$^2$, and Ar$^3$ can be

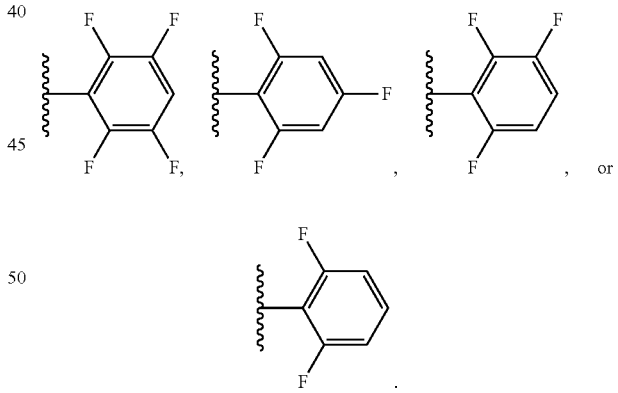

In embodiments, at least two Ar$^1$, Ar$^2$, and Ar$^3$ can be

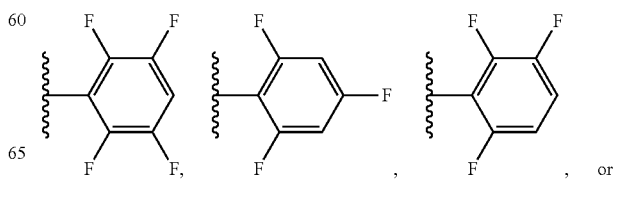

-continued

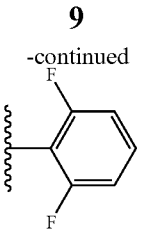

In embodiments, at least one Ar¹, Ar², and Ar³ can be a chlorophenyl. In embodiments, at least one of Ar¹, Ar², and Ar³ can be

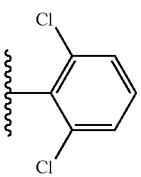

In embodiments, the catalyst can be

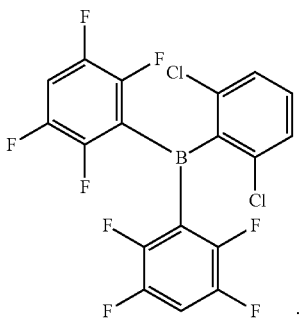 [SMILES: Fc1cc(F)c(F)c(B(c2c(Cl)cccc2Cl)c2c(F)c(F)cc(F)c2F)c1F]

The borane catalyst can further comprise a Lewis base. Some contemplated Lewis bases include water, an alcohol ($R^{aa}$ OH), ether ($R^{aa}OR^{aa}$), an amine ($N(R^{aa})_3$), a pyridine or a derivative thereof, $R^{aa}CN$, $HSR^{aa}$, $S(R^{aa})_2$, or halides, wherein each instance of $R^{aa}$ is independently selected from $C_{1-10}$ alkyl, $C_{2-10}$ alkenyl, $C_{2-10}$ alkynyl, $C_{3-10}$ cycloalkyl, $C_{3-14}$ heterocycle, or $C_{6-14}$ aryl. In embodiments, the catalyst can comprise water, $R^{aa}OH$, $O(R^{aa})_2$, or $N(R^{aa})_3$. In embodiments, $B(Ar^1)(Ar^2)(Ar^3)$ can be a $B(Ar^1)(Ar^2)(Ar^3)$ hydrate. In embodiments, the $B(Ar^1)(Ar^2)(Ar^3)$ hydrate can comprise about 0.1 to 5 water molecules per boron atom. In embodiments, the $B(Ar^1)(Ar^2)(Ar^3)$ hydrate is a monohydrate or a dihydrate. In other embodiments, $B(Ar^1)(Ar^2)(Ar^3)$ is substantially water free, wherein the catalyst has a water content of less than 0.1% by weight. In some cases, the Lewis base is selected from water, methanol, ethanol, propanol, diethyl ether, tetrahydrofuran, pyridine, acetonitrile, tert-butanol, 2,6-lutidine, benzonitrile, fluoride, chloride, bromide, iodide, ethane thiol, thiophenol, dimethylsulfide, trimethylamine, triethylamine, tripropylamine, and dimethylaniline.

In general, the silyl ether glycoside can be any sugar molecule or protected sugar molecule having a silyl ether. As used herein, the term "protected sugar molecule" refers to a sugar molecule (e.g., mono-, di-, tri-, tetra-, or oligo-saccharide) wherein the hydroxyl groups are protected with hydroxyl protecting groups, as discussed above. In embodiments, the silyl ether glycoside can comprise a glycosidic fluorine and a O-silyl ether. In embodiments, the silyl ether glycoside can comprise a structure of Formula (II):

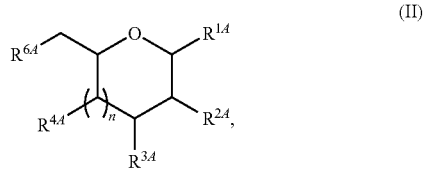

wherein each of $R^{1A}$, $R^{2A}$, $R^{3A}$, $R^{4A}$, and $R^{6A}$ independently is H, an O-silyl ether, $OR^{PG}$, $CO_2H$, $CO_2C_{1-6}$alkyl, or $C_{1-6}$alkyl; each $R^{PG}$ is independently a saccharide or a hydroxyl protecting group; and n is 0 or 1; with the proviso that at least one of $R^{1A}$, $R^{2A}$, $R^{3A}$, $R^{4A}$, and $R^{6A}$ comprises an O-silyl ether. In some cases, n is 0. In some cases, n is 1.

In embodiments, at least one of $R^{1A}$, $R^{2A}$, $R^{3A}$, $R^{4A}$, and $R^{6A}$ can comprise $OR^{PG}$. In embodiments, at least two of $R^{1A}$, $R^{2A}$, $R^{3A}$, $R^{4A}$, and $R^{6A}$ can comprise $OR^{PG}$. In embodiments, each of $R^{1A}$, $R^{2A}$, $R^{3A}$, $R^{4A}$, and $R^{6A}$ that is not an O-silyl ether is a $OR^{PG}$. In embodiments, at least one of $R^{1A}$, $R^{2A}$, $R^{3A}$, $R^{4A}$, and $R^{6A}$ can comprise $CO_2H$ or $CO_2C_{1-6}$alkyl.

In embodiments, one of $R^{1A}$, $R^{2A}$, $R^{3A}$, $R^{4A}$, and $R^{6A}$ can be $C_{1-6}$ alkyl. In embodiments, two of one $R^{1A}$, $R^{2A}$, $R^{3A}$, $R^{4A}$, and $R^{6A}$ can be $C_{1-6}$ alkyl. Contemplated $C_{1-6}$alkyl groups include methyl, ethyl, isopropyl, or tert-butyl. In embodiments, at least one $R^{1A}$, $R^{2A}$, $R^{3A}$, $R^{4A}$ and $R^{6A}$ is methyl. In some embodiments, at least one $R^{1A}$, $R^{2A}$, $R^{3A}$, $R^{4A}$ and $R^{6A}$ can be $C_1$-alkyl and the alkyl chain is optionally substituted with 1, 2, or 3 OH or $OR^{PG}$ groups (e.g., a —CH(OH)CH(OH)CH₂OH chain, or a derivative thereof where the OH groups are present as a protected version, using a hydroxyl protecting group as discussed herein).

In embodiments, at least two of $R^{1A}$, $R^{2A}$, $R^{3A}$, $R^{4A}$, and $R^{6A}$ can comprise an O-silyl ether. In embodiments, two of $R^{1A}$, $R^{2A}$, $R^{3A}$, $R^{4A}$, and $R^{6A}$ can comprise an O-silyl ether. In embodiments, if more than one of $R^{1A}$, $R^{2A}$, $R^{3A}$, and $R^{4A}$ comprises an O-silyl ether, then no two O-silyl ethers are identical. In embodiments, two of $R^{1A}$, $R^{2A}$, $R^{3A}$, $R^{4A}$, and $R^{6A}$ can comprise an O-silyl ether and, wherein $R^{6A}$ and one of $R^{1A}$, $R^{2A}$, $R^{3A}$, and $R^{4A}$ comprise the same O-silyl ether. In embodiments, at least three of $R^{1A}$, $R^{2A}$, $R^{3A}$, $R^{4A}$, and $R^{6A}$ can comprise an O-silyl ether.

In general, O-silyl ethers are well known to those of skill in the art and are further described in detail throughout *Protecting Groups in Organic Synthesis*, T. W. Greene and P. G. M. Wuts, 3rd edition, John Wiley & Sons, 1999, incorporated herein by reference. In embodiments, the O-silyl ether can comprise trimethylsilyl ether (OTMS), triethylsilyl ether (TES), tert-butyldimethylsilyl ether (OTBS), tert-butyldiphenylsilyl ether (OTBDPS), or triisopropylsilyl ether (OTIPS).

In embodiments, one of $R^{1A}$, $R^{2A}$, $R^{3A}$, $R^{4A}$, and $R^{6A}$ can comprise OTMS. In embodiments, one of $R^{1A}$, $R^{2A}$, $R^{3A}$, $R^{4A}$, and $R^{6A}$ can comprise OTBS. In embodiments, one of $R^{1A}$, $R^{2A}$, $R^{3A}$, $R^{4A}$, and $R^{6A}$ can comprise OTIPS. In embodiments, one of $R^{1A}$, $R^{2A}$, $R^{3A}$, $R^{4A}$, and $R^{6A}$ can comprise OTMS, and one of $R^{1A}$, $R^{2A}$, $R^{3A}$, $R^{4A}$, and $R^{6A}$ can comprise OTBS. In embodiments, one of $R^{1A}$, $R^{2A}$, $R^{3A}$, $R^{4A}$, and $R^{6A}$ can comprise OTMS, and one of $R^{1A}$, $R^{2A}$, $R^{3A}$, $R^{4A}$, and $R^{6A}$ can comprise OTIPS. In embodiments, one of $R^{1A}$, $R^{2A}$, $R^{3A}$, $R^{4A}$, and $R^{6A}$ can comprise OTBS, and one of $R^{1A}$, $R^{2A}$, $R^{3A}$, $R^{4A}$, and $R^{6A}$ can comprise OTIPS.

In embodiments, $R^{6A}$ and one of $R^{1A}$, $R^{2A}$, $R^{3A}$, and $R^{4A}$ can comprise OTMS. In embodiments, $R^{6A}$ and one of $R^{1A}$, $R^{2A}$, $R^{3A}$, and $R^{4A}$ comprise OTBS. In embodiments, $R^{6A}$ and one of $R^{1A}$, $R^{2A}$, $R^{3A}$, and $R^{4A}$ can comprise OTIPS.

The discussion above regarding the presence of a silyl ether that acts first as a hydroxyl protecting group then as the silyl ether glycoside, based upon differentiated reactivity compared to other silyl ethers applies for the selection of silyl ethers as protecting groups for the silyl ether glycoside. A silyl ether glycoside as used in the disclosed methods can have a second silyl ether present, which is less reactive but can later be used as the point of attachment for a subsequent glycosidic bond formation upon reaction with a second fluoroglycoside.

In embodiments, at least one of $R^{1A}$, $R^{2A}$, $R^{3A}$, $R^{4A}$, and $R^{6A}$ is $CO_2H$ or $CO_2C_{1-6}$alkyl. In some embodiments, at least one of $R^{1A}$, $R^{2A}$, $R^{3A}$, $R^{4A}$, and $R^{6A}$ is $C_{1-6}$alkyl, and the $C_{1-6}$alkyl group can be substituted with 1, 2, or 3 OH groups or a protected version thereof (e.g., $OR^{PG}$) with a hydroxyl protecting group as discussed herein (e.g., $CH(OH)CH(OH)CH_2OH$ or $CH(OR^{PG})CH(OR^{PG})CH_2OR^{PG}$).

In embodiments, one O-silyl ether can comprise a di-silyl ether having a structure of

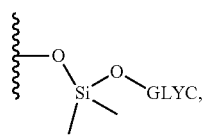

wherein GLYC is a glycoside moiety. As used herein, the term "glycoside moiety" can be any sugar moiety (e.g., mono-, di-, tri-, tetra-, or oligosaccharide). In embodiments, GLYC can have a structure selected from the group consisting of:

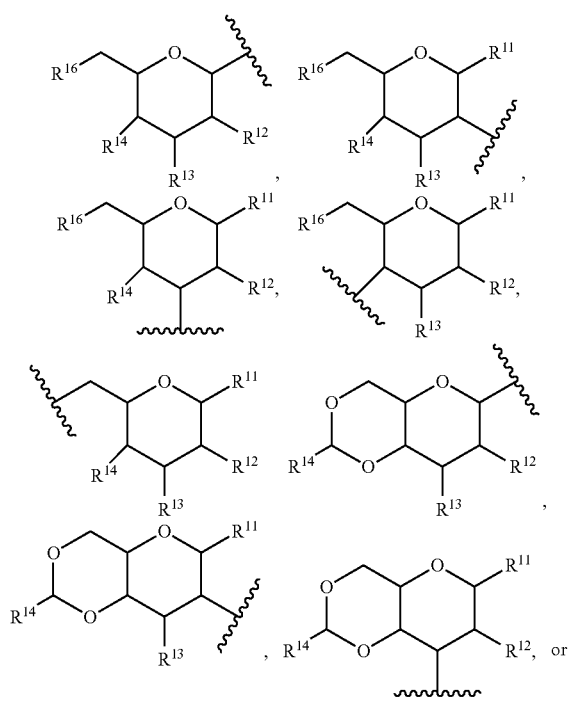

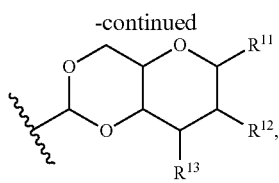

and each of $R^{11}$, $R^{12}$, $R^{13}$, $R^{14}$, $R^{15}$, and $R^{16}$ is independently H, $—OR^{PG}$, $C_{1-6}$ alkyl, $Ar^4$, or $—N(R^1)_2$, or two of $R^{11}$, $R^{12}$, $R^{13}$, $R^{14}$, $R^{15}$, and $R^{16}$, together with the atoms to which they are attached form a five to eight member heterocycloalkyl comprising 1 to 3 ring heteroatoms selected from O, N, and S, and each $Ar^4$ is independently selected from $C_6$-$C_{22}$ aryl or a 5-12 membered heteroaryl comprising from 1 to 3 ring heteroatoms selected from O, N, and S. In embodiments, at least one of $R^{11}$, $R^{12}$, $R^{13}$, $R^{14}$, $R^{15}$, and $R^{16}$ is $—OR^{PG}$. In embodiments, each of $R^{11}$, $R^{12}$, $R^{13}$, $R^{14}$, $R^{15}$, and $R^{16}$, when present, is $—OR^{PG}$. In embodiments, at least one of $R^{11}$, $R^{12}$, $R^{13}$, $R^{14}$, $R^{15}$, and $R^{16}$ is $—OR^{PG}$ and $R^{PG}$ can be benzyl, acetyl, or methyl. In embodiments, at least one of $R^{11}$, $R^{12}$, $R^{13}$, $R^{14}$, $R^{15}$, and $R^{16}$ is $C_{1-6}$alkyl. In embodiments, at least one of $R^{11}$, $R^{12}$, $R^{13}$, $R^{14}$, $R^{15}$, and $R^{16}$ is methyl. In embodiments, at least one of $R^{11}$, $R^{12}$, $R^{13}$, $R^{14}$, $R^{15}$, and $R^{16}$ is $Ar^4$. In embodiments, at least one of $R^{11}$, $R^{12}$, $R^{13}$, $R^{14}$, $R^{15}$, and $R^{16}$ is phenyl.

As used herein, the term "alkyl" refers to straight chained and branched saturated hydrocarbon groups containing one to six carbon atoms, for example, one to five carbon atoms, or one to four carbon atoms, or one to three carbon atoms. The term $C_n$ means the alkyl group has "n" carbon atoms. For example, $C_4$ alkyl refers to an alkyl group that has 4 carbon atoms. $C_{1-6}$alkyl and $C_1$-$C_6$ alkyl refer to an alkyl group having a number of carbon atoms encompassing the entire range (i.e., 1 to 6 carbon atoms), as well as all subgroups (e.g., 1-6, 2-5, 1-5, 3-6, 1, 2, 3, 4, 5, and 6 carbon atoms). Nonlimiting examples of alkyl groups include, methyl, ethyl, n-propyl, isopropyl, n-butyl, sec-butyl, tert-butyl. Unless otherwise indicated, an alkyl group can be an unsubstituted alkyl group or a substituted alkyl group. As discussed herein, in some cases, the alkyl is substituted with 1, 2, or 3 OH groups that can be present as a protected form (i.e., as $OR^{PG}$ as discussed herein).

As used herein, the term "heterocycloalkyl" is defined as an aliphatic cyclic hydrocarbon group containing five to twelve ring atoms of which one to three of those ring atoms are heteroatoms independently selected from oxygen, nitrogen, and sulfur, and the rest of the ring atoms are carbon. In some cases, the heterocycloalkyl is a ring containing a total of five to eight atoms, of which 1, 2, or 3 of those atoms are heteroatoms independently selected from the group consisting of oxygen, nitrogen, and sulfur, and the remaining atoms in the ring are carbon atoms. Nonlimiting examples of contemplated heterocycloalkyl groups include piperdine, tetrahydrofuran, tetrahydropyran, dihydrofuran, and morpholine. Heterocycloalkyl groups can be saturated or partially unsaturated ring systems optionally substituted with, for example, one to three groups, independently selected alkyl, alkenyl, OH, $C(O)NH_2$, $NH_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to eight total ring atoms, and one to three heteroatoms. In some embodiments, the heterocycloalkyl groups described herein comprise one oxygen ring atom (e.g., oxiranyl, oxetanyl, tetrahydrofuranyl, and tetrahydropyranyl).

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group. The term "halophenyl" refers to an phenyl group that is substituted with at least one halogen, and includes perhalogenated phenyl (i.e., all hydrogen atoms substituted with halogen).

As used herein, the term "heteroaryl" refers to a cyclic aromatic ring having five to twelve total ring atoms (e.g., a monocyclic aromatic ring with 5-6 total ring atoms), and containing one to three heteroatoms selected from nitrogen, oxygen, and sulfur in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each ring can contain five or six total ring atoms and one to three heteroatoms in its aromatic ring.

As used herein, the term "halo" is defined as fluoro, chloro, bromo, and iodo.

As used herein, the term "amino" refers to a —$NH_2$ group, wherein one or both hydrogen can be replaced with an alkyl, cycloalkyl, aryl group, or an amino protecting group, as discussed above.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

The triaryl borane catalyst disclosed herein displays remarkable efficiency. The coupling reactions that have a fluoroglycosides and/or silyl ethers with "armed" substituents, such as $OR^{PG}$, wherein the $R^{PG}$ is a benzyl group, are extremely fast reaction, proceeding within minutes. In embodiments, the admixing of the methods disclosed herein can occur for about 1 minute to about 60 minutes, e.g., about 5 to 45 min, about 5 to 30 min, about 5 to 15 min, or about 5 to 10 min. In embodiments, the admixing can occur for about 1 minute, 2 minutes, 3 minutes, 4 minutes, 5 minutes, 6 minutes, 7 minutes, 8 minutes, 9 minutes, 10 minutes, 15 minutes, 20 minutes, 30 minutes, 40 minutes, 45 minutes, 50 minutes, or 60 minutes. The coupling reactions that have fluoroglycosides and/or silyl ethers with "disarmed" substituents, such as $OR^{PG}$, wherein the $R^{PG}$ is an acetyl group, are also fast reactions, proceeding within hours, e.g., 1 to 24 hours, 1 to 15 hours, 10 to 24 hours, 10 to 15 hours, or 12 to 24 hours. In embodiments, the admixing of the methods disclosed herein can occur for about 1 minute to about 24 hours, or about 1 hour, 5 hours, 10 hours, 15 hours, 20 hours, or 24 hours.

The triaryl borane catalyzed reaction can be highly efficient, with a turnover of about 200 turnovers or better. In embodiments, the catalyst is present in an amount of less than 25 mol %, based upon the mol amount of the fluoroglycoside. The catalyst can be present at less than 20 mol %, 15 mol %, 10 mol %, 9 mol %, 8 mol %, 7 mol %, 6 mol %, 5 mol %, 4 mol %, 3 mol %, 2 mol %, 1 mol %, 0.5 mol %, or 0.1 mol %. In some cases, the catalyst is present in an amount of 0.1 mol % to 10 mol %, 1 to 10 mol %, 5 to 20 mol %, or 1 to 5 mol %.

In embodiments, the methods can comprise the fluoroglycoside and the silyl ether glycoside present in a molar ratio of about 0.5 to 1.5, or 0.6 to 1.4, or 0.7 to 1.3, or 0.8 to 1.2, or 0.9 to 1.1, or 1 to 1. In embodiments, the fluoroglycoside and the silyl ether glycoside are present in a molar ratio of about 0.9 to 1 to about 1.1 to 1.

The reaction disclosed herein can occur in solution, such as in the presence of one or more organic solvents. Suitable solvents include nonpolar aprotic solvents, such as, but not limited to, benzene, toluene, hexanes, pentanes, dichloromethane, trichloromethane, a chloro-substituted benzene, a deuterated analog of any of the foregoing and any combination of the foregoing. As will be understood by one of ordinary skill in the art, polar aprotic solvents may also be suitable provided they do not compete with the coupling reaction to coordinate to the catalyst. Suitable polar aprotic solvents can include, but are not limited to, diethyl ether, dimethoxyethane, tetrahydrofuran, a deuterated analog of the foregoing, and any combination of the foregoing. In some cases, the reaction occurs in the presence of toluene or dichloromethane.

In embodiments, the methods herein can occur in open atmosphere (not under inert atmosphere). In embodiments, the catalyst can be used in inert atmosphere, e.g., substantially in the absence of oxygen and moisture, wherein the inert atmosphere is substantially $N_2$ or Ar. In embodiments, the methods herein can be conducted at room temperature with all reagents handled and weighed in open atmosphere. In embodiments, the methods herein can be conducted at any suitable temperature as determined by one of skill in the art. In embodiments, the methods herein can occur at room temperature or elevated temperatures, such as 40° C. to 100° C.

As noted above, installation of a silyl ether protecting group (O-silyl ether) allows the relative reactivity of different hydroxyls from the glycosides to be controlled by the characteristics of the O-silyl ether(s) rather than inherent reactivity. This important feature allows iterative one-pot procedures to be conducted. Said iterative methods can be used to synthesize oligosaccharides. In embodiments, the glycoside product can comprises a second silyl ether. In embodiments, the methods herein can comprise a glycoside product comprising a second silyl ether and further comprising admixing a second fluoroglycoside with the glycoside product to form a second glycoside product between the second fluoroglycoside and the second silyl ether on the glycoside product. In embodiments, the second glycoside product can comprise third silyl ether. In embodiments, the methods herein can comprise a second glycoside product comprising a third silyl ether and further comprising admixing a third fluoroglycoside with the second glycoside product to form a third glycoside product between the third fluoroglycoside and the third silyl ether on the second glycoside product.

In embodiments, silicon protecting groups can be selected based on their reactivity features in order to synthesize particular oligosaccharides with specific stereochemistries. In embodiments, the methods herein can comprise admixing a first fluoroglycoside of formula (I) and a silyl ether of formula (II) in the presence of a catalyst having a formula $B(Ar^1)(Ar^2)(Ar^3)$ under conditions sufficient to form a first glycoside product, wherein at least two of $R^{1A}$, $R^{2A}$, $R^{3A}$, $R^{4A}$, and $R^{6A}$ of the silyl ether of formula (II) comprise a different O-silyl ether, and the methods further can comprise admixing a second fluoroglycoside of formula (I) with the first glycoside product after a period of time sufficient to allow the first glycoside product to form, in the presence of a catalyst of formula $B(Ar^1)(Ar^2)(Ar^3)$ under conditions sufficient to form a second glycoside product. For example, three monosaccharides can be combined to access a single trisaccharide with complete site-selectivity and complete stereocontrol, such as shown below

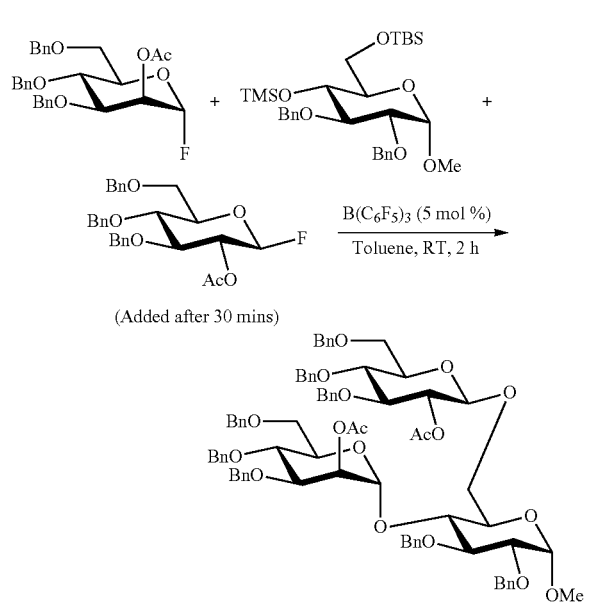

Notably, in this example, by using the silicon structure variation to control reactivity, the hindered $R^{4a}$ OSiMe$_3$ group reacts first, followed by reaction of the $R^{6a}$ OSiMe$_2$-t-Bu group.

In embodiments, a method can comprise admixing a two equivalents of the same fluoroglycosides of formula (I) and a single equivalent of a silyl ether of formula (II) in the presence of a catalyst having a formula $B(Ar^1)(Ar^2)(Ar^3)$ under conditions sufficient to form a glycoside product, wherein at least two of $R^{1A}$, $R^{2A}$, $R^{3A}$, $R^{4A}$, and $R^{6A}$ of the silyl ether of formula (II) comprise a different O-silyl ether. For example, a trisaccharide was made via a 2:1 equivalents coupling wherein two equivalents of the same fluorglycosides of formula (I) were admixed with a single equivalent of silyl ether to form the glycoside product, shown below

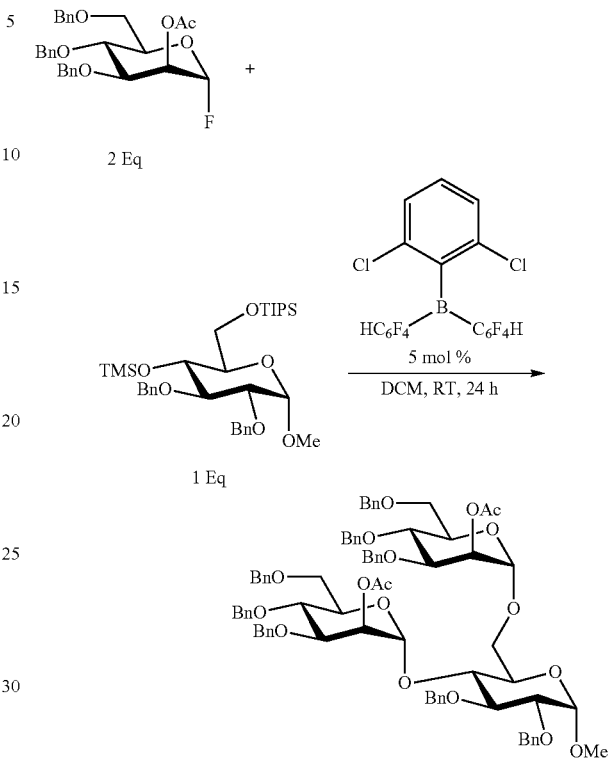

The methods described herein can comprise a fluoroglycoside of formula (I) and a silyl ether glycoside that are part of the same molecule reacting in an intramolecular fashion to form a glycoside product. In embodiments, the silyl ether glycoside can have a structure of formula (II), where one of $R^{1A}$, $R^{2A}$, $R^{3A}$, $R^{4A}$, and $R^{6A}$ can comprise a di-silyl ether having a structure of

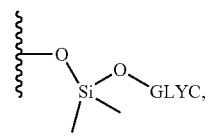

and the GLYC is the fluoroglycoside of a structure of formula (I). In embodiments, the method can comprise admixing the silyl ether glycoside having a structure of formula (II) wherein one of $R^{1A}$, $R^{2A}$, $R^{3A}$, $R^{4A}$, and $R^{6A}$ can comprise a di-silyl ether having a structure of

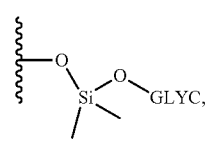

wherein GLYC is a fluoroglycoside of a structure of formula (I), in the presence of a catalyst having a formula $B(Ar^1)(Ar^2)(Ar^3)$ under conditions sufficient to form a glycoside product. In embodiments, the intramolecular reactions can enable changes in the stereochemical outcomes, such as, from axial to equatorial or from equatorial to axial. The intramolecular reactions described above can synthesize a disaccharides, such as shown in the two examples below

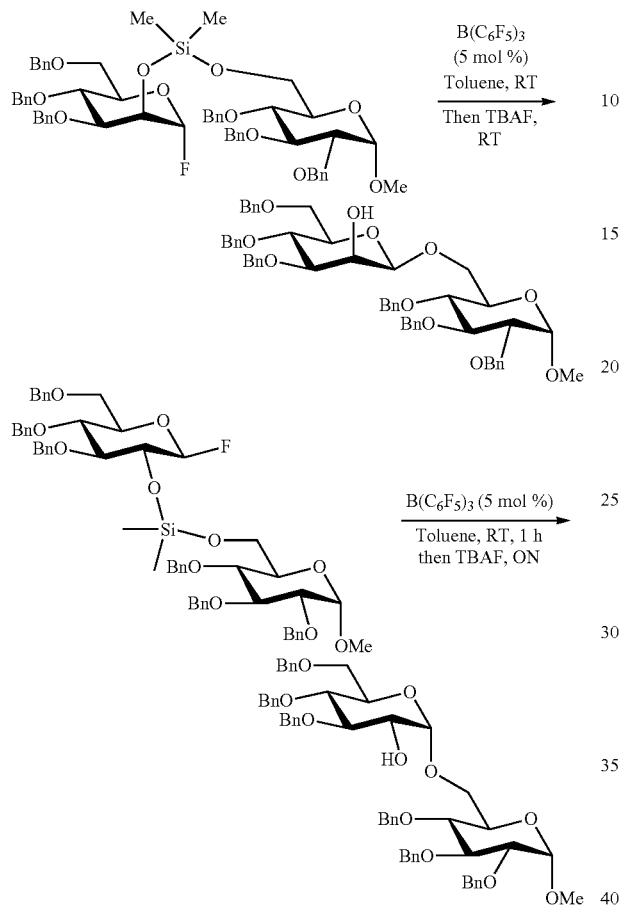

Further, the methods described herein can comprise a fluoroglycoside of formula (I) and a silyl ether glycoside that are part of the same molecule reacting in an intramolecular fashion to form a glycoside product, but iteratively, a second (or third or fourth) fluoroglycoside of formula (I) can be admixed with said product to form higher value oligosaccharides. In embodiments, the methods disclosed herein can comprise admixing the silyl ether glycoside having a structure of formula (II) wherein one of $R^{1A}$, $R^{2A}$, $R^{3A}$, $R^{4A}$, and $R^{6A}$ can comprise a di-silyl ether having a structure of

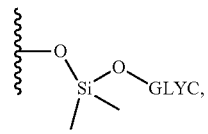

the GLYC can be a first fluoroglycoside of a structure of formula (I), in the presence of a catalyst having a formula $B(Ar^1)(Ar^2)(Ar^3)$, and after a period of time sufficient to allow the intramolecular reaction to occur, the method further comprising admixing a second fluoroglycoside of a structure of formula (I), under conditions sufficient to form a second glycoside product. In embodiments, the intermolecular and intramolecular methods can be combined in one pot (intramolecular method occurs first, followed by addition of the third glycoside for intermolecular coupling). In embodiments, the combined methods can enable preparation of trisaccharides that possess both 1,2-cis and 1,2-trans linkages, such as the example below

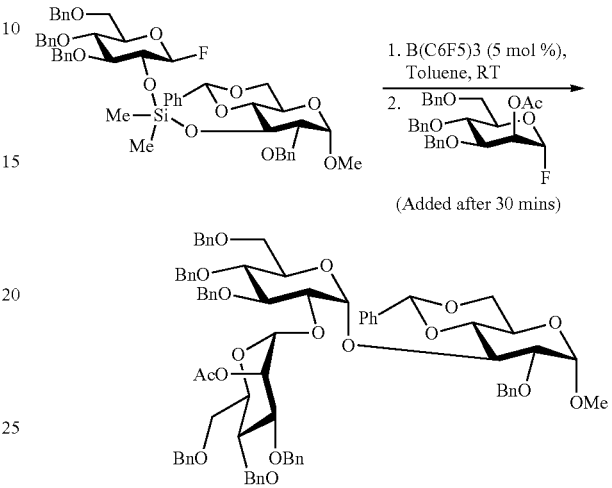

The intramolecular versions of the methods herein can enable changes in the stereochemical outcome. Notably, this finding enables intermolecular couplings to produce alpha-mannosides and intramolecular couplings allow preparation of beta-mannosides, in both cases with product formed as single stereoisomers. The same strategy allows preparation of either alpha- or beta-glucosides using intra- or intermolecular glycosylations. The methods herein can form glycoside products in all four 1,2-stereoisomers with high selectivity, via a strategy that is invariant of protection scheme at $R^3$, $R^4$, and $R^6$, or $R^{3A}$, $R^{4A}$, and $R^{6A}$, or $R^{13}$, $R^{14}$, and $R^{16}$.

The methods herein are envisioned to be both simple, in the formation of disaccharides, and iterative in the formation of oligosaccharides. In embodiments, the methods herein can form many variations of glycoside products, such as disaccharides, trisaccharides, tetrasaccharides, pentasaccharides, or higher oligosaccharides. In embodiments, the glycoside product can be

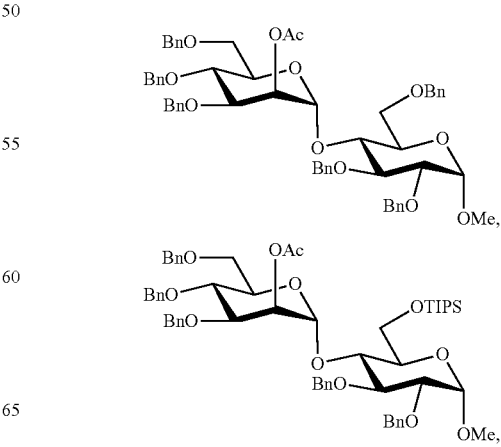

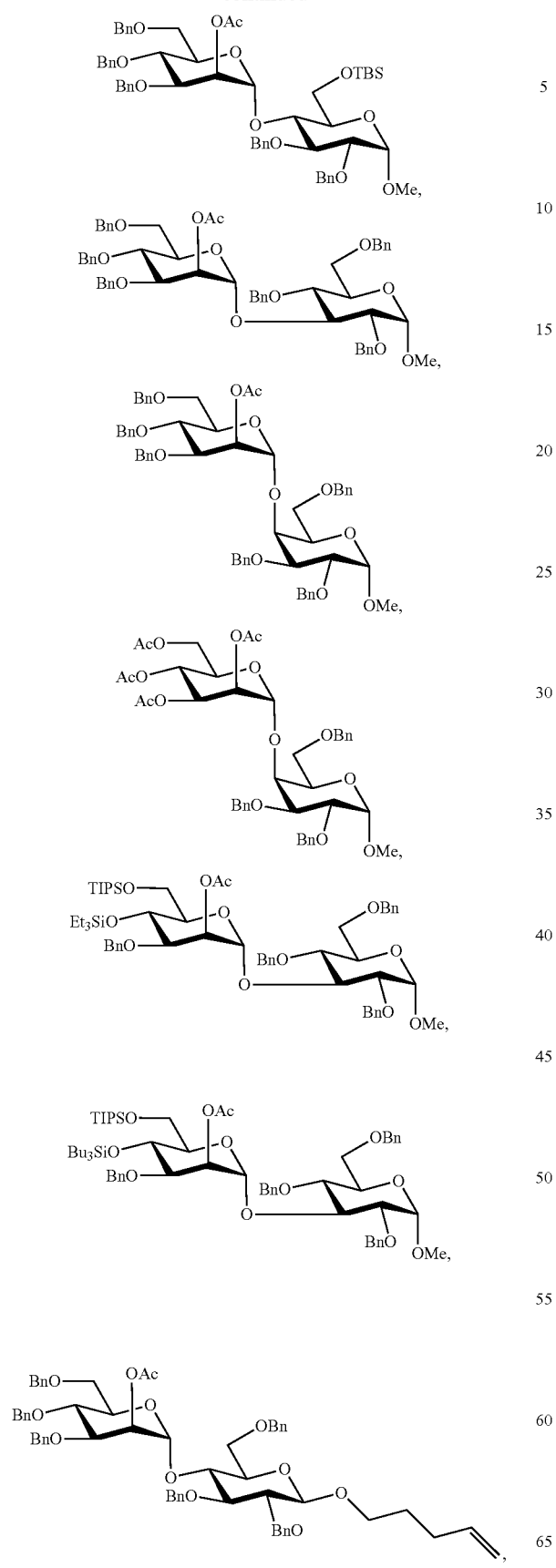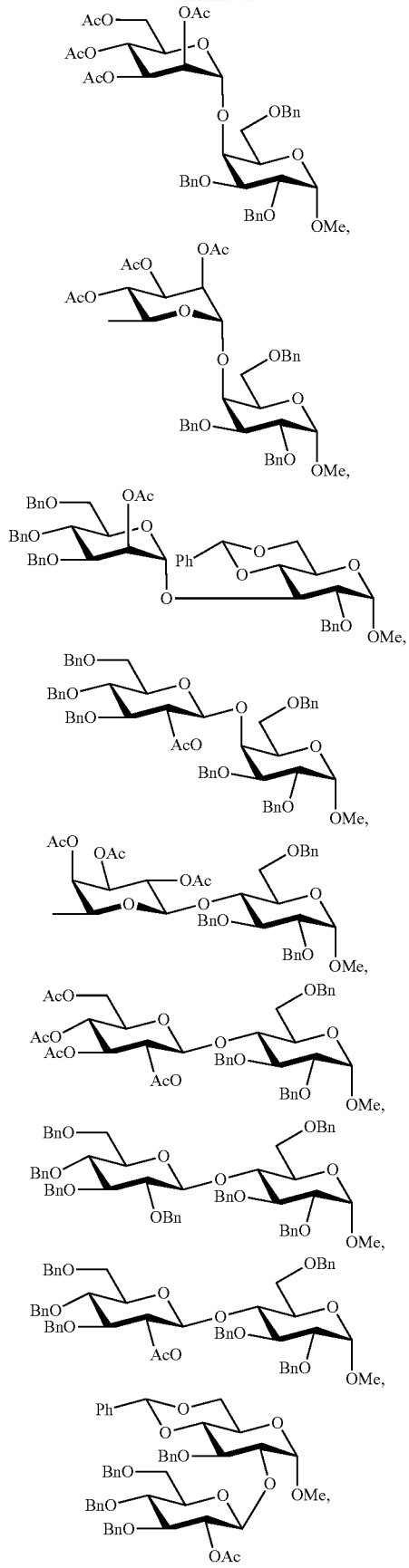

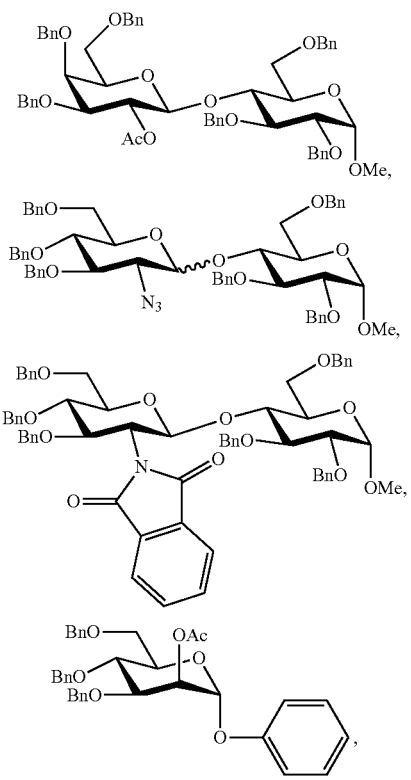
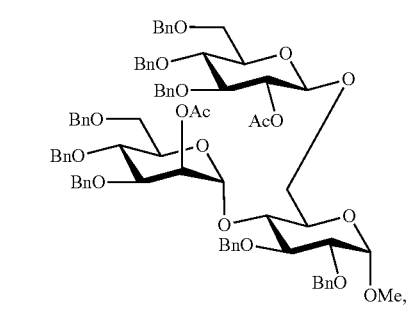
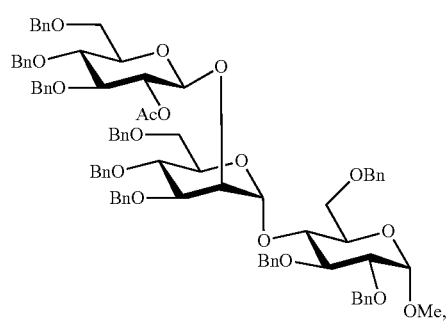
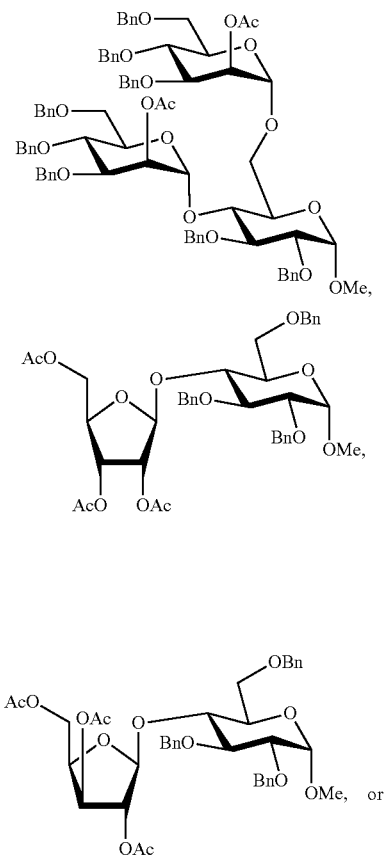
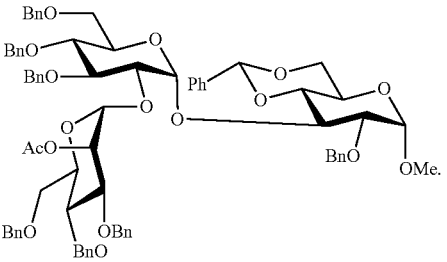
In embodiments, the second glycoside product can be
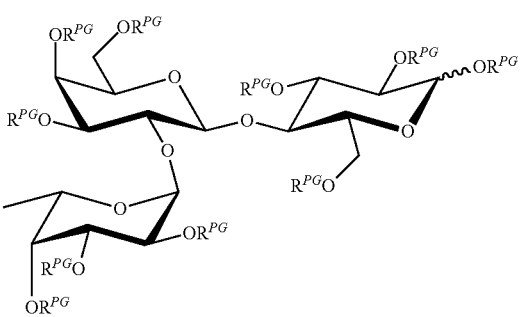

In embodiments, the second glycoside product can be

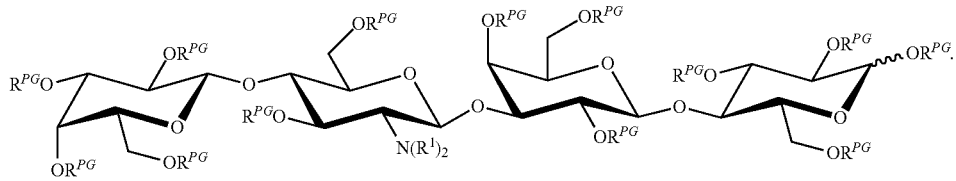

In embodiments, the third glycoside product can be

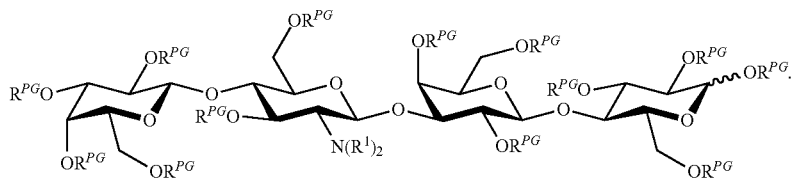

The methods herein can comprise the final glycoside product being formed in a yield of at least 30%, at least 40%, at least 50%, at least 60%, at least 70%, at least 80%, at least 90%, or at least 95%.

The methods herein can be stereoselective. As used herein the term "stereoselective" refers to the methods herein producing a single stereoisomer in greater than 60% yield based on the amount of total glycoside product. The methods herein can comprise the final glycoside product being formed in a single stereoisomer. In embodiments, the methods herein can comprise a single stereoisomer of the final glycoside product being formed in 70%, 80%, 85%, 90%, 95%, 98%, 99% yield or more, based on the total amount of final glycoside product. In embodiments, the methods herein can comprise a single stereoisomer of the final glycoside product being formed in 80% yield or more. In embodiments, the methods herein can comprise a single stereoisomer of the final glycoside product being formed in 90% yield or more.

EXAMPLES

Materials and Methods: All experiments were carried out under a dry nitrogen atmosphere unless otherwise specified. All reagents were purchased from commercial suppliers and were used without further purification unless otherwise specified. "Room Temperature" for all experiments was approximately 23° C. and "high vacuum" refers to approximately $10^{-3}$ Torr. Tris(pentafluorophenyl) borane was purchased from Strem Chemical and was used as received. L-Rhamnose monohydrate, Methyl-α-D-galactopyranoside, Methyl-α-D-glucopyranoside, D-Mannose and, 2,3,4,6-Tetra-O-acetyl-α-D-Glucose were purchased from Sigma Aldrich and used as received. 4 Å molecular sieves were activated via extensive flame drying under high vacuum, or by heating to 220° C. for 12 hours under high vacuum. Boron trifluoride diethyl etherate and Trimethylsilyl trifluoromethanesulfonate were distilled from CaH into a Teflon capped receiving flask and stored under $N_2$ prior to use. All solvents were dried under nitrogen using a solvent purification system (Innovative Technology, Inc. Model # SPS400-3 and PS-400-3) or distilled from CaH and stored over activated 4 Å molecular sieves.

Chromatographic purifications were carried over silica gel unless otherwise specified. Kieselgel 60 F254 (250 μm silica gel) glass plates were utilized for TLC analysis and were visualized by UV irradiation (254 nm) and by charring with sulfuric acid in ethanol (10:90, v/v) or with ceric ammonium molybdate solution [$Ce(SO_4)_2$: 4 g, $(NH_4)_6Mo_7O_{24}$: 10 g, $H_2SO_4$: 40 mL, $H_2O$: 360 mL]. Flash column chromatography was performed using SiliaFlash® P60 (230-400 mesh) silica gel. If so noted, further purification of products was undertaken using semi-preparative HPLC with a Beckman Coulter System Gold HPLC equipped with a Waters XBridge BEH C18 column (dimensions, 250×10 mm; particle size, 5 μm; pore size, 130 Å). The flow rate was maintained at 3 mL/min, and the mobile phase consisted of an acetonitrile/water mixture. All crude material was dissolved in acetonitrile and filtered through 0.20 μm PTFE filters (EMD Millipore) prior to manual HPLC injection. UV absorption was monitored at 240 nm and 260 nm.

$^1$H and $^{13}$C NMR spectra of all compounds were recorded using 500 and 700 MHz instruments and all $^{19}$F NMR spectra were collected on 400 MHz instruments. ESI-HRMS were recorded using an Agilent 6230 TOF HPLC-MS.

Example 1: Preparation of Monosaccharide Substrates

General experimental procedure (A) for trimethylsilyl protection of acceptors. A stirred solution of alcohol (3.23 mmol) in dichloromethane (15 mL) was treated with catalytic iodine (0.16 mmol), and hexamethyldisilazane (0.54 mmol). The reaction mixture was stirred for 1 h at rt before finely powdered $Na_2S_2O_3$ (3 g) was added portion wise with vigorous stirring. After stirring for additional 0.5 h the reaction mixture was filtered, and the filtrate was concentrated under reduced pressure. The residue was subjected to column chromatography on silica gel to give the desired TMS ether product (Karimi et al., J. Org. Chem. 2000, 65 (21), 7228-30).

General experimental procedure (B) for trimethylsilyl protection of acceptors. A stirred solution of alcohol (0.94 mmol) in dichloromethane (5 mL) was treated with triethylamine (3.77 mmol) and chlorotrimethylsilane (1.88 mmol) at 0° C. The reaction mixture was allowed to warm to rt and

Methyl-2,3,6-tri-O-benzyl-4-O-trimethylsilyl-α-D-glucopyranoside stirring was continued for 2 hours at room temperature (rt) before it was concentrated to dryness under reduced pressure. The residue was dissolved in dichloromethane (100 mL), and dichloromethane layer was washed with aq. NaHCO$_3$ (2×100 mL), dried over anhydrous Na$_2$SO$_4$, and concentrated under reduced pressure. The residue was subjected to column chromatography on silica gel to give the desired TMS ether product.

Methyl-2,3,6-tri-O-benzyl-4-O-trimethylsilyl-α-D-glucopyranoside

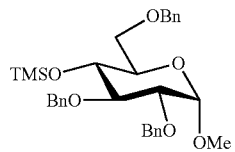

This compound was prepared by following the general experimental procedure (A) using methyl-2,3,6-tri-O-benzyl-α-D-glucopyranoside (3 g, 6.46 mmol), catalytic iodine (82 mg, 0.32 mmol), and hexamethyldisilazane (1.1 mL, 5.16 mmol). Purification by column chromatography eluting with ethyl acetate/hexane (1:19 to 1:4) afforded the desired product (3.07 g, 5.55 mmol, 86%) as a white foam.

Methyl-2,3,6-tri-O-benzyl-4-O-trimethylsilyl-α-D-galactopyranoside

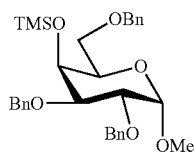

This compound was prepared by following the general experimental procedure (A) using methyl-2,3,6-tri-O-benzyl-α-D-galactopyranoside (313 mg, 0.67 mmol), catalytic iodine (8.6 mg, 0.03 mmol), and hexamethyldisilazane (0.11 mL, 0.54 mmol). Purification by column chromatography eluting with ethyl acetate/hexane (1:19 to 1:4) afforded the desired product (315 mg, 0.58 mmol, 87%) as a colorless viscous liquid. $^1$H NMR (700 MHz, CDCl$_3$) δ 7.37-7.23 (m, 15H), 4.79 (dd, J=15.8, 11.8 Hz, 2H), 4.73-4.63 (m, 3H), 4.54-4.48 (m, 2H), 4.13 (d, J=2.8 Hz, 1H), 3.92-3.84 (m, 2H), 3.78 (dd, J=10.1, 2.8 Hz, 1H), 3.57 (dd, J=9.2, 7.2 Hz, 1H), 3.49 (dd, J=9.2, 5.8 Hz, 1H), 3.37 (s, 3H), 0.05 (s, 9H). $^{13}$C NMR (176 MHz, CDCl$_3$) δ 138.7, 138.6, 138.1, 128.5 (2C), 128.3, 128.2, 128.0, 127.9 (2C), 127.8, 127.6, 99.0, 78.1, 75.9, 73.9, 73.8, 73.5, 70.2, 69.6, 69.2, 55.5, 0.7. ESI-HRMS m/z: Calcd. for C$_{31}$H$_{40}$O$_6$SiK [M+K]$^+$: 575.2226; found: 575.2224.

Methyl-2,4,6-tri-O-benzyl-3-O-trimethylsilyl-α-D-glucopyranoside

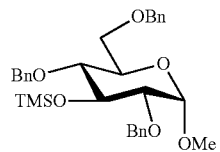

This compound was prepared by following the general experimental procedure (A) using methyl-2,4,6-tri-O-benzyl-α-D-glucopyranoside (567 mg, 1.22 mmol) catalytic iodine (16 mg, 0.67 mmol), and hexamethyldisilazane (87 mg, 0.54 mmol). Purification by column chromatography eluting with ethyl acetate/hexane (1:19 to 1:4) afforded the desired product (570 mg, 1.06 mmol 87%) as a colorless viscous liquid. $^1$H NMR (700 MHz, CDCl$_3$) δ 7.40-7.37 (m, 2H), 7.37-7.33 (m, 2H), 7.33-7.28 (m, 7H), 7.28-7.24 (m, 2H), 7.21-7.18 (m, 2H), 4.85 (d, J=11.0 Hz, 1H), 4.80 (d, J=12.3 Hz, 1H), 4.57 (d, J=12.1 Hz, 1H), 4.53 (d, J=12.3 Hz, 1H), 4.49 (d, J=11.0 Hz, 1H), 4.48-4.45 (m, 2H), 4.05 (t, J=9.0 Hz, 1H), 3.71-3.65 (m, 2H), 3.64-3.57 (m, 1H), 3.50 (t, J=9.1 Hz, 1H), 3.36 (dd, J=9.4, 3.6 Hz, 1H), 3.30 (s, 3H), 0.19 (s, 9H). $^{13}$C NMR (176 MHz, CDCl$_3$) δ 138.5 (2C), 138.1, 128.6, 128.5 (20) 128.4 (2C), 128.0 (2C), 127.8, 127.7, 127.6, 98.4, 80.1, 79.0, 75.0, 74.7, 73.8, 73.6, 69.9, 68.9, 55.2, 0.9. ESI-HRMS m/z: Calcd. for C$_{31}$H$_{40}$O$_6$SiNa [M+Na]$^+$: 559.2492; found: 559.2486.

Methyl-2,3-di-O-benzyl-4-O-trimethylsilyl-6-O-triisopropylsilyl-α-D-glucopyranoside

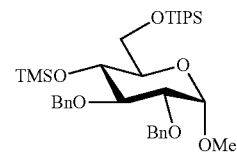

This compound was prepared by following the general experimental procedure (B) using methyl-2,3-di-O-benzyl-6-O-triisopropylsilyl-α-D-glucopyranoside (500 mg, 0.94 mmol), triethylamine (0.52 mL, 3.77 mmol), and chlorotrimethylsilane (0.24 mL, 1.89 mmol). Purification by column chromatography eluting with ethyl acetate/hexane (1:19 to 1:4) afforded the desired product (500 mg, 0.83 mmol, 88%) as a colorless viscous liquid. $^1$H NMR (700 MHz, CDCl$_3$) δ 7.37-7.25 (m, 10H), 5.00 (d, J=11.1 Hz, 1H), 4.75 (d, J=11.2 Hz, 1H), 4.70 (d, J=12.0 Hz, 1H), 4.60 (d, J=12.0 Hz, 1H), 4.57 (d, J=3.6 Hz, 1H), 3.92 (dd, J=10.9, 1.9 Hz, 1H), 3.76 (t, J=9.0 Hz, 1H), 3.73 (dd, J=11.0, 15.8 Hz, 1H), 3.59 (ddd, J=9.9, 5.8, 1.8 Hz, 1H), 3.54 (dd, J=9.7, 8.5 Hz, 1H), 3.46 (dd, J=9.6, 3.6 Hz, 1H), 3.38 (s, 3H), 1.16-1.04 (m, 21H), 0.10 (s, 9H). $^{13}$C NMR (176 MHz, CDCl$_3$) δ 139.1, 138.2, 128.3, 128.2, 128.1, 127.8, 127.4, 127.2, 97.5, 81.9, 80.4, 75.4, 73.2, 72.9, 71.1, 63.0, 54.7, 18.0, 17.9, 12.0, 0.6. ESI-HRMS m/z: Calcd. for C$_{33}$H$_{58}$O$_6$Si$_2$N [M+NH$_4$]$^+$: 620.3803; found: 620.3781.

Methyl-2,3-di-O-benzyl-4-O-trimethylsilyl-6-O-tert-butyldimethylsilyl-α-D-glucopyranoside (27a)

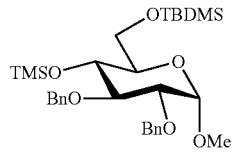

This compound was prepared by following the general experimental procedure (B) using methyl-2,3-di-O-benzyl-6-O-tert-butyldimethylsilyl-α-D-glucopyranoside (500 mg, 1.02 mmol), triethylamine (0.57 mL, 4.09 mmol), and chlorotrimethylsilane (0.26 mL, 2.05 mmol). Purification by column chromatography eluting with ethyl acetate/hexane (1:19 to 1:4) afforded the desired product (480 mg, 0.86 mmol, 84%) as a colorless viscous liquid. $^1$H NMR (700 MHz, CDCl$_3$) δ 7.43-7.19 (m, 10H), 5.00 (d, J=11.1 Hz, 1H), 4.77 (d, J=11.1 Hz, 1H), 4.72 (d, J=12.0 Hz, 1H), 4.61 (d, J=12.0 Hz, 1H), 4.58 (d, J=3.5 Hz, 1H), 3.80 (d, J=11.9 Hz, 1H), 3.77 (t, J=9.1 Hz, 1H), 3.73 (dd, J=11.3, 4.9 Hz, 1H), 3.60 (t, J=9.2 Hz, 1H), 3.54 (dd, J=10.3, 4.6 Hz, 1H), 3.46 (dd, J=9.6, 3.5 Hz, 1H), 3.37 (s, 3H), 0.90 (s, 9H), 0.12 (s, 9H), 0.07 (s, 3H), 0.06 (s, 3H). $^{13}$C NMR (176 MHz, CDCl$_3$) δ 139.1, 138.2, 128.4, 128.2, 128.1, 127.8, 127.5, 127.2, 97.7, 82.0, 80.5, 75.4, 73.3, 72.6, 70.9, 62.4, 54.8, 25.9, 18.4, 0.6, −5.0, −5.3. ESI-HRMS m/z: Calcd. for O$_{31}$H$_{48}$O$_6$Si$_2$Na [M Na]$^+$: 583.2887; found: 583.2874.

Methyl-2-O-benzyl-3-O-trimethylsilyl-4,6-O-benzylidene-α-D-glucopyranoside

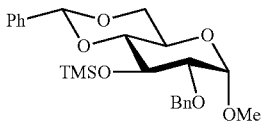

This compound was prepared by following the general experimental procedure (B) using methyl-2-O-benzyl-4,6-O-benzylidene-α-D-glucopyranoside (150 mg, 0.40 mmol), triethylamine (0.22 mL, 1.61 mmol), and chlorotrimethylsilane (0.1 mL, 0.80 mmol). Purification by column chromatography eluting with ethyl acetate/hexane (1:19 to 1:4) afforded the desired product (160 mg, 0.36 mmol, 90%) as a white foam. $^1$H NMR (700 MHz, CDCl$_3$) δ 7.52-7.45 (m, 2H), 7.41-7.33 (m, 7H), 7.30 (t, J=7.2 Hz, 1H), 5.50 (s, 1H), 4.85 (d, J=12.3 Hz, 1H), 4.64 (d, J=12.3 Hz, 1H), 4.53 (d, J=3.7 Hz, 1H), 4.24 (dd, J=10.2, 4.9 Hz, 1H), 4.12 (t, J=9.0 Hz, 1H), 3.78 (td, J=10.0, 4.9 Hz, 1H), 3.68 (t, J=10.3 Hz, 1H), 3.43-3.38 (m, 3H), 3.38 (s, 3H), 0.15 (s, 9H). $^{13}$C NMR (176 MHz, CDCl$_3$) δ 138.4, 137.5, 129.0, 128.6, 128.3 (2C), 128.03, 126.3, 101.8, 99.6, 82.2, 79.9, 74.1, 71.9, 69.2, 62.4, 55.4, 0.7. ESI-HRMS m/z: Calcd. for C$_{24}$H$_{32}$O$_6$SiNa [M+Na]$^+$: 462.1866; found: 462.1865.

Methyl-2-O-trimethylsilyl-3-O-benzyl-4,6-O-benzylidene-α-D-glucopyranoside

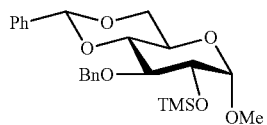

This compound was prepared by following the general experimental procedure (A) using methyl-3-O-benzyl-4,6-O-benzylidene-α-D-glucopyranoside (203 mg, 0.54 mmol), catalytic iodine (6.8 mg, 0.03 mmol), and hexamethyldisilazane (91 μL, 0.44 mmol). Purification by column chromatography eluting with ethyl acetate/hexane (1:19 to 1:4) afforded the desired product (200 mg, 0.45 mmol, 83%) as a white foam. $^1$H NMR (700 MHz, CDCl$_3$) δ 7.5-7.5 (m, 2H), 7.4-7.3 (m, 5H), 7.3-7.3 (m, 2H), 7.3-7.2 (m, 1H), 5.6 (s, 1H), 4.9 (d, J=11.4 Hz, 1H), 4.8 (d, J=11.4 Hz, 1H), 4.6 (d, J=3.7 Hz, 1H), 4.3 (dd, J=10.2, 4.8 Hz, 1H), 3.9-3.8 (m, 2H), 3.8-3.7 (m, 2H), 3.6 (t, J=9.4 Hz, 1H), 3.4 (s, 3H), 0.2 (s, 9H). $^{13}$C NMR (176 MHz, CDCl$_3$) δ 138.9, 137.6, 129.0, 128.3 (2C), 128.1, 127.6, 126.2, 101.4, 101.1, 82.2, 78.9, 75.5, 73.8, 69.3, 62.6, 55.6, 0.5. ESI-HRMS m/z: Calcd. for C$_{24}$H$_{33}$O$_6$Si [M+H]$^+$: 445.2041; found: 445.2042.

Methyl-2,3,6-tri-O-benzyl-4-O-(2-O-trimethylsilyl-3,4,6-tri-O-benzyl-α-D-mannopyranosyl)-α-D-glucopyranoside

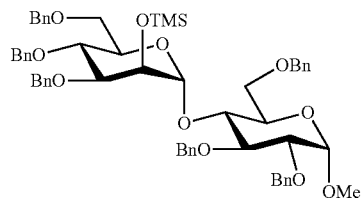

Methyl-2,3,6-tri-O-benzyl-4-O-(2-O-acetyl-3,4,6-tri-O-benzyl-α-D-mannopyranosyl)-α-D-glucopyranoside (1.65 g, 1.76 mmol) was dissolved in anhydrous MeOH. To this rapidly stirring solution was added sodium methoxide (104 mg, 1.93 mmol). After 16 hours, TLC analysis showed full conversion (Rf product=0.2 in 1:3 Ethyl Acetate:Hexanes). Then the reaction mixture was brought to pH=6 using acidic Dowex® 50WX8-200 ion exchange resin, filtered through cotton and concentrated under reduced pressure. This crude reaction mixture was subjected to general procedure B. Purification by column chromatography eluting with ethyl acetate/hexane (1:19 to 1:4) gave the desired product (927 mg, 0.96 mmol) as a colorless oil. $^1$H NMR (700 MHz, CDCl$_3$) δ 7.35-7.16 (m, 30H), 5.08 (d, J=2.3 Hz, 1H), 5.04 (d, J=11.4 Hz, 1H), 4.79 (d, J=10.9 Hz, 1H), 4.69 (m, 2H), 4.62 (d, J=12.1 Hz, 1H), 4.61-4.54 (m, 5H), 4.47 (d, J=10.9 Hz, 1H), 4.43 (m, 2H), 4.00 (t, J=2.5 Hz, 1H), 3.88 (t, J=9.2 Hz, 1H), 3.85-3.68 (m, 7H), 3.66 (dd, J=10.9, 5.0 Hz, 1H), 3.58 (dd, J=10.9, 1.9 Hz, 1H), 3.53 (dd, J=9.7, 3.5 Hz, 1H), 3.38 (s, 3H), −0.04 (s, 9H). $^{13}$C NMR (176 MHz, CDCl$_3$) δ

138.8, 138.6, 138.5, 138.4 (2C), 138.0, 128.4 (2C), 128.3 (2C), 128.2 (2C), 128.1, 127.9 (2C), 127.8, 127.7 (2C), 127.6, 127.5 (2C), 127.4, 127.3, 126.8, 103.2, 97.8, 81.2, 79.7, 79.7, 78.2, 75.1, 74.8, 74.7, 73.3 (2C), 73.2 (2C), 72.5, 70.2, 70.0, 69.5, 69.3, 55.2, 0.3. ESI-HRMS m/z: Calcd. for $C_{58}H_{72}O_{11}SiN$ $[M+NH_4]^+$: 986.4869; found: 986.4860.

Methyl-2,3,4-tri-O-benzyl-6-O-trimethylsilyl-α-D-glucopyranoside

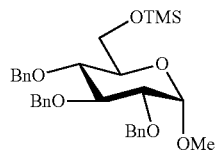

This compound was prepared by following the general experimental procedure (B) using methyl-2,3,4-tri-O-benzyl-α-D-glucopyranoside (150 mg, 0.40 mmol), triethylamine (0.36 mL, 2.58 mmol), and chlorotrimethylsilane (0.16 mL, 1.29 mmol). Purification by column chromatography eluting with ethyl acetate/hexane (1:19 to 1:4) afforded the desired product (310 mg, 0.58 mmol, 89%) as a colorless viscous liquid.

4-Penten-1-yl-2,3,6-O-tri-benzyl-4-O-trimethylsilyl-β-D-glucopyranoside

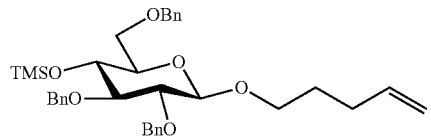

This compound was prepared by following the general experimental procedure (B) using 4-penten-1-yl-2,3,6-tri-O-benzyl-β-D-glucopyranoside (300 mg, 0.58 mmol), triethylamine (0.24 mL, 1.74 mmol) and chlorotrimethylsilane (0.1 mL, 0.87 mmol). Purification by column chromatography eluting with ethyl acetate/hexane (1:19 to 1:4) afforded the desired product (309 mg, 0.52 mmol, 90%) as a colorless viscous liquid. $^1$H NMR (700 MHz, CDCl$_3$) δ 7.37-7.22 (m, 15H), 5.82 (ddt, J=17.0, 10.2, 6.6 Hz, 1H), 5.04-5.00 (m, 1H), 4.98-4.95 (m, 2H), 4.92 (d, J=10.9 Hz, 1H), 4.72 (d, J=11.3 Hz, 1H), 4.66-4.62 (m, 2H), 4.57 (d, J=12.2 Hz, 1H), 4.42-4.38 (m, 1H), 3.96 (dt, J=9.6, 6.5 Hz, 1H), 3.72 (dd, J=10.8, 1.9 Hz, 1H), 3.65-3.54 (m, 3H), 3.45-3.37 (m, 3H), 2.21-2.12 (m, 2H), 1.80-1.70 (m, 2H), 0.04 (s, 9H). $^{13}$C NMR (176 MHz, CDCl$_3$) δ 139.0, 138.6, 138.5, 138.2, 128.5 (2C), 128.3 (2C), 127.8, 127.7 (2C), 127.3 (2C), 115.0, 103.9, 84.8, 82.6, 76.2, 75.4, 74.9, 73.6, 71.5, 69.5, 69.4, 30.4, 29.2, 0.7. ESI-HRMS m/z: Calcd. for $C_{35}H_{50}O_6SiN$ $[M+NH_4]^+$: 608.3402; found: 608.3390.

Synthesis of 4-penten-1-yl-2-O-acetyl-3-O-benzyl-4-O-trimethylsilyl-6-O-tert-butyldimethylsilyl-β-D-glucopyranoside (27b)

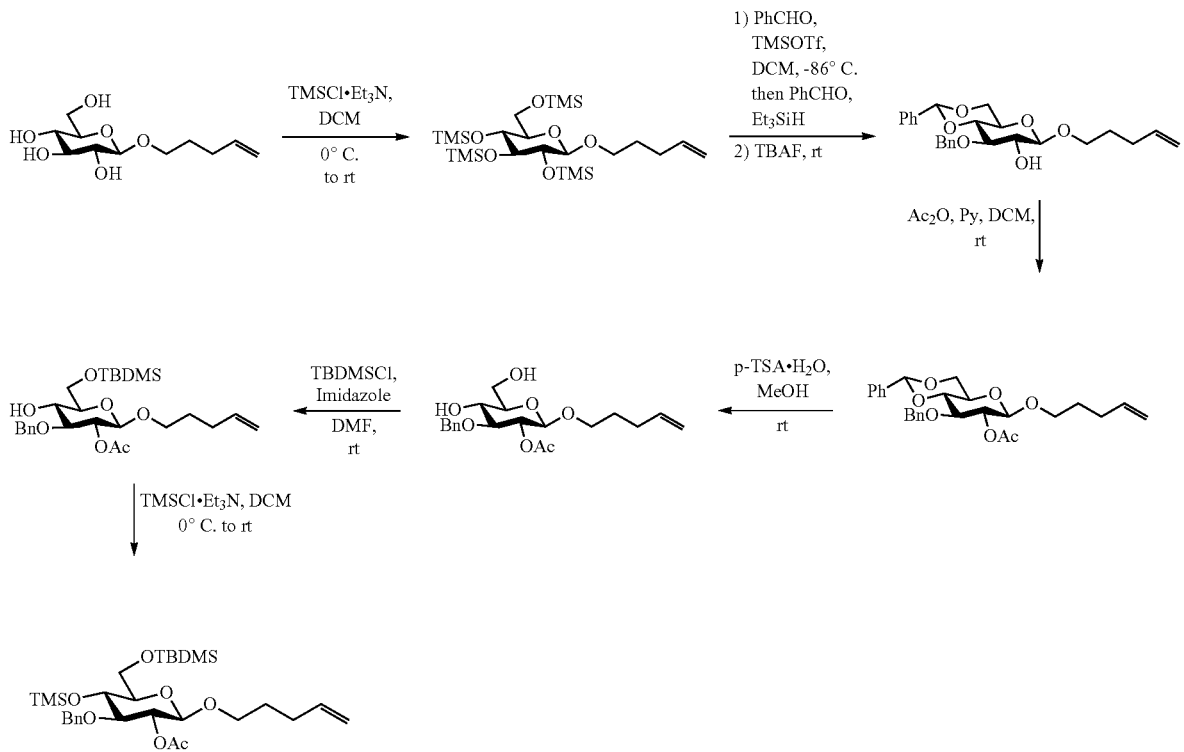

4-Penten-1-yl-2,3,4,6-tetra-O-trimethylsilyl-β-D-glucopyranoside

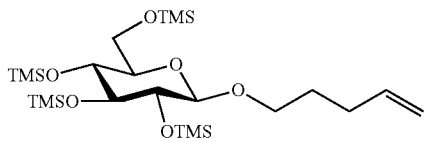

According to an adapted procedure from the literature (Wang et al., *Nat. Protoc.* 2008, 3, 97), a stirred solution of 4-penten-1-yl-β-D-glucopyranoside (2.09 g, 8.40 mmol) in dichloromethane (60 mL) was treated with triethylamine (9.4 mL, 67.2 mmol) and chlorotrimethylsilane (7.5 mL, 58.8 mmol) at 0° C. The reaction mixture was allowed to warm to rt and stirring was continued overnight before it was concentrated to dryness under reduced pressure. The residue was dissolved in dichloromethane (100 mL), and dichloromethane layer was washed with aq. NaHCO$_3$ (2×100 mL), dried over anhydrous Na$_2$SO$_4$, and concentrated under reduced pressure to yield the desired product (4.03 g, 7.98 mmol, 95%) as a light-yellow viscous liquid. $^1$H NMR (700 MHz, CDCl$_3$) δ 5.81 (ddt, J=17.1, 10.3, 6.7 Hz, 1H), 5.04-4.99 (m, 1H), 4.96-4.93 (m, 1H), 4.15 (d, J=7.5 Hz, 1H), 3.83 (dt, J=9.4, 7.1 Hz, 1H), 3.79 (dd, J=11.4, 2.0 Hz, 1H), 3.68 (dd, J=11.3, 5.2 Hz, 1H), 3.49-3.40 (m, 3H), 3.28 (t, J=7.8 Hz, 1H), 3.18-3.14 (ddd, J=8.8, 5.2, 1.9 Hz, 1H), 2.17-2.05 (m, 2H), 1.77-1.66 (m, 2H), 0.16 (s, 9H), 0.15 (s, 9H), 0.14 (s, 9H), 0.11 (s, 9H). $^{13}$C NMR (176 MHz, CDCl$_3$) δ 138.4, 114.8, 103.1, 78.8, 76.7, 76.2, 71.8, 68.9, 62.4, 30.5, 29.1, 1.5, 1.4, 1.0, −0.1. ESI-HRMS m/z: Calcd. for C$_{23}$H$_{52}$O$_6$Na [M+Na]$^+$: 559.2733; found: 559.2726.

4-Penten-1-yl-3-O-benzyl-4,6-O-benzylidene-β-D-glucopyranoside

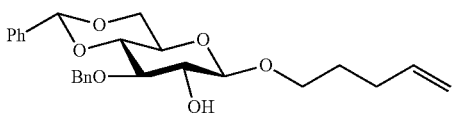

According to an adapted procedure from the literature (Wang et al., *Nat. Protoc.* 2008, 3, 97; Wang et al., *Nature* 2007, 446, 896), a prestirred mixture of 4-penten-1-yl-2,3,4,6-tetra-O-trimethylsilyl-β-D-glucopyranoside (2.0 g, 3.73 mmol), benzaldehyde (0.4 mL, 3.92 mmol) and freshly activated 4 Å molecular sieves (3.5 g) in dichloromethane (28 mL) was treated with trimethylsilyl trifluoromethanesulfonate (0.1 mL, 0.56 mmol) was added to at −86° C. under nitrogen atmosphere. After stirring for 4 h at −86° C., triethylsilane (0.66 mL, 4.10 mmol), benzaldehyde (0.46 mL, 4.48 mmol) and trimethylsilyl trifluoromethanesulfonate (0.05 mL, 0.28 mmol) were added to the solution in sequence, and the mixture was stirred overnight at −86° C. Then to the reaction mixture was added tetrabutylammonium fluoride (7.5 mL, 7.46 mmol) and the reaction was gradually warmed up to rt, and stirring was continued overnight at rt. The mixture was then filtered through a pad of celite and the filtrate was concentrated under reduced pressure. The residue was dissolved in ethyl acetate (50 mL) and ethyl acetate layer was washed with aq. NaHCO$_3$ (2×100 mL) and water (100 mL), dried over anhydrous Na$_2$SO$_4$, and concentrated under reduced pressure. Purification by column chromatography eluting with ethyl acetate/hexane (1:19 to 1:4) afforded the desired product (921 mg, 2.16 mmol, 58%) as a white foam. $^1$H-NMR (700 MHz, CDCl$_3$): δ 7.51-7.48 (m, 2H), 7.41-7.27 (m, 8H), 5.82 (ddt, J=17.0, 10.3, 6.7 Hz, 1H), 5.57 (s, 1H), 5.06-5.02 (m, 1H), 5.00-4.95 (m, 2H), 4.81 (d, J=11.7 Hz, 1H), 4.39 (d, J=7.8 Hz, 1H), 4.35 (dd, J=10.5, 4.9 Hz, 1H), 3.91 (dt, J=9.5, 6.5 Hz, 1H), 3.80 (t, J=10.3 Hz, 1H), 3.69 (dt, J=27.3, 9.1 Hz, 2H), 3.60-3.55 (m, 2H), 3.44 (dt, J=9.6, 4.9 Hz, 1H), 2.43-2.42 (m, 1H), 2.19-2.12 (m, 2H), 1.80-1.70 (m, 2H). $^{13}$C NMR (700 MHz, CDCl$_3$) δ 138.5, 138.1, 137.4, 129.1, 128.6, 128.4, 128.2, 127.9, 126.2, 115.2, 103.5, 101.4, 81.5, 80.4, 74.7, 74.5, 69.9, 68.9, 66.6, 30.3, 28.9. ESI-HRMS m/z: Calcd. for C$_{25}$H$_{30}$O$_6$Na [M+Na]$^+$: 449.1934; found: 449.1924.

4-Penten-1-yl-2-O-acetyl-3-O-benzyl-4,6-O-benzylidene-β-D-glucopyranoside

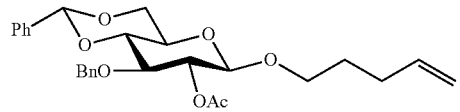

To a stirred solution of 4-penten-1-yl-3-O-benzyl-4,6-O-benzylidene-β-D-glucopyranoside (900 mg, 2.11 mmol) in dichloromethane (20 mL) was added pyridine (0.51 mL, 6.33 mmol) followed by addition of acetic anhydride (0.4 mL, 4.22 mmol) at rt and stirring was continued overnight at rt. Then the reaction mixture was diluted with ethyl acetate (50 mL) and ethyl acetate layer was washed with 0.1 M HCl (50 mL), aq. NaHCO$_3$ (50 mL), and brine (50 mL), dried over anhydrous Na$_2$SO$_4$ and concentrated under reduced pressure. Purification by column chromatography eluting with ethyl acetate/hexane (1:19 to 1:4) afforded the desired product (935 mg, 2.0 mmol, 95%) as a white foam. $^1$H NMR (700 MHz, CDCl$_3$) δ 7.52-7.49 (m, 2H), 7.42-7.27 (m, 8H), 5.79 (ddt, J=16.8, 10.4, 6.7 Hz, 1H), 5.58 (s, 1H), 5.04-4.95 (m, 3H), 4.88 (d, J=12.1 Hz, 1H), 4.68 (d, J=12.1 Hz, 1H), 4.45 (d, J=8.0, 1H), 4.36 (dd, J=10.6, 5.0 Hz, 1H), 3.86 (dt, J=9.7, 6.1 Hz, 1H), 3.84-3.70 (m, 3H), 3.51-3.41 (m, 2H), 2.13-2.04 (m, 2H), 2.01 (s, 3H), 1.72-1.59 (m, 2H). $^{13}$C NMR (176 MHz, CDCl$_3$) δ 169.4, 138.4, 138.0, 137.3, 129.2, 128.5, 128.4 (2C), 128.0, 127.8, 126.1, 115.2, 101.8, 101.4, 81.8, 78.6, 74.2, 73.0, 69.4, 68.9, 66.4, 30.0, 28.8, 21.0. ESI-HRMS m/z: Calcd. for C$_{27}$H$_{32}$O$_7$Na [M+Na]$^+$: 491.2040; found: 491.2028.

4-Penten-1-yl-2-O-acetyl-3-O-benzyl-β-D-glucopyranoside

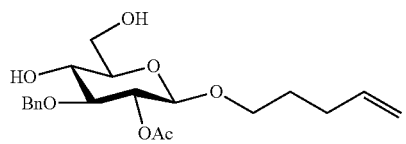

A stirred solution of 4-penten-1-yl-2-O-acetyl-3-O-benzyl-4,6-O-benzylidene-β-D-glucopyranoside (915 mg, 1.95 mmol) in methanol (15 mL) was treated with p-toluenesulfonic acid monohydrate (38 mg, 0.20 mmol) at rt. The reaction mixture was stirred for 6 h at rt before it was concentrated under reduced pressure. The residue was dissolved in ethyl acetate (50 mL) and ethyl acetate layer was washed with aq. NaHCO$_3$ (2×100 mL) and water (100 mL), dried over anhydrous Na$_2$SO$_4$, and concentrated under reduced pressure to yield the desired product (500 mg, 1.33 mmol, 68%) as an off-white solid. $^1$H NMR (700 MHz, CDCl$_3$) δ 7.39-7.28 (m, 5H), 5.79 (ddt, J=17.0, 10.4, 6.6 Hz, 1H), 5.03-4.95 (m, 3H), 4.76 (d, J=11.7 Hz, 1H), 4.65 (d, J=11.7 Hz, 1H), 4.41 (d, J=8.0 Hz, 1H), 3.91-3.84 (m, 2H), 3.81-3.76 (m, 1H), 3.68 (t, J=9.5 Hz, 1H), 3.53 (t, J=9.3 Hz, 1H), 3.49-3.45 (m, 1H), 3.37 (ddd, J=9.6, 5.0, 3.6 Hz, 1H), 2.38 (br s, 1H), 2.14-2.05 (m, 2H), 2.04 (s, 3H), 1.72-1.60 (m, 2H), 1.58 (br s, 1H). $^{13}$C NMR (176 MHz, CDCl$_3$) δ 169.6, 138.2, 138.0, 128.8, 128.2, 128.0, 115.2, 101.4, 82.8, 75.3, 74.6, 73.2, 70.6, 69.3, 62.7, 30.0, 28.8, 21.1. ESI-HRMS m/z: Calcd. for C$_{20}$H$_{28}$O$_7$Na [M+Na]$^+$: 403.1727; found: 403.1729.

4-Penten-1-yl-2-O-acetyl-3-O-benzyl-6-O-tert-butyldimethylsilyl-β-D-glucopyranoside

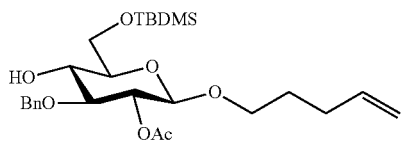

A stirred solution of 4-penten-1-yl-2-O-acetyl-3-O-benzyl-β-D-glucopyranoside (250 mg, 0.66 mmol) in N,N-dimethylformamide (4.0 mL) was treated with imidazole (134 mg, 1.97 mmol) and tert-butyldimethylsilyl chloride (119 mg, 0.79 mmol), and the stirring was continued overnight at rt. Then the reaction mixture was diluted with ethyl acetate (25 mL), and ethyl acetate layer was washed with water (2×25 mL) and brine (25 mL), dried over anhydrous Na$_2$SO$_4$, and concentrated under reduced pressure. Purification by column chromatography eluting with ethyl acetate/hexane (1:99 to 1:4) afforded the desired product δ (255 mg, 0.52 mmol, 79%) as a light-yellow viscous liquid. $^1$H NMR (700 MHz, CDCl$_3$) δ 7.36-7.26 (m, 5H), 5.78 (ddt, J=17.0, 10.3, 6.6 Hz, 1H), 5.02-4.91 (m, 3H), 4.80 (d, J=11.7 Hz, 1H), 4.72 (d, J=11.7 Hz, 1H), 4.36 (d, J=8.0 Hz, 1H), 3.92 (dd, J=10.5, 5.0 Hz, 1H), 3.85-3.80 (m, 2H), 3.75 (td, J=9.1, 1.7 Hz, 1H), 3.53 (t, J=9.2 Hz, 1H), 3.44 (td, J=9.7, 6.8 Hz, 1H), 3.35 (td, J=9.5, 5.3 Hz, 1H), 3.13 (s, 1H), 2.12-2.02 (m, 2H), 2.00 (s, 3H), 1.71-1.58 (m, 2H), 0.90 (s, 9H), 0.10 (s, 3H), 0.09 (s, 3H). $^{13}$C NMR (176 MHz, CDCl$_3$) δ 169.6, 138.6, 138.2, 128.6, 128.0, 127.9, 115.1, 101.1, 82.5, 74.5, 74.3, 73.6, 72.8, 68.9, 64.9, 30.1, 28.8, 26.0, 21.1, 18.4, −5.3 (2C). ESI-HRMS m/z: Calcd. for C$_{26}$H$_{42}$O$_7$SiNa [M+Na]$^+$: 517.2592; found: 517.2580.

4-Penten-1-yl-2-O-acetyl-3-O-benzyl-4-O-trimethylsilyl-6-O-tert-butyldimethylsilyl-β-D-glucopyranoside (27b)

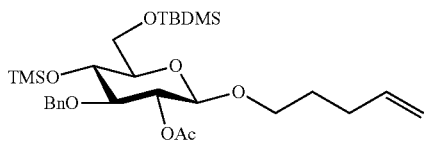

A stirred solution of 4-penten-1-yl-2-O-acetyl-3-O-benzyl-6-O-tert-butyldimethylsilyl-β-D-glucopyranoside (250 mg, 0.50 mmol) in dichloromethane (4.0 mL) was treated with triethylamine (0.2 mL, 1.5 mmol) and chlorotrimethylsilane (0.1 mL, 0.76 mmol) at 0° C. The reaction mixture was allowed to warm to rt and stirring was continued for 3 h before it was concentrated to dryness under reduced pressure. The residue was dissolved in dichloromethane (50 mL), and dichloromethane layer was washed with aq. NaHCO$_3$ (2×100 mL) and water (100 mL), dried over anhydrous Na$_2$SO$_4$, and concentrated under reduced pressure to yield the desired product (260 mg, 0.46 mmol, 92%) as a light-yellow viscous liquid. $^1$H NMR (700 MHz, CDCl$_3$) δ 7.35-7.26 (m, 5H), 5.78 (ddt, J=17.0, 10.3, 6.6 Hz, 1H), 5.03-4.92 (m, 2H), 4.89 (dd, J=9.5, 8.1 Hz, 1H), 4.76 (d, J=11.6 Hz, 1H), 4.61 (d, J=11.6 Hz, 1H), 4.33 (d, J=8.0 Hz, 1H), 3.87-3.72 (m, 4H), 3.47-3.40 (m, 2H), 3.19 (ddd, J=9.4, 4.0, 2.0 Hz, 1H), 2.07 (m, 2H), 1.88 (s, 3H), 1.69-1.58 (m, 2H), 0.90 (s, 9H), 0.13 (s, 9H), 0.07 (s, 3H), 0.06 (s, 3H). $^{13}$C NMR (176 MHz, CDCl$_3$) δ 169.7, 138.6, 138.3, 128.5, 127.7, 127.6, 114.9, 100.9, 83.7, 77.1, 75.5, 73.4, 70.8, 68.3, 62.0, 30.2, 28.9, 26.1, 21.0, 18.6, 0.7, −4.8, −5.3. ESI-HRMS m/z: Calcd. for C$_{29}$H$_{50}$O$_7$Si$_2$Na [M+Na]$^+$: 589.2987; found: 589.2979.

Synthesis of 2-O-acetyl-3-O-benzyl-4-O-triethylsilyl-6-O-triisopropylsilyl-α-D-mannopyranosyl fluoride (29a), 2-O-acetyl-3-O-benzyl-4-O-tri-n-butylsilyl-6-O-triisopropylsilyl-α-D-mannopyranosyl fluoride (29b), and 2-O-acetyl-3-O-benzyl-4-O-triethylsilyl-6-O-benzoyl-α-D-mannopyranosyl fluoride

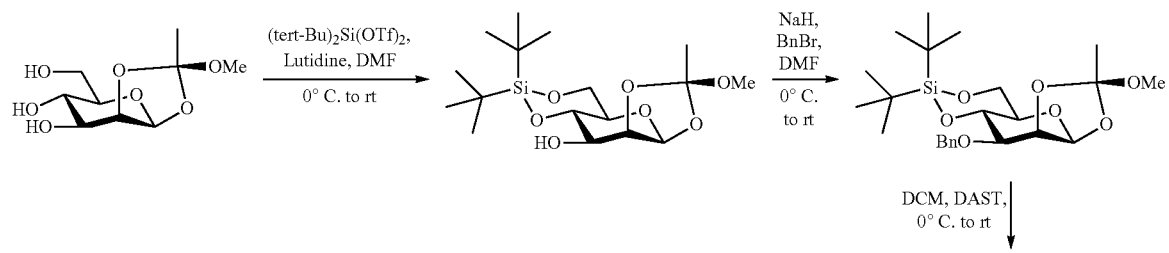

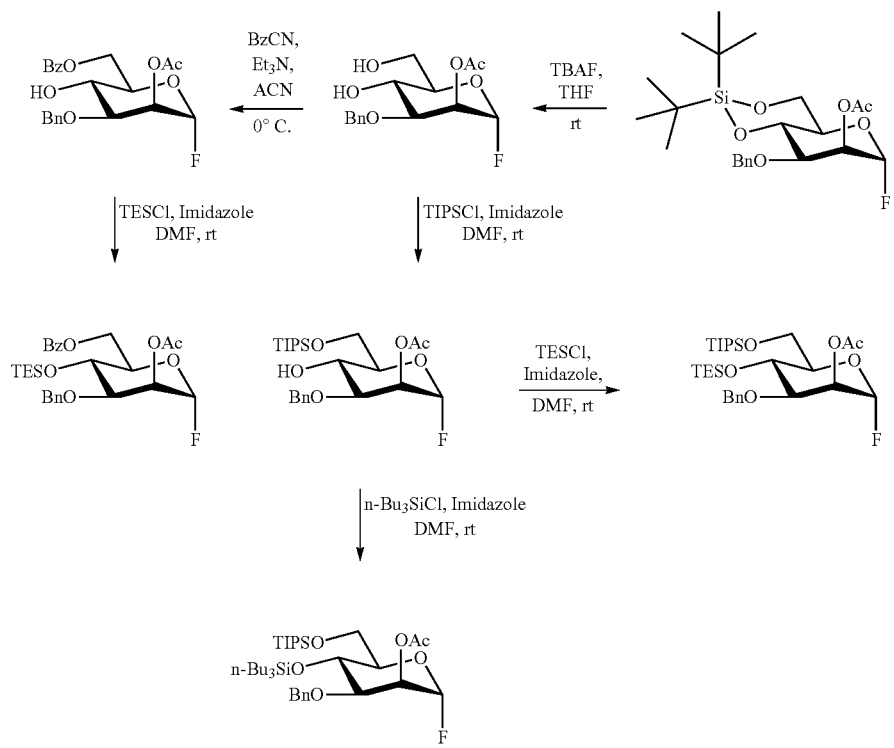

1,2-O-(exo-Methoxyethylidene)-4,6-O-di-tert-butyl-silylene-β-D-mannopyranoside

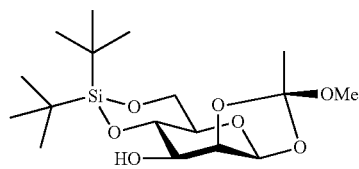

A stirred solution of 1,2-O-(exo-methoxyethylidene)-β-D-mannopyranoside (4.5 g, 19.06 mmol) in N,N-dimethylformamide (90 mL) was treated with 2,6-lutidine (6.6 mL, 57.18 mmol) and di-tert-butylsilyl bis(trifluoromethanesulfonate) (6.8 mL, 20.97 mmol) at 0° C. The reaction mixture was allowed to warm to rt and stirring was continued overnight. Then the reaction mixture was diluted with ethyl acetate (300 mL) and ethyl acetate layer was washed with water (2×200 mL) and brine (200 ml), dried over anhydrous Na$_2$SO$_4$, and concentrated under reduced pressure. Purification by column chromatography eluting with ethyl acetate/hexane (1:19 to 1:3) afforded the desired product (5 g, 13.29 mmol, 70%) as a white foam. $^1$H NMR (700 MHz, CDCl$_3$) δ 5.43 (d, J=2.3 Hz, 1H), 4.55 (dd, J=4.2, 2.3 Hz, 1H), 4.15 (dd, J=10.4, 5.0 Hz, 1H), 3.96 (t, J=9.3 Hz, 1H), 3.86 (t, J=10.2 Hz, 1H), 3.80-3.55 (m, 1H), 3.34-3.28 (m, 1H), 3.31 (s, 3H), 2.78 (d, J=4.0 Hz, 1H), 1.66 (s, 3H), 1.05 (s, 9H), 0.97 (s, 9H). $^{13}$C NMR (176 MHz, CDCl$_3$) δ 124.3, 97.5, 78.7, 74.3, 72.8, 69.0, 66.0, 49.8, 27.4, 26.9, 24.7, 22.7, 19.8.

1,2-O-(exo-Methoxyethylidene)-3-O-benzyl-4,6-O-di-tert-butylsilylene-β-D-mannopyranoside

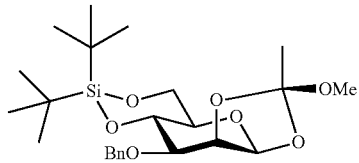

To a stirred solution of 1,2-O-(exo-methoxyethylidene)-4,6-O-di-tert-butylsilylene-β-D-mannopyranoside (5 g, 13.29 mmol) in N,N-dimethylformamide (50 mL) was added sodium hydride (60% suspension in mineral oil, 638 mg, 15.95 mmol) portion-wise at 0° C. The reaction mixture was stirred for 15 minutes at 0° C. before benzyl bromide (2.4 mL, 19.94 mmol) was added to it. The reaction mixture was allowed to warm to rt and stirring was continued for 1.5 h at rt. Then the reaction mixture was diluted with ethyl acetate (300 mL) and ethyl acetate layer was washed with water (2×200 mL) and brine (200 ml), dried over anhydrous Na$_2$SO$_4$, and concentrated under reduced pressure. Purification by column chromatography eluting with ethyl acetate/hexane (1:19 to 1:5) afforded the desired product (5.2 g, 11.15 mmol, 84%) as a white foam. $^1$H NMR (700 MHz, CDCl$_3$) δ 7.42 (d, J=7.5 Hz, 2H), 7.35 (t, J=7.5 Hz, 2H), 7.30 (t, J=7.5 Hz, 1H), 5.30 (d, J=2.2 Hz, 1H), 4.97 (d, J=12.7 Hz, 1H), 4.90 (d, J=12.7 Hz, 1H), 4.38 (dd, J=4.2, 2.2 Hz, 1H), 4.23 (t, J=9.3 Hz, 1H), 4.14 (dd, J=10.4, 4.9 Hz, 1H), 3.89 (t, J=10.2 Hz, 1H), 3.57 (dd, J=9.1, 4.1 Hz, 1H), 3.31 (s, 3H), 3.27 (td, J=9.8, 5.1 Hz, 1H), 1.67 (s, 3H), 1.10 (s, 9H), 1.00 (s, 9H). $^{13}$C NMR (176 MHz, CDCl$_3$) δ 138.3, 128.4, 127.8

(2C), 124.1, 97.6, 78.4, 77.3, 74.6, 73.2, 69.2, 66.2, 50.0, 27.4, 27.0, 24.4, 22.7, 19.9. ESI-HRMS m/z: Calcd. for $C_{24}H_{38}O_7SiNa$ [M+Na]$^+$: 489.2284; found: 489.2277.

2-O-Acetyl-3-O-benzyl-4,6-O-di-tert-butylsilylene-α-D-mannopyranosyl fluoride

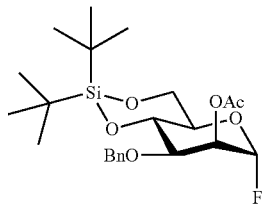

A stirred solution of 1,2-O-(exo-methoxyethylidene)-3-O-benzyl-4,6-O-di-tert-butylsilylene-β-D-mannopyranoside (1 g, 2.14 mmol) in dichloromethane (10 mL) was treated with diethylaminosulfur trifluoride (0.34 mL, 2.57 mmol) at 0° C. The reaction mixture was allowed to warm to rt and stirring was continued for 2 hours at rt before it was quenched with aq. NaHCO$_3$ (50 mL). Then the aqueous layer was extracted with dichloromethane (2×50 mL) and dichloromethane layer was washed with water (50 mL), dried over anhydrous Na$_2$SO$_4$, and concentrated under reduced pressure. Purification by column chromatography eluting with ethyl acetate/hexane (1:19 to 1:5) afforded the desired product (800 mg, 1.76 mmol, 82%) as a colorless viscous liquid. $^1$H NMR (700 MHz, CDCl$_3$) δ 7.38 (d, J=7.4 Hz, 2H), 7.33 (t, J=7.5 Hz, 2H), 7.28 (t, J=7.4 Hz, 1H), 5.46 (dd, J=48.7, 1.8 Hz, 1H), 5.41-5.39 (m, 1H), 4.77 (s, 2H), 4.23 (t, J=9.6 Hz, 1H), 4.16 (dd, J=10.0, 4.8 Hz, 1H), 3.96 (t, J=10.3 Hz, 1H), 3.87 (td, J=10.0, 4.8 Hz, 1H), 3.75 (ddd, J=9.6, 3.7, 1.7 Hz, 1H), 2.15 (s, 3H), 1.10 (s, 9H), 1.00 (s, 9H). $^{13}$C NMR (176 MHz, CDCl$_3$) δ 170.0, 138.2, 128.3, 127.6, 127.4, 105.6 (d, J=221.9 Hz), 75.3 (d, J=2.3 Hz), 73.8, 72.7, 69.6 (d, J=2.3 Hz), 68.2 (d, J=40.6 Hz), 66.1, 27.4, 27.0, 22.7, 20.9, 19.9. $^{19}$F NMR (377 MHz, CDCl$_3$) δ −137.0 (d, J=49.0 Hz).

2-O-Acetyl-3-O-benzyl-α-D-mannopyranosyl fluoride

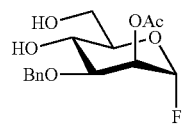

A stirred solution of 2-O-acetyl-3-O-benzyl-4,6-O-di-tert-butylsilylene-α-D-mannopyranosyl fluoride (750 mg, 1.65 mmol) in tetrahydrofuran (7.5 mL) was treated with tetrabutylammonium fluoride (1M in tetrahydrofuran, 6.6 mL, 6.6 mmol) in the presence of glacial acetic acid (0.47 mL, 8.25 mmol) at rt and stirring was continued for 3 h at rt. Then the reaction mixture was diluted with ethyl acetate (150 mL) and ethyl acetate layer was washed with water (2×100 mL) and brine (100 ml), dried over anhydrous Na$_2$SO$_4$, and concentrated under reduced pressure. Purification by column chromatography eluting with ethyl acetate/hexane (1:9 to 3:1) afforded the desired product (450 mg, 1.4 mmol, 87%) as a white foam. $^1$H NMR (700 MHz, CDCl$_3$) δ 7.38-7.34 (m, 2H), 7.34-7.30 (m, 3H), 5.58 (dd, J=48.9, 1.9 Hz, 1H), 5.47 (br s, 1H), 4.73 (d, J=11.2 Hz, 1H), 4.47 (d, J=11.2 Hz, 1H), 3.97 (td, J=9.7, 1.9 Hz, 1H), 3.92-3.81 (m, 3H), 3.78 (ddd, J=9.6, 3.4, 2.0 Hz, 1H), 2.62 (d, J=2.6 Hz, 1H), 2.13 (s, 3H), 2.06 (d, J=6.5 Hz, 1H). $^{13}$C NMR (176 MHz, CDCl$_3$) δ 169.9, 137.1, 128.7, 128.3, 128.2, 105.6 (d, J=221.4 Hz), 76.6 (d, J=1.9 Hz), 74.5 (d, J=1.8 Hz), 71.8, 66.2 (d, J=39.8 Hz), 65.8, 61.9, 20.7. $^{19}$F NMR (377 MHz, CDCl$_3$) δ −136.3 (d, J=48.8 Hz). ESI-HRMS m/z: Calcd. for $C_{15}H_{19}O_9FNa$ [M+Na]$^+$: 337.1063; found: 337.1055.

2-O-Acetyl-3-O-benzyl-6-O-benzoyl-α-D-mannopyranosyl fluoride

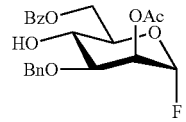

To a stirred solution of 2-O-acetyl-3-O-benzyl-α-D-mannopyranosyl fluoride (150 mg, 0.48 mmol) in acetonitrile (5 mL) was added triethylamine (0.2 mL, 1.43 mmol) followed by dropwise addition of a solution of benzoyl cyanide (66 mg, 0.50 mmol) in acetonitrile (1 mL) at 0° C., and stirring was continued for 2 h at 0° C. Then the reaction mixture was quenched with the excess of methanol (2 mL) at 0° C. and concentrated under reduced pressure. Purification by column chromatography eluting with ethyl acetate/hexane (1:99 to 1:9) afforded the desired product (165 mg, 0.39 mmol, 83%) as a white foam. $^1$H NMR (700 MHz, CDCl$_3$) δ 8.07 (d, J=7.4 Hz, 2H), 7.57 (t, J=7.3, 1H), 7.44 (t, J=7.8 Hz, 2H), 7.38-7.30 (m, 5H), 5.60 (dd, J=48.8, 2.0 Hz, 1H), 5.47 (br s, 1H), 4.75 (d, J=11.2 Hz, 1H), 4.69 (dd, J=12.2, 4.4 Hz, 1H), 4.62 (dd, J=12.2, 2.2 Hz, 1H), 4.52 (d, J=11.2 Hz, 1H), 4.08 (ddd, J=10.1, 4.5, 2.1 Hz, 1H), 3.99 (td, J=9.7, 2.7 Hz, 1H), 3.84 (ddd, J=9.6, 3.3, 2.0 Hz, 1H), 2.69 (d, J=2.8 Hz, 1H), 2.09 (s, 3H). $^{13}$C NMR (176 MHz, CDCl$_3$) δ 169.9, 166.8, 137.3, 133.4, 129.9 (2C), 128.8, 128.5, 128.4, 128.3, 105.6 (d, J=221.3 Hz), 76.4 (d, J=1.2 Hz), 73.2 (d, J=2.0 Hz), 73.2, 72.2, 66.4 (d, J=39.5 Hz), 66.3, 65.7, 63.2, 20.8. ESI-HRMS m/z: Calcd. for $C_{22}H_{23}O_7FNa$ [M+Na]$^+$: 441.1320; found: 441.1315.

2-O-Acetyl-3-O-benzyl-4-O-triethylsilyl-6-O-benzoyl-α-D-mannopyranosyl fluoride (29a)

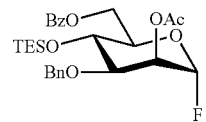

A stirred solution of 2-O-acetyl-3-O-benzyl-6-O-benzoyl-α-D-mannopyranosyl fluoride (200 mg, 0.0.36 mmol) in N,N-dimethylformamide (1.5 mL) was treated with imidazole (98 mg, 1.44 mmol) and chlorotriethylsilane (0.12 mL, 0.72 mmol) at rt and stirring was continued for 3 h at rt. Then the reaction mixture was diluted with ethyl acetate (50 mL) and ethyl acetate layer was washed with water (2×50 mL) and brine (50 ml), dried over anhydrous Na$_2$SO$_4$, and concentrated under reduced pressure. Purification by column chromatography eluting with ethyl acetate/hexane (1:99 to 1:15) afforded the desired product (170 mg, 0.32 mmol, 89%) as a colorless viscous liquid. $^1$H NMR (700 MHz, CDCl$_3$) δ 8.08 (d, J=7.2 Hz, 2H), 7.57 (t, J=7.4 Hz, 1H), 7.45 (t, J=7.8 Hz, 2H), 7.36-7.27 (m, 5H), 5.57 (dd, J=49.3, 2.1 Hz, 1H), 5.45 (dd, J=3.2, 2.1 Hz, 1H), 4.71 (dd, J=12.0, 2.1 Hz, 1H), 4.70 (d, J=11.0 Hz, 1H), 4.49 (d, J=11.1 Hz, 1H), 4.47 (dd, J=11.9, 4.5 Hz, 1H), 4.17 (t, J=9.4 Hz, 1H), 4.07 (ddd, J=9.8, 4.6, 2.0 Hz, 1H), 3.80 (ddd, J=9.2, 3.1, 2.0 Hz, 1H), 2.11 (s, 3H), 0.89 (t, J=7.9 Hz, 9H), 0.67-0.51 (m, 6H). $^{13}$C NMR (176 MHz, CDCl$_3$) δ 169.7, 166.2, 137.4, 133.1, 130.0, 129.6, 128.3, 128.2, 127.8, 127.7, 105.3 (d, J=221.0 Hz), 77.1 (d, J=1.3 Hz), 73.8 (d, J=2.3 Hz), 71.5, 66.9, 66.5 (d, J=39.6 Hz), 63.1, 20.6, 6.8, 5.0. $^{19}$F NMR (377 MHz, CDCl$_3$) δ −137.5 (d, J=49.0 Hz). ESI-HRMS m/z: Calcd. for C$_{28}$H$_{37}$O$_7$FSiNa [M+Na]$^+$: 555.2190; found: 555.2183.

2-O-Acetyl-3-O-benzyl-6-O-triisopropylsilyl-α-D-mannopyranosyl fluoride

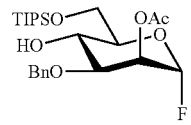

A stirred solution of 2-O-acetyl-3-O-benzyl-α-D-mannopyranosyl fluoride (300 mg, 0.95 mmol) in N,N-dimethylformamide (3 mL) was treated with imidazole (195 mg, 2.86 mmol) and triisopropylsilyl chloride (0.24 mL, 1.15 mmol) at rt and stirring was continued overnight at rt. Then the reaction mixture was diluted with ethyl acetate (50 mL) and ethyl acetate layer was washed with water (2×50 mL) and brine (50 ml), dried over anhydrous Na$_2$SO$_4$, and concentrated under reduced pressure. Purification by column chromatography eluting with ethyl acetate/hexane (1:19 to 1:7) afforded the desired product (410 mg, 0.87 mmol, 91%) as a colorless viscous liquid. $^1$H NMR (700 MHz, CDCl$_3$) δ 7.38-7.27 (m, 5H), 5.56 (dd, J=49.3, 2.0 Hz, 1H), 5.43-5.40 (m, 1H), 4.73 (d, J=11.3 Hz, 1H), 4.54 (d, =11.3 Hz, 1H), 4.12 (t, J=9.6 Hz, 1H), 4.04 (dd, J=10.8, 3.7 Hz, 1H), 3.93 (dd, J=10.8, 4.1 Hz, 1H), 3.82-3.70 (m, 2H), 2.82 (br s, 1H), 2.09 (s, 3H), 1.17-1.01 (m, 21H). $^{13}$C NMR (176 MHz, CDCl$_3$) δ 170.0, 137.4, 128.6128.1 (2C), 105.6 (d, J=220.0 Hz), 76.4 (d, J=1.8 Hz), 74.2 (d, J=1.7 Hz), 72.0, 66.7, 66.4 (d, J=39.9 Hz), 63.2, 20.7, 17.9, 17.9, 11.9. $^{19}$F NMR (377 MHz, CDCl$_3$) δ −136.5 (d, J=49.0 Hz). ESI-HRMS m/z: Calcd. for C$_{24}$H$_{39}$O$_6$FSiNa [M+Na]$^+$: 493.2398; found: 493.2393.

2-O-Acetyl-3-O-benzyl-4-O-triethylsilyl-6-O-triisopropylsilyl-α-D-mannopyranosyl fluoride (29b)

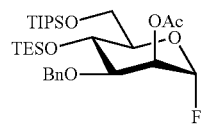

A stirred solution of 2-O-acetyl-3-O-benzyl-6-O-triisopropylsilyl-α-D-mannopyranosyl fluoride (200 mg, 0.42 mmol) in N,N-dimethylformamide (2 mL) was treated with imidazole (87 mg, 1.27 mmol) and chlorotriethylsilane (85 μL, 0.51 mmol) at rt and stirring was continued for 3 h at rt. Then the reaction mixture was diluted with ethyl acetate (50 mL) and ethyl acetate layer was washed with water (2×50 mL) and brine (50 ml), dried over anhydrous Na$_2$SO$_4$, and concentrated under reduced pressure. Purification by column chromatography eluting with ethyl acetate/hexane (1:99 to 1:15) afforded the desired product (220 mg, 0.38 mmol, 89%) as a colorless viscous liquid. $^1$H NMR (700 MHz, CDCl$_3$) δ 7.34-7.25 (m, 5H), 5.54 (dd, J=49.8, 2.0 Hz, 1H), 5.39 (dd, J=3.2, 2.0 Hz, 1H), 4.67 (d, J=11.1 Hz, 1H), 4.47 (d, J=11.1 Hz, 1H), 4.20 (t, J=9.4 Hz, 1H), 3.99 (dd, J=11.5, 3.1 Hz, 1H), 3.92 (dd, J=11.4, 1.9 Hz, 1H), 3.75-3.68 (m, 2H), 2.06 (s, 3H), 1.17-1.02 (m, 21H), 0.90 (t, J=8.0 Hz, 9H), 0.69-0.52 (m, 6H). $^{13}$C NMR (176 MHz, CDCl$_3$) δ 170.0, 137.8, 128.2, 127.8, 127.6, 105.5 (d, J=218.9 Hz), 77.4 (d, J=1.6 Hz), 76.4 (d, J=1.6 Hz), 71.5, 66.7 (d, J=40.2 Hz), 65.9, 61.7, 20.6, 17.9, 17.8, 12.1, 6.9, 5.1. ESI-HRMS m/z: Calcd. for C$_{30}$H$_{53}$O$_6$FSi$_2$Na [M+Na]$^+$: 607.3262; found: 607.3257.

2-O-Acetyl-3-O-benzyl-4-O-tri-n-butylsilyl-6-O-triisopropylsilyl-α-D-mannopyranosyl fluoride (S21)

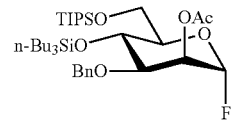

A stirred solution of 2-O-acetyl-3-O-benzyl-6-O-triisopropylsilyl-α-D-mannopyranosyl fluoride (200 mg, 0.42 mmol) in N,N-dimethylformamide (2 mL) was treated with imidazole (87 mg, 1.27 mmol) and chlorotributylsilane (0.17 mL, 0.64 mmol) at rt and stirring was continued overnight at rt. Then the reaction mixture was diluted with ethyl acetate (50 mL) and ethyl acetate layer was washed with water (2×50 mL) and brine (50 ml), dried over anhydrous Na$_2$SO$_4$, and concentrated under reduced pressure. Purification by column chromatography eluting with ethyl acetate/hexane (1:99 to 1:19) afforded the desired product (240 mg, 0.36 mmol, 84%) as a colorless viscous liquid. $^1$H NMR (700 MHz, CDCl$_3$) δ 7.33-7.24 (m, 5H), 5.54 (dd, J=49.7, 2.0 Hz, 1H), 5.41 (br s, 1H), 4.69 (d, J=11.1 Hz, 1H), 4.44 (d, J=11.1 Hz, 1H), 4.19 (t, J=9.4 Hz, 1H), 3.98 (dd, J=11.4, 3.2 Hz, 1H), 3.92 (dd, J=11.4, 1.9 Hz, 1H), 3.74-3.67 (m, 2H), 2.06 (s, 3H), 1.29-1.20 (m, 12H), 1.18-1.02 (m, 21H), 0.84 (t, J=6.8 Hz, 9H), 0.66-0.51 (m, 6H). $^{13}$C NMR (176 MHz, CDCl$_3$) δ 169.9, 137.8, 128.1, 127.6, 127.5, 105.6 (d, J=218.8 Hz), 77.5, 76.4 (d, J=1.3 Hz), 71.24, 66.5 (d, J=40.5 Hz), 66.0, 61.8, 26.6, 25.5, 20.6, 18.0, 17.9, 14.0, 13.7, 12.1. $^{19}$F NMR (377 MHz, CDCl$_3$) δ −136.5 (d, J=50.2 Hz). ESI-HRMS m/z: Calcd. for C$_{36}$H$_{65}$O$_6$FSi$_2$Na [M+Na]$^+$: 691.4201; found: 691.4193.

2-O-Acetyl-3,4,6-tri-O-benzyl-α-D-mannopyranosyl fluoride (26)

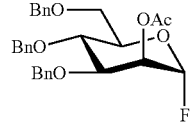

This compound was prepared according to the literature procedure (Cumpstey et al., *Org. Lett.* 2001, 3 (15), 2371-2374; Elie et al., *Tetrahedron* 1989, 45 (11), 3477-3486).

2-O-Acetyl-3,4,6-tri-O-benzyl-β-D-glucopyranosyl fluoride (28)

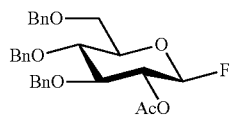

This compound was prepared according to the literature procedure (Cumpstey et al., *Org. Lett.* 2001, 3 (15), 2371-2374).

2,3,4,6-tetra-O-benzyl-β-D-glucopyranosyl fluoride

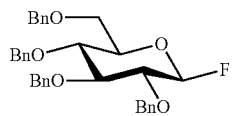

This compound was prepared according to the literature procedure (Kova et al., *J. Carbohydr.* 1987, 6 (3), 423-439).

2,3,4,6-tetra-O-Acetyl-α-D-mannopyranosyl fluoride

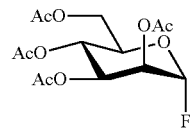

This compound was prepared according to the literature procedure (Wen et al., *Org. Lett.* 2017, 19 (9), 2402-2405).

2,3,4,6-tetra-O-Acetyl-β-D-glucopyranosyl fluoride

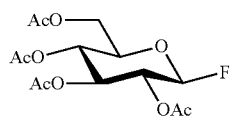

This compound was prepared according to the literature procedure (Wen et al., *Org. Lett.* 2017, 19 (9), 2402-2405).

2-O-Acetyl-3,4,6-tri-O-benzyl-β-D-galactopyranosyl fluoride

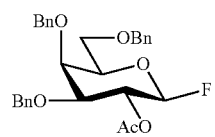

This compound was prepared according to the literature procedure (Kong et al., *Carbohydr. Res.* 1987, 162 (2), 217-225).

2,3,4-Tri-O-acetyl-α-L-rhamnopyranosyl fluoride

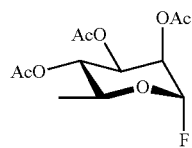

This compound was prepared according to the literature procedure (Mugunthan et al., *Tetrahedron Lett.* 2012, 53 (42), 5631-5634).

2,3,4-Tri-O-acetyl-α-L-fucopyranosyl fluoride

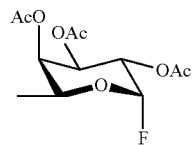

This compound was prepared according to the literature procedure (Dulery et al., Carbohydr. Res. 2007, 342 (7), 894-900).

2-O-Acetyl-3,4-di-O-benzyl-α-L-rhamnopyranosyl fluoride

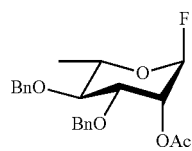

To a stirred solution of 1,2-O-(1-methoxyethylidene)-3,4-di-O-benzyl-β-L-rhamnopyranose (1.5 g, 3.75 mmol) dissolved in 15 ml of anhydrous dichloromethane at 0° C. was added Diethylaminosulfur trifluoride (906 mg, 0.74 ml, 5.62 mmol). The reaction mixture was stirred for 10 minutes at this temperature before being allowed to warm to rt. After one hour, TLC analysis indicated complete consumption of the starting material. The reaction mixture was diluted with 15 ml of Dichloromethane, and excess Diethylaminosulfur trifluoride was quenched via the dropwise addition of a saturated aqueous solution of $NaHCO_3$. The crude reaction mixture was then extracted with DCM (50 ml×2), the combined organic washes dried over $Na_2SO_4$, filtered and, concentrated under reduced pressure. Purification by column chromatography eluting with ethyl acetate/hexane (1:99 to 3:10) afforded the desired product (1.28 g, 3.28 mmol, 88%) as a colorless viscous liquid that solidifies upon standing. $^1H$ NMR (700 MHz, $CDCl_3$) δ 7.37-7.27 (m, 10H), 5.54-5.45 (m, 2H), 4.93 (d, J=10.8 Hz, 1H), 4.71 (d, J=11.2 Hz, 1H), 4.63 (d, J=10.8 Hz, 1H), 4.56 (d, J=11.2 Hz, 1H), 3.95-3.89 (m, 2H), 3.48 (t, J=9.5 Hz, 1H), 2.17 (s, 3H), 1.36 (d, J=6.2 Hz, 3H). $^{13}C$ NMR (176 MHz, $CDCl_3$) δ 170.1, 138.3, 137.8, 128.6, 128.5, 128.2, 128.1, 128.0, 127.9, 105.5 (d, J=219.6 Hz), 79.1, 77.2 (d, J=2.0 Hz), 75.6, 72.2, 70.4 (d, J=2.9 Hz), 67.5 (d, J=40.5 Hz), 21.1, 18.0. $^{19}$F NMR (377 MHz, CDCl$_3$) δ −136.8 (d, J=49.4 Hz). ESI-HRMS m/z: Calcd. for C$_{22}$H$_{25}$FO$_5$Na [M+Na]$^+$: 411.1578; found: 411.1582.

3,4-di-O-benzyl-α-L-rhamnopyranosyl fluoride

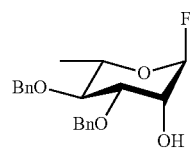

2-O-Acetyl-3,4-di-O-benzyl-α-L-rhamnopyranosyl fluoride (490 mg, 1.26 mmol) was dissolved in a 1:1:1 mixture of Tetrahydrofuran: Methanol: Propylamine and heated to 40° C. overnight, after which TLC analysis indicated full consumption of the starting material. The crude reaction mixture was concentrated under reduced pressure and purification by column chromatography, afforded the desired product (416 mg, 1.2 mmol, 95%) as a viscous, colorless oil. $^1$H NMR (700 MHz, CDCl$_3$) δ 7.5-7.2 (m, 10H), 5.6 (d, J=49.4 Hz, 1H), 4.9 (d, J=10.9 Hz, 1H), 4.8-4.6 (m, 3H), 4.1 (s, 1H), 3.9 (dq, J=9.6, 6.2 Hz, 1H), 3.8 (dd, J=9.2, 3.0 Hz, 1H), 3.5 (d, J=9.5 Hz, 1H), 2.59 (br s, 1H), 1.4 (d, J=6.2 Hz, 3H). $^{13}$C NMR (176 MHz, CDCl$_3$) δ 138.1, 137.5, 128.6, 128.4, 128.2, 127.9 (2C), 127.8, 107.0 (d, J=216.0 Hz), 79.0 (d, J=2.0 Hz), 78.9, 75.5, 72.4, 69.9 (d, J=3.1 Hz), 67.4 (d, J=40.4 Hz), 17.8. $^{19}$F NMR (377 MHz, CDCl$_3$) δ −139.8 (d, J=45.9 Hz).

2,3,5-Tri-O-acetyl-α-D-ribofuranosyl fluoride and 2,3,5-tri-O-acetyl-β-D-ribofuranosyl fluoride

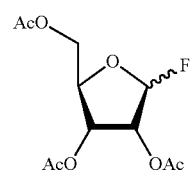

This compound was previously synthesized (Bock et al., Acta. Chem. Scand. B, 1976; Vol. 30B, pp 727-732), however a new procedure was developed below to avoid the undesirable use of anhydrous HF. A plastic bottle was charged with β-D-Ribofuranose tetraacetate (2.5 g, 7.85 mmol) and HF·Pyridine (5 ml). The reaction mixture was stirred for 2 hours at rt, before TLC analysis indicated full consumption of the starting material. The crude mixture was then diluted with dichloromethane (100 ml), washed with water (2×100 ml) and saturated NaHCO$_3$ (2×100 ml) before being dried over Na$_2$SO$_4$, filtered and concentrated under reduced pressure. Purification by column chromatography eluting with ethyl acetate/hexane (1:99 to 1:1) afforded the desired products (2.0 g, 7.2 mmol, 92%, 1:1 mixture of anomers) as a white solid. Spectral data matched the limited data that was previously reported[29], full characterization is provided for the readers convenience. $^1$H NMR (700 MHz, CDCl$_3$) δ 5.86 (dd, J=64.4, 3.4 Hz, 1H), 5.67 (d, J=61.4 Hz, 1H), 5.39 (t, J=4.6 Hz, 1H), 5.36 (ddd, J=6.9, 4.8, 1.8 Hz, 1H), 5.28-5.24 (m, 1H), 5.02 (ddd, J=21.3, 6.9, 3.5 Hz, 1H), 4.54 (q, J=3.2 Hz, 1H), 4.47 (dd, J=12.2, 3.5 Hz, 1H), 4.43-4.39 (m, 1H), 4.31 (dd, J=12.2, 3.1 Hz, 1H), 4.21 (dd, J=12.3, 3.8 Hz, 1H), 4.07 (dd, J=12.2, 5.3 Hz, 1H), 2.11 (s, 6H), 2.10 (s, 3H), 2.07 (s, 3H), 2.07 (s, 3H), 2.05 (s, 3H). $^{13}$C NMR (176 MHz, CDCl$_3$) δ 170.5, 170.3, 170.2, 169.6, 169.5, 169.2, 111.8 (d, J=225.6 Hz), 107.5 (d, J=234.3 Hz), 82.8 (d, J=1.8 Hz), 80.4 (d, J=2.7 Hz), 73.9 (d, J=35.7 Hz), 71.2 (d, J=20.8 Hz), 69.9, 68.9, 63.2, 63.2, 20.7, 20.6, 20.6, 20.4, 20.3, 20.3. $^{19}$F NMR (377 MHz, CDCl$_3$) δ−115.35−−116.88 (m), −133.05 (dd, J=64.6, 21.1 Hz). ESI-HRMS m/z: Calcd. for C$_{11}$H$_{25}$FO$_7$Na [M+Na]$^+$: 301.0694; found: 301.0701.

2,3,5-Tri-O-acetyl-α-D-xylofuranosyl fluoride and 2,3,5-tri-O-acetyl-β-D-xylofuranosyl fluoride

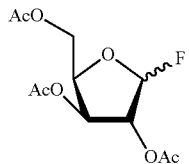

A plastic bottle was charged with β-D-xylofuranose tetraacetate (528 mg, 1.66 mmol) and HF·Pyridine (2 ml). The reaction mixture was stirred for 30 minutes at rt, before TLC analysis indicated full consumption of the starting material. The crude mixture was then diluted with dichloromethane (50 ml), washed with water (2×50 ml) and saturated NaHCO$_3$ (2×50 ml) before being dried over Na$_2$SO$_4$, filtered and concentrated under reduced pressure. Purification by column chromatography eluting with ethyl acetate/hexane (1:99 to 1:1) afforded the desired products (252 mg, 0.91 mmol, 55%, approximately 1:1 mixture of anomers) as a colorless oil. $^1$H NMR (700 MHz, CDCl$_3$) δ 5.92 (dd, J=63.5, 3.6 Hz, 1H), 5.69 (d, J=61.6 Hz, 1H), 5.53 (t, J=6.7 Hz, 1H), 5.39 (d, J=5.7 Hz, 1H), 5.23 (dd, J=5.0, 1.1 Hz, 1H), 5.11 (ddd, J=17.3, 6.3, 3.6 Hz, 1H), 4.75-4.70 (m, 2H), 4.33 (dd, J=11.8, 5.0 Hz, 1H), 4.27-4.23 (m, 2H), 4.13 (dd, J=12.4, 3.9 Hz, 1H), 2.14 (s, 3H), 2.12 (s, 3H), 2.11 (s, 3H), 2.10 (s, 3H), 2.09 (s, 3H), 2.08 (s, 3H). $^{13}$C NMR (176 MHz, CDCl$_3$) δ 170.4, 170.3, 170.1 (2C), 169.6, 169.0, 111.8 (d, J=227.7 Hz), 106.2 (d, J=231.9 Hz), 80.8 (d, J=2.5 Hz), 79.6 (d, J=36.6 Hz), 76.8 (d, J=20.7 Hz), 76.0 (d, J=1.6 Hz), 73.2, 73.1, 62.5, 61.3 (d, J=1.7 Hz), 20.8, 20.7, 20.5 (2C), 20.5, 20.4. $^{19}$F NMR (377 MHz, CDCl$_3$) δ −119.2 (dt, J=61.5, 5.2 Hz), −134.5 (dd, J=63.7, 17.4 Hz). ESI-HRMS m/z: Calcd. for C$_{11}$H$_{15}$FO$_7$Na [M+Na]$^+$: 301.0694; found: 301.0699.

Example 2: Boron-Catalyzed Glycosylations

General experimental procedure (C) for the glycosylation using glycosyl fluorides and TMS ethers under inert conditions. Tris(pentafluorophenyl) borane was weighed in an inert atmosphere glovebox, and added as a solution in anhydrous toluene (0.5 mL) to a stirred solution of glycosyl fluoride donor (0.20 mmol) and silyl ether acceptor (0.22 mmol) in anhydrous toluene (3.5 mL) at rt. After stirring for 1 hour at rt, the reaction mixture was concentrated under reduced pressure. The residue was subjected to column chromatography on silica gel to give the desired glycosylated product. This procedure was followed in all cases reported in Schemes 3-5 unless otherwise noted.

General experimental procedure (D) for the glycosylation using glycosyl fluorides and TMS ethers with benchtop setup. Tris(pentafluorophenyl) borane monohydrate was prepared as previously described (Bergquist et al., *J. Am. Chem. Soc.* 2000, 122 (43), 10581-10590), and material thus synthesized was found to be stable in air with no loss in activity over a period of five months. Tris(pentafluorophenyl) borane monohydrate was weighed in ambient conditions, along with glycosyl fluoride donor (0.20 mmol) and silyl ether acceptor (0.22 mmol). The reaction flask was evacuated and backfilled with $N_2$ repeatedly before the addition of 4 ml of anhydrous toluene. After stirring for 1 hour at rt the reaction mixture was concentrated under reduced pressure. The residue was subjected to column chromatography on silica gel to give the desired glycosylated product. This procedure afforded an 87% isolated yield of product 1a as described in Scheme 6. Modifying the procedure by using unpurified ACS certified grade dichloromethane and conducting the reaction in air afforded product 1a in 77% isolated yield on 0.2 mmol scale and 87% yield on 2.02 mmol scale.

Methyl-2,3,6-tri-O-benzyl-4-O-(2-O-acetyl-3,4,6-tri-O-benzyl-α-D-mannopyranosyl)-α-D-glucopyranoside (1a)

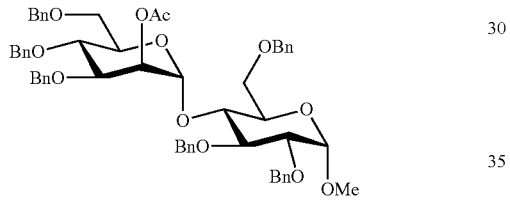

This compound was prepared by following the general experimental procedure (C) using 2-O-acetyl-3,4,6-tri-O-benzyl-α-D-mannopyranosyl fluoride (100 mg, 0.20 mmol), methyl-2,3,6-tri-O-benzyl-4-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:4) afforded the desired product (160 mg, 0.17 mmol, 84%) as a white foam. Spectral data matched that previously reported.

Methyl-2,3-di-O-benzyl-4-O-(2-O-acetyl-3,4,6-tri-O-benzyl-α-D-mannopyranosyl)-6-O-triisopropylsilyl-α-D-glucopyranoside (1b)

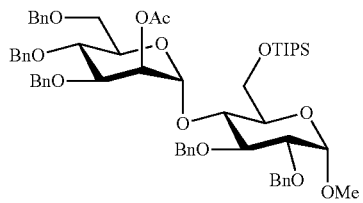

This compound was prepared by following the general experimental procedure (C) using 2-O-acetyl-3,4,6-tri-O-benzyl-α-D-mannopyranosyl fluoride (100 mg, 0.20 mmol), methyl-2,3-di-O-benzyl-4-O-trimethylsilyl-6-O-triisopropylsilyl-α-D-glucopyranoside (134 mg, 0.22 mmol), and tris(pentafluorophenyl) borane (5.2 mg, 0.01 mmol). Purification by column chromatography eluting with ethyl acetate/hexane (1:19 to 1:7) afforded the desired product (180 mg, 0.18 mmol, 89%) as a white foam. $^1$H NMR (700 MHz, $CDCl_3$) δ 7.36-7.23 (m, 23H), 7.18-7.15 (m, 2H), 5.50 (br s, 2H), 5.07 (d, J=11.1 Hz, 1H), 4.86 (d, J=11.0 Hz, 1H), 4.75 (d, J=11.1 Hz, 1H), 4.72 (d, J=12.1 Hz, 1H), 4.69 (d, J=12.2 Hz, 1H), 4.67 (d, J=11.0 Hz, 1H), 4.61 (d, J=12.0 Hz, 1H), 4.59 (d, J=3.5 Hz, 1H), 4.49 (d, J=10.6 Hz, 1H), 4.48 (d, J=11.8 Hz, 1H), 4.44 (d, J=11.0 Hz, 1H), 3.99-3.95 (m, 2H), 3.93-3.87 (m, 2H), 3.87-3.82 (m, 1H), 3.82-3.77 (m, 2H), 3.70-3.63 (m, 3H), 3.52 (dd, J=9.8, 3.5 Hz, 1H), 3.41 (s, 3H), 1.99 (s, 3H), 1.10-1.15 (m, 3H), 1.04 (d, J=6.6 Hz, 18H). $^{13}$C NMR (176 MHz, $CDCl_3$) δ 169.9, 138.7, 138.6, 138.3, 138.0 (2C), 128.4, 128.3 (2C), 128.2 (2C), 128.0, 127.9, 127.8, 127.6, 127.5 (2C), 127.3 (3C), 98.8, 97.3, 81.9, 80.2, 78.3, 75.1, 75.0, 74.8, 73.9, 73.6, 73.2, 72.7, 71.8, 71.4, 68.8, 68.7, 63.5, 54.9, 21.0, 18.0, 12.0. ESI-HRMS m/z: Calcd. for $C_{59}H_{80}O_{12}NSi$ $[M+NH_4]^+$: 1022.5450; found: 1022.5442.

Methyl-2,3-di-O-benzyl-4-O-(2-O-acetyl-3,4,6-tri-O-benzyl-α-D-mannopyranosyl)-6-O-tert-butyldimethylsilyl-α-D-glucopyranoside (1c)

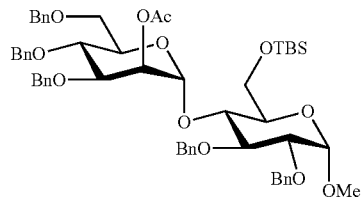

This compound was prepared by following the general experimental procedure (C) using 2-O-acetyl-3,4,6-tri-O-benzyl-α-D-mannopyranosyl fluoride (100 mg, 0.20 mmol), methyl-2,3-di-O-benzyl-4-O-trimethylsilyl-6-O-tert-butyldimethylsilyl-α-D-glucopyranoside (124 mg, 0.22 mmol), and tris(pentafluorophenyl) borane (5.2 mg, 0.01 mmol). Purification by column chromatography eluting with ethyl acetate/hexane (1:19 to 1:4) afforded the desired product (156 mg, 0.16 mmol, 80%) as a white foam. $^1$H NMR (700 MHz, $CDCl_3$) δ 7.44-7.23 (m, 23H), 7.21 7.17 (m, 2H), 5.52 (br s, 1H), 5.48 (br s, 1H), 5.08 (d, J=11.1 Hz, 1H), 4.87 (d, J=10.9 Hz, 1H), 4.77 (d, J=11.1 Hz, 1H), 4.73 (d, J=12.1, 1H), 4.72 (d, J=12.1, 1H), 4.68 (d, J=11.1 Hz, 1H), 4.63 (d, J=12.0 Hz, 1H), 4.60 (d, J=3.5 Hz, 1H), 4.54 4.49 (m, 2H), 4.46 (d, J=11.0 Hz, 1H), 3.98 (t, J=9.1 Hz, 1H), 3.95 3.86 (m, 4H), 3.84 (dd, J=10.6, 3.5 Hz, 1H), 3.79 (dd, J=11.4, 5.5 Hz, 1H), 3.75 3.70 (m, 2H), 3.63 3.58 (m, 1H), 3.53 (dd, J=9.6, 3.4 Hz, 1H), 3.41 (s, 3H), 2.02 (s, 3H), 0.91 (s, 9H), 0.06 (s, 3H), 0.06 (s, 3H). $^{13}$C NMR (176 MHz, $CDCl_3$) δ 169.9, 138.7, 138.6, 138.3, 138.0 (20) 128.4, 128.3 (2C), 128.2 (20) 128.0, 127.9, 127.8, 127.6, 127.5 (2C), 127.3 (3C), 98.8, 97.3, 81.9, 80.2, 78.3, 75.1, 75.0, 74.8, 73.9, 73.6, 73.2, 72.7, 71.8, 71.4, 68.8, 68.7, 63.5, 54.9, 20.9, 18.0, 12.0, 11.9. ESI-HRMS m/z: Calcd. for $C_{56}H_{70}O_{12}NaSi$ $[M+Na]^+$: 985.4513; found: 985.4522.

Methyl-2,4,6-tri-O-benzyl-3-O-(2-O-acetyl-3,4,6-tri-O-benzyl-α-D-mannopyranosyl)-α-D-glucopyranoside (2)

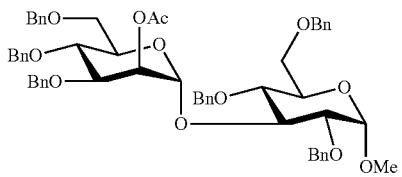

This compound was prepared by following the general experimental procedure (C) using 2-O-acetyl-3,4,6-tri-O-benzyl-α-D-mannopyranosyl fluoride (100 mg, 0.20 mmol), methyl-2,4,6-tri-O-benzyl-3-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:4) afforded the desired product (158 mg, 0.17 mmol, 83%) as a white foam. $^1$H NMR (700 MHz, CDCl$_3$) δ 7.41 7.08 (m, 30H), 5.56 (br s, 1H), 5.42 (br, 1H), 4.87 (d, J=11.0 Hz, 1H), 4.74 (t, J=11.7 Hz, 2H), 4.71-4.67 (m, 2H), 4.64 (d, J=12.0 Hz, 1H), 4.60 (d, J=11.5 Hz, 1H), 4.56-4.47 (m, 5H), 4.34 (d, J=12.0 Hz, 1H), 4.26-4.21 (m, 1H), 4.20 (t, J=9.2 Hz, 1H), 4.01 (dd, J=9.5, 3.1 Hz, 1H), 3.98 (t, J=9.5 Hz, 1H), 3.78-3.73 (m, 2H), 3.71 (t, J=9.1 Hz, 1H), 3.68-3.64 (m, 1H), 3.61 (dd, J=11.1, 3.2 Hz, 1H), 3.54 (dd, J=11.1, 1.9 Hz, 1H), 3.45 (dd, J=9.7, 3.6 Hz, 1H), 3.36 (s, 3H), 2.05 (s, 3H). $^{13}$C NMR (176 MHz, CDCl$_3$) δ 170.3, 139.0, 138.5, 138.2, 137.8, 137.7, 137.6, 128.7, 128.4 (2C), 128.3, 128.2 (2C), 128.1 (30) 128.0 (2C), 127.9, 127.8, 127.6 (2C), 127.5, 127.4 (2C), 127.3, 98.2, 97.6, 79.1, 78.3, 78.1, 76.2, 74.9, 74.4, 74.2, 73.6, 73.3, 73.1, 71.7, 71.3, 69.6, 68.8, 68.5, 68.3, 55.1, 21.0. ESI-HRMS m/z: Calcd. for C$_{57}$H$_{76}$O$_{12}$N [M+NH$_4$]+: 956.4585; found: 956.4574.

Methyl-2-O-benzyl-3-O-(2-O-acetyl-3,4,6-tri-O-benzyl-α-D-mannopyranosyl)-4,6-O-benzylidene-α-D-glucopyranoside (3)

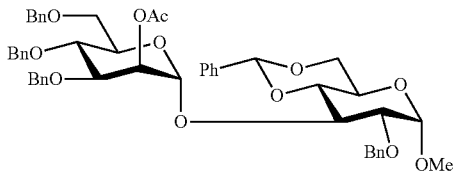

This compound was prepared by following the general experimental procedure (C) using 2-O-acetyl-3,4,6-tri-O-benzyl-α-D-mannopyranosyl fluoride (100 mg, 0.20 mmol), methyl-2-O-benzyl-3-O-trimethylsilyl-4,6-O-benzylidene-α-D-glucopyranoside (99 mg, 0.22 mmol), and tris(pentafluorophenyl) borane (5.2 mg, 0.01 mmol). Purification by column chromatography eluting with ethyl acetate/hexane (1:19 to 1:4) afforded the desired product (155 mg, 0.18 mmol, 91%) as a white foam. $^1$H NMR (700 MHz, CDCl$_3$) δ 7.51-7.46 (m, 2H), 7.41-7.18 (m, 23H), 5.60 (br s, 1H), 5.58 (br s, 1H), 5.46 (br s, 1H), 4.91 (d, J=10.9 Hz, 1H), 4.74 (dd, J=11.7, 3.2 Hz, 2H), 4.70-4.66 (m, 2H), 4.57-4.51 m, 3H), 4.40 (d, J=12.0 Hz, 1H), 4.33-4.28 (m, 2H), 4.21-4.51 (m, 1H), 4.08-4.01 (m, 2H), 3.85 (td, J=10.0, 4.9 Hz, 1H), 3.78-3.69 (m, 2H), 3.68-3.61 (m, 2H), 3.51 (dd, J=9.5, 3.6 Hz, 1H), 3.42 (s, 3H), 2.14 (s, 3H). $^{13}$C NMR (176 MHz, CDCl$_3$) δ 170.3, 139.0, 138.5, 138.2, 137.5, 137.2, 128.9, 128.6, 128.5, 128.4, 128.2 (2C), 128.1 (3C), 128.0, 127.7 (2C), 127.5, 127.4, 126.1, 101.2, 98.7, 98.1, 82.5, 78.0, 75.0, 74.2, 73.6, 73.4 (2C), 71.6, 71.4, 69.0, 68.6, 68.4, 61.9, 55.3, 21.1. ESI-HRMS m/z: Calcd. for C$_{20}$H$_{54}$O$_{12}$Na [M+Na]+: 869.3499; found: 869.3513.

4-Penten-1-yl-2,3,6-tri-O-benzyl-4-O-(2-O-acetyl-3,4,6-tri-O-benzyl-α-D-mannopyranosyl)-β-D-glucopyranoside (4)

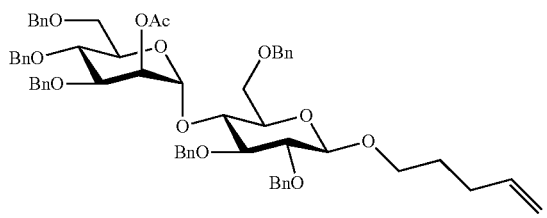

This compound was prepared by following the general experimental procedure (C) using 2-O-acetyl-3,4,6-tri-O-benzyl-α-D-mannopyranosyl fluoride (100 mg, 0.20 mmol), 4-penten-1-yl-2,3,6-tri-O-benzyl-4-O-trimethylsilyl-α-D-glucopyranoside (131 mg, 0.22 mmol), and tris(pentafluorophenyl) borane (5.2 mg, 0.01 mmol). Purification by column chromatography eluting with ethyl acetate/hexane (1:19 to 1:6) afforded the desired product (166 mg, 0.17 mmol, 83%) as a white foam. $^1$H NMR (700 MHz, CDCl$_3$) δ 7.30-7.1.0 (m, 30H), 5.81 (ddt, J=17.0, 10.2, 6.7 Hz, 1H), 5.44-5.41 (m, 2H), 5.04-4.91 (m, 4H), 4.79 (d, J=10.7 Hz, 1H), 4.68 (d, J=11.0 Hz, 1H), 4.66-4.59 (m, 3H), 4.55 (d, J=12.1 Hz, 1H), 4.50 (d, J=12.1 Hz, 1H), 4.44-4.36 (m, 4H), 3.94 (dt, J=9.6, 6.5 Hz, 1H), 3.86-3.75 (m, 5H), 3.68-3.64 (m, 2H), 3.61 (t, J=9.0 Hz, 1H), 3.55 (dt, J=9.6, 6.8 Hz, 1H), 3.50 (d, J=11.0, 1H), 3.48-3.41 (m, 2H), 2.19-2.13 (m, 2H), 1.95 (s, 3H), 1.78-1.70 (m, 2H). $^{13}$C NMR (176 MHz, CDCl$_3$) δ 170.0, 138.5, 138.4 (4C), 138.3, 138.1 (2C), 128.4 (3C), 128.3, 128.2, 128.1, 128.0, 127.9, 127.8, 127.7 (2C) 127.6 (2C), 127.5, 127.4, 127.3, 115.1, 103.6, 99.1, 84.7, 82.3, 78.3, 75.3, 75.2, 74.9, 74.7, 74.5, 74.1, 73.6, 73.5, 72.5, 71.8, 69.6, 69.4, 68.8 (2C), 31.0, 30.3, 29.1, 21.0. ESI-HRMS m/z: Calcd. for C$_{61}$H$_{72}$O$_{12}$N [M NH$_4$]+: 1010.5049; found: 1010.5061.

Methyl-2,3,6-tri-O-benzyl-4-O-(2-O-acetyl-3,4,6-tri-O-benzyl-α-D-mannopyranosyl)-α-D-galactopyranoside (5a)

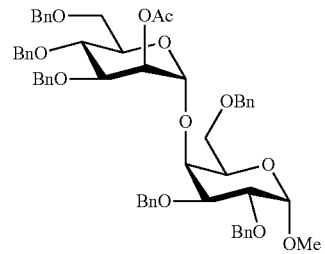

This compound was prepared by following the general experimental procedure (C) using 2-O-acetyl-3,4,6-tri-O-benzyl-α-D-mannopyranosyl fluoride (100 mg, 0.20 mmol), methyl-2,3,6-tri-O-benzyl-4-O-trimethylsilyl-α-D-galactopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (142 mg, 0.15 mmol, 75%) as a white foam. $^1$H NMR (700 MHz, CDCl$_3$) δ 7.41-7.01 (m, 30H), 5.34 (s, 1H), 4.94 (s, 1H), 4.80-4.76 (m, 2H), 4.73 (d, J=11.9 Hz, 1H), 4.68-4.64 (m, 2H), 4.63-4.57 (m, 2H), 4.55-4.51 (m, 3H), 4.42-4.33 (m, 2H), 4.18-4.11 (m, 3H), 4.00 (t, J=9.7 Hz, 1H), 3.88 (dd, J=9.7, 3.2 Hz, 1H), 3.83-3.77 (m, 3H), 3.54 (t, J=8.8 Hz, 1H), 3.49 (dd, J=9.0, 5.7 Hz, 1H), 3.42 (d, J=11.1, 2.3 Hz, 1H), 3.30 (s, 3H), 3.05 (d, J=10.8 Hz, 1H), 2.07 (s, 3H). $^{13}$C NMR (176 MHz, CDCl$_3$) δ 170.7, 138.8 (2C), 138.3, 138.2 (2C), 137.8, 128.5 (2C), 128.4 (3C), 128.3 (2C), 128.1, 128.0, 127.9 (2C), 127.8 (3C), 127.6 (2C), 127.4 (2C), 99.3, 98.9, 78.2, 77.0, 75.8, 75.1 (2C), 74.1, 73.4 (3C), 72.7, 72.1, 71.6, 69.3, 68.7, 67.9 (2C), 55.5, 21.3. ESI-HRMS m/z: Calcd. for C$_{57}$H$_{62}$O$_{12}$Na [M+Na]$^+$: 961.4133; found: 961.4134.

Methyl-2,3,6-tri-O-benzyl-4-O-(2,3,4,6-tetra-O-acetyl-α-D-mannopyranosyl)-α-D-galactopyranoside (5b)

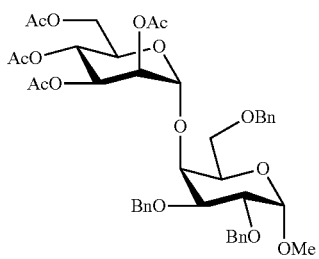

This compound was prepared by following the general experimental procedure (C) using 2,3,4,6-tetra-O-acetyl-α-D-mannopyranosyl fluoride (100 mg, 0.29 mmol), methyl-2,3,6-tri-O-benzyl-4-O-trimethylsilyl-α-D-galactopyranoside (123 mg, 0.31 mmol), and tris(pentafluorophenyl) borane (7.3 mg, 0.014 mmol). Purification by column chromatography eluting with ethyl acetate/hexane (1:4 to 1:1) afforded the desired product gave the desired product as a white foam (204 mg, 0.26 mmol, 90%). $^1$H NMR (700 MHz, CDCl$_3$) δ 7.46-7.24 (m, 15H), 5.41-5.26 (m, 4H), 4.99 (s, 1H), 4.88-4.78 (m, 2H), 4.77 4.71 (m, 2H), 4.67 (d, J=3.5 Hz, 1H), 4.56 (d, J=11.7 Hz, 1H), 4.45-4.40 (m, 2H), 4.20 (d, J=3.0 Hz, 1H), 3.98-3.91 (m, 2H), 3.90-3.84 (m, 2H), 3.62-3.50 (m, 3H), 3.34 (s, 3H), 2.14 (s, 3H), 2.04 (s, 3H), 2.03 (s, 6H). $^{13}$C NMR (176 MHz, CDCl$_3$) δ 170.7, 170.3, 170.0, 169.8, 138.5, 138.3, 137.9, 128.6 (20) 128.5 (2C), 128.0, 127.9 (2C), 127.8, 127.7, 98.8, 98.6, 76.5, 76.4, 76.0, 73.5, 73.4 (2C), 70.1, 69.2, 68.5, 68.4, 67.8, 66.0, 61.7, 55.6, 21.1, 20.9 (3C). ESI-HRMS: m/z: Calcd. for C$_{57}$H$_{62}$O$_{12}$Na [M+Na]$^+$: 961.4133; found: 961.4134.

Methyl-4-O-(2-O-acetyl-3,4,6-tri-O-benzyl-α-D-mannopyranosyl)-2,3,6-tri-O-benzyl-α-D-galactopyranoside

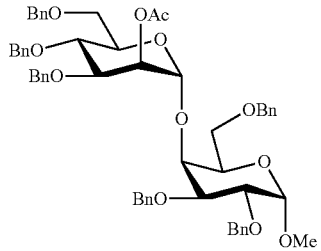

By following the general experimental procedure 2-O-acetyl-3,4,6-tri-O-benzyl-α-D-mannopyranosyl fluoride (100 mg, 0.20 mmol), methyl-2,3,6-tri-O-benzyl-4-O-trimethylsilyl-α-D-galactopyranoside (119 mg, 0.22 mmol), and tris-(pentafluorophenyl) borane (5.2 mg, 0.01 mmol) gave the desired product as a white foam (142 mg, 0.15 mmol, yield was 75%). $^1$H NMR (700 MHz, CDCl$_3$) δ 7.46-7.05 (m, 30H), 5.43 (d, J=3.3 Hz, 1H), 5.03 (s, 1H), 4.90-4.84 (m, 2H), 4.82 (d, J=11.9 Hz, 1H), 4.77-4.74 (m, 2H), 4.71 (d, J=11.4 Hz, 2H), 4.68-4.58 (m, 5H), 4.51-4.43 (m, 2H), 4.28-4.19 (m, 3H), 4.09 (t, J=9.7 Hz, 1H), 3.97 (dd, J=9.7, 3.2 Hz, 1H), 3.92-3.84 (m, 3H), 3.67-3.55 (m, 2H), 3.51 (dd, J=11.1, 2.3 Hz, 1H), 3.39 (s, 3H), 3.14 (d, J=10.8 Hz, 1H), 2.16 (s, 3H). $^{13}$C NMR (176 MHz, CDCl$_3$) δ 170.7, 138.8, 138.8, 138.3, 138.2, 138.2, 137.8, 128.5, 128.5, 128.4, 128.4, 128.3, 128.3, 128.1, 127.9, 127.9, 127.8, 127.8, 127.6, 127.6, 127.4, 127.4, 99.3, 98.9, 78.2, 77.0, 75.8, 75.1, 75.1, 74.1, 73.4, 73.4, 73.4, 72.7, 72.1, 71.6, 69.3, 68.7, 67.9, 67.9, 55.5, 21.3. ESI-HRMS m/z: Calcd. for C$_{57}$H$_{62}$O$_{12}$Na [M+Na]$^+$: 961.4133; found: 961.4134.

Methyl-2,4,6-tri-O-benzyl-3-O-(2-O-acetyl-3-O-benzyl-4-O-triethylsilyl-6-O-triisopropylsilyl-α-D-mannopyranosyl)-α-D-glucopyranoside (6a)

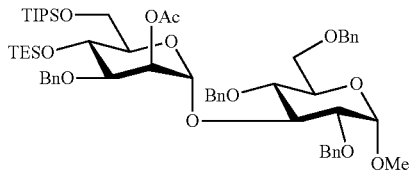

This compound was prepared by following the general experimental procedure (C) using 2-O-acetyl-3-O-benzyl-4-O-triethylsilyl-6-O-triisopropyl-α-D-mannopyranosyl fluoride (100 mg, 0.17 mmol), methyl-2,4,6-tri-O-benzyl-3-O-trimethylsilyl-α-D-glucopyranoside (101 mg, 0.19 mmol), and tris(pentafluorophenyl) borane (4.4 mg, 0.0085 mmol). Purification by column chromatography eluting with ethyl acetate/hexane (2:98 to 1:7) afforded the desired product (155 mg, 0.15 mmol, 88%) as a white foam. $^1$H NMR (700 MHz, CDCl$_3$) δ 7.42-7.21 (m, 18H), 7.16-7.12 (m, 2H), 5.44 (br s, 1H), 5.31 (br s, 1H), 4.73-4.67 (m, 3H), 4.65-4.61 (m, 2H), 4.54-4.47 (m, 3H), 4.38 (d, J=11.1 Hz, 1H), 4.21 (t, J=9.3 Hz, 1H), 4.16 (t, J=9.3 Hz, 1H), 3.92 (dt, J=9.4, 2.2 Hz, 1H), 3.85 (dd, J=11.3, 2.4 Hz, 1H), 3.81-3.71 (m, 4H), 3.67 (t, J=9.3 Hz, 1H), 3.65-3.61 (m, 1H), 3.41 (dd, J=9.6, 3.7 Hz, 1H), 3.36 (s, 3H), 1.93 (s, 3H), 1.15-1.04 (m, 21H), 0.90 (t, J=8.0 Hz, 9H), 0.70-0.53 (m, 6H). $^{13}$C NMR (176 MHz, CDCl$_3$) δ 170.3, 138.4, 138.0 (2C), 137.8, 128.8, 128.6, 128.5, 128.4, 128.2, 128.1 (2C), 127.9, 127.8, 127.6, 127.4, 98.0, 97.6, 79.4, 78.1, 77.9, 75.5, 74.2, 74.1, 73.7, 73.5, 71.0, 69.6, 68.4, 68.2, 66.5, 62.2, 55.2, 20.8, 18.2, 18.0, 12.3, 7.1, 5.2. ESI-HRMS m/z: Calcd. for C$_{58}$H$_{90}$O$_{12}$Si$_2$N [M+NH$_4$]$^+$: 1046.5845; found: 1046.5831.

Methyl-2,4,6-tri-O-benzyl-3-O-(2-O-acetyl-3-O-benzyl-4-O-tri-n-butylsilyl-6-O-triisopropylsilyl-α-D-mannopyranosyl)-α-D-glucopyranoside (6b)

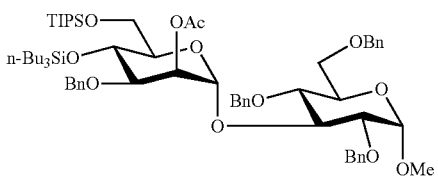

This compound was prepared by following the general experimental procedure (C) using 2-O-acetyl-3-O-benzyl-4-O-tri-n-butylsilyl-6-O-triisopropyl-α-D-mannopyranosyl fluoride (100 mg, 0.15 mmol), methyl-2,4,6-tri-O-benzyl-3-O-trimethylsilyl-α-D-glucopyranoside (89 mg, 0.16 mmol), and tris(pentafluorophenyl) borane (3.8 mg, 0.007 mmol). Purification by column chromatography eluting with ethyl acetate/hexane (1:19 to 1:3) afforded the desired product (150 mg, 0.13 mmol, 90%) as a white foam. $^1$H NMR (700 MHz, CDCl$_3$) δ 7.34-7.15 (m, 18H), 7.10-7.07 (m, 2H), 5.39 (dd, J=3.2, 1.9 Hz, 1H), 5.26 (d, J=1.9 Hz, 1H), 4.69-4.62 (m, 3H), 4.59-4.54 (m, 2H), 4.48-4.41 (m, 3H), 4.28 (d, J=11.0 Hz, 1H), 4.14 (t, J=9.4 Hz, 1H), 4.11 (t, J=9.3 Hz, 1H), 3.86 (dt, J=9.5, 2.2 Hz, 1H), 3.78 (dd, J=11.3, 2.6 Hz, 1H), 3.73 (dd, J=11.3, 1.8 Hz, 1H), 3.71-3.65 (m, 3H), 3.60 (t, J=9.5 Hz, 1H), 3.58-3.55 (m, 1H), 3.36 (dd, J=9.8, 3.7 Hz, 1H), 3.29 (s, 3H), 1.87 (s, 3H), 1.25-1.12 (m, 12H), 1.09-0.97 (d, J=5.6 Hz, 21H), 0.76 (t, J=7.0 Hz, 9H), 0.60-0.44 (m, 6H). $^{13}$C NMR (176 MHz, CDCl$_3$) δ 170.2, 138.5, 138.0, 137.8, 128.7, 128.6, 128.5, 128.4, 128.2, 128.1, 127.9, 127.7, 127.6, 127.4, 127.3, 98.1, 97.7, 79.4, 78.2, 78.0, 75.6, 74.2, 74.1, 73.8, 73.6, 70.8, 69.7, 68.5, 68.1, 66.5, 62.4, 55.2, 26.8, 25.7, 20.7, 18.2, 18.1, 14.2, 13.9, 12.3. ESI-HRMS m/z: Calcd. for C$_{60}$H$_{100}$O$_{12}$NSi$_2$ [M+NH$_4$]$^+$: 1130.6784; found: 1130.6778.

Methyl-2,3,6-tri-O-benzyl-4-O-(2,3,4-tri-O-acetyl-α-L-rhamnopyranosyl)-α-D-galactopyranoside (7)

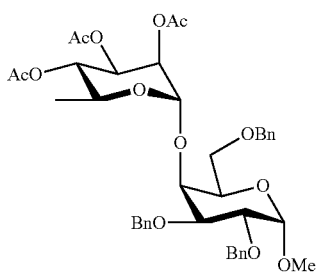

By following the general experimental procedure 2,3,4-tri-O-acetyl-α-D-rhamnopyranosyl fluoride (100 mg, 0.34 mmol), methyl-2,3,6-tri-O-benzyl-4-O-trimethylsilyl-α-D-galactopyranoside (202 mg, 0.38 mmol), and tris(pentafluorophenyl) borane (8.8 mg, 0.017 mmol) gave the desired product as a white foam (176 mg, 0.24 mmol, 70%). The stereochemistry at the newly formed anomeric linkage was confirmed by extracting the $^1$J[$^{13}$CH(1)] coupling constant. This was found to be 173 Hz, consistent with an α linkage$^{32}$. $^1$H NMR (700 MHz, CDCl$_3$) δ 7.44-7.39 (m, 2H), 7.35-7.24 (m, 13H), 5.49 (dd, J=3.4, 1.9 Hz, 1H), 5.30 (dd, J=10.1, 3.4 Hz, 1H), 5.14 (d, J=1.9 Hz, 1H), 5.02 (t, J=9.9 Hz, 1H), 4.85 (d, J=11.9 Hz, 1H), 4.81 (d, J=11.5 Hz, 1H), 4.68 (d, J=11.9 Hz, 1H), 4.63 (d, J=11.6 Hz, 1H), 4.61 (d, J=3.6 Hz, 1H), 4.57-4.52 (m, 2H), 4.11 (d, J=1.6 Hz, 1H), 3.98-3.92 (m, 3H), 3.88 (dd, J=10.1, 2.8 Hz, 1H), 3.66-3.55 (m, 2H), 3.36 (s, 3H), 2.04 (s, 3H), 2.02 (s, 3H), 1.98 (s, 3H), 1.12 (d, J=6.3 Hz, 3H). $^{13}$C NMR (176 MHz, CDCl$_3$) δ 170.1, 170.0, 169.7, 138.5 (2C), 138.0, 128.6 (2C), 128.5, 128.4, 127.9 (2C), 127.8, 127.7, 127.6, 99.3, 99.0, 78.4, 76.5, 75.6, 74.2, 73.7, 73.7, 71.2, 69.8, 69.4, 69.3, 68.8, 67.2, 55.6, 21.0 (2C), 20.9, 17.6. ESI-HRMS m/z: Calcd. for C$_{40}$H$_{48}$O$_{13}$Na [M+Na]$^+$: 759.2987; found: 759.2985.

Methyl-2,3,6-tri-O-benzyl-4-O-(2,3,4-tri-O-acetyl-β-L-fucopyranosyl)-α-D-glucopyranoside (8)

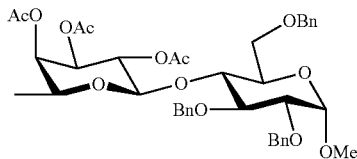

This compound was prepared by following the general experimental procedure (C) using 2,3,4-tri-O-acetyl-α-L-fucopyranosyl fluoride (75 mg, 0.26 mmol), methyl-2,3,6-tri-O-benzyl-4-O-trimethylsilyl-α-D-glucopyranoside (151 mg, 0.28 mmol), and tris(pentafluorophenyl) borane (6.6 mg, 0.01 mmol). Purification by column chromatography eluting with ethyl acetate/hexane (1:19 to 1:1) afforded the desired product (165 mg, 0.22 mmol, 87%) as a white foam. $^1$H NMR (700 MHz, CDCl$_3$) δ 7.43-7.23 (m, 15H), 5.17-5.14 (m, 2H), 5.03-4.99 (m, 2H), 4.95 (dd, J=10.5, 3.5 Hz, 1H), 4.76 (d, J=12.0 Hz, 1H), 4.70 (d, J=9.9 Hz, 1H), 4.66-4.60 (m, 3H), 4.54 (d, J=12.1 Hz, 1H), 3.93-3.85 (m, 2H), 3.81 (dd, J=10.9, 2.2 Hz, 1H), 3.73 (ddd, J=9.9, 4.9, 2.2 Hz, 1H), 3.65 (dd, J=10.9, 4.9 Hz, 1H), 3.59-3.52 (m, 2H), 3.38 (s, 3H), 2.16 (s, 3H), 2.06 (s, 3H), 1.99 (s, 3H), 1.04 (d, J=6.4 Hz, 3H). $^{13}$C NMR (176 MHz, CDCl$_3$) δ 170.6, 170.1, 169.4, 138.5, 138.2, 137.9, 128.7, 128.5, 128.3, 128.2, 128.1, 128.0 (2C), 127.4, 127.3, 100.2, 97.6, 82.0, 80.1, 75.7, 73.9, 73.4, 73.2, 71.4, 70.4, 69.4, 69.3, 68.9, 68.8, 55.2, 21.0, 20.7, 20.6, 15.8. ESI-HRMS m/z: Calcd. for C$_{40}$H$_{48}$O$_{13}$Na [M+Na]$^+$: 759.2993; found: 759.2988.

Methyl-2,3,6-tri-O-benzyl-4-O-(2-O-acetyl-3,4,6-tri-O-benzyl-β-D-glucopyranosyl)-α-D-glucopyranoside (9a)

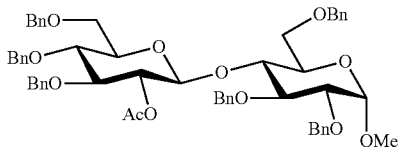

This compound was prepared by following the general experimental procedure (C) using 2-O-acetyl-3,4,6-tri-O-benzyl-β-D-glucopyranosyl fluoride (100 mg, 0.20 mmol), methyl-2,3,6-tri-O-benzyl-4-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (155 mg, 0.16 mmol, 82%) as a white foam. Spectral data matched that previously reported (Micheli et al., *Carbohydr. Res.* 1985, 139, C1-C3)

Methyl-2,3,6-tri-O-benzyl-4-O-(2,3,4,6-tetra-O-benzyl-α-D-glucopyranosyl)-α-D-glucopyranoside and Methyl-2,3,6-tri-O-benzyl-4-O-(2,3,4,6-tetra-O-benzyl-β-D-glucopyranosyl)-α-D-glucopyranoside (9b)

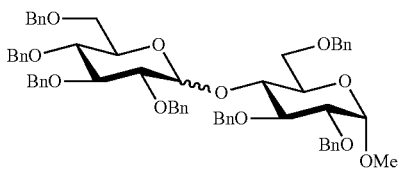

This compound was prepared by following the general experimental procedure (C) using 2,3,4,6-tetra-O-benzyl-β-D-glucopyranosyl fluoride (100 mg, 0.18 mmol), methyl-2,3,6-tri-O-benzyl-4-O-trimethylsilyl-α-D-glucopyranoside (109 mg, 0.20 mmol), and tris(pentafluorophenyl) borane (4.7 mg, 0.01 mmol). Purification by column chromatography eluting with ethyl acetate/hexane (1:19 to 1:4) afforded the desired product (165 mg, 0.17 mmol, 91%) in a 2.5:1 ratio of α:β anomers, as a white foam. Spectral data matched that previously reported (Wen et al., *Org. Lett.* 2017, 19 (9), 2402-2405).

Methyl-2,3,6-tri-O-benzyl-4-O-(2,3,4,6-tetra-O-acetyl-β-D-glucopyranosyl)-α-D-glucopyranoside (9c)

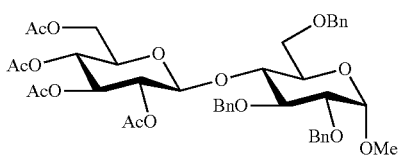

This compound was prepared by following the general experimental procedure (C) using 2,3,4,6-tetra-O-acetyl-4-D-glucopyranosyl fluoride (100 mg, 0.28 mmol), methyl-2,3,6-tri-O-benzyl-4-O-trimethylsilyl-α-D-glucopyranoside (168 mg, 0.31 mmol), and tris(pentafluorophenyl) borane (7.3 mg, 0.014 mmol). Purification by column chromatography eluting with ethyl acetate/hexane (1:19 to 1:1) afforded the desired product (190 mg, 0.24 mmol, 84%) as a white foam. Spectral data matched that previously reported (Du et al., Org. Lett. 2019, 21 (4), 980-983).

Methyl-2,4,6-tri-O-benzyl-3-O-(2-O-acetyl-3,4,6-tri-O-benzyl-β-D-glucopyranosyl)-α-D-glucopyranoside (10)

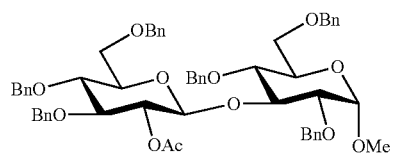

This compound was prepared by following the general experimental procedure (C) using 2-O-acetyl-3,4,6-tri-O-benzyl-β-D-glucopyranosyl fluoride (100 mg, 0.20 mmol), methyl-2,3,6-tri-O-benzyl-3-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (175 mg, 0.19 mmol, 92%) as a white foam. Spectral data matched that previously reported (Jayakanthan et al., *Carbohydr. Res.* 2005, 340 (17), 2688-2692).

Methyl-2,3,6-tri-O-benzyl-4-O-(2-O-acetyl-3,4,6-tri-O-benzyl-β-D-glucopyranosyl)-α-D-galactcopyranoside (11)

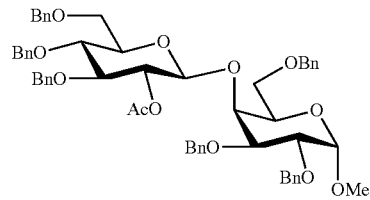

This compound was prepared by following the general experimental procedure (C) using 2-O-acetyl-3,4,6-tri-O-benzyl-β-D-glucopyranosyl fluoride (100 mg, 0.20 mmol), methyl-2,3,6-tri-O-benzyl-4-O-trimethylsilyl-α-D-galactopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (162 mg, 0.17 mmol, 85%) as a white foam. Spectral data matched that previously reported (Xiao et al., *J. Am. Chem. Soc.* 2016, 138 (40), 13402-13407).

Methyl-2-O-(2-O-acetyl-3,4,6-tri-O-benzyl-β-D-glucopyranosyl)-3-O-benzyl-4,6-O-benzylidene-α-D-glucopyranoside (12)

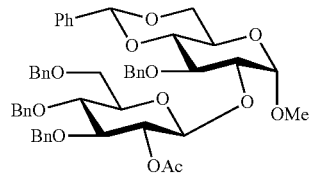

This compound was prepared by following the general experimental procedure (C) using 2-O-acetyl-3,4,6-tri-O-benzyl-β-D-glucopyranosyl fluoride (56 mg, 0.112 mmol), methyl-2-O-trimethylsilyl-3-O-benzyl-4,6-O-benzylidene-α-D-glucopyranoside (50 mg, 0.112 mmol), and tris(pentafluorophenyl) borane (2.9 mg, 0.006 mmol). Trituration of crude with a mixture of diethyl ether/hexane (1:1) afforded the desired product (73 mg, 0.086 mmol, 77%) as a white powder. $^1$H NMR (700 MHz, CDCl$_3$) δ 7.46 (d, J=6.9 Hz, 2H), 7.40-7.22 (m, 21H), 7.19 (d, J=6.8 Hz, 2H), 5.54 (s, 1H), 5.11 (t, J=8.6 Hz, 1H), 4.92 (d, J=3.6 Hz, 1H), 4.83-4.77 (m, 3H), 4.74-4.63 (m, 3H), 4.61-4.46 (m, 3H), 4.29 (dd, J=10.2, 4.9 Hz, 1H), 3.99 (t, J=9.4 Hz, 1H), 3.85 (td, J=10.0, 4.8 Hz, 1H), 3.77 3.62 (m, 6H), 3.59 (t, J=9.4 Hz, 1H), 3.50 (ddd, J=9.7, 5.0, 2.2 Hz, 1H), 3.40 (s, 3H), 1.76 (s, 3H). $^{13}$C NMR (176 MHz, CDCl$_3$) δ 169.5, 138.8, 138.2, 138.1, 137.9, 137.5, 129.0, 128.6 (3C), 128.4, 128.3, 128.2, 128.1, 128.0, 127.9 (2C), 127.8, 127.7, 126.2, 102.3, 101.5, 100.4, 83.2, 82.4, 80.2, 78.1, 77.7, 75.2, 75.1 (30) 73.6, 73.1, 69.3, 69.1, 62.4, 55.6, 21.0. ESI-HRMS m/z: Calcd. for C$_{56}$H$_{66}$O$_{12}$Na [M+Na]$^+$: 869.3513; found: 869.3504.

Methyl-2,3,6-tri-O-benzyl-4-O-(2-O-acetyl-3,4,6-tri-O-benzyl-β-D-galactopyranosyl)-α-D-glucopyranoside (13)

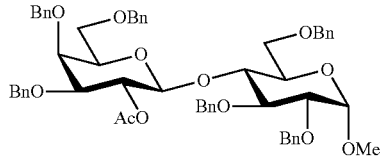

This compound was prepared by following the general experimental procedure (C) using 2-O-acetyl-3,4,6-tri-O-benzyl-β-D-galactopyranosyl fluoride (100 mg, 0.20 mmol), methyl-2,3,6-tri-O-benzyl-4-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (152 mg, 0.16 mmol, 80%) as a white foam. Spectral data matched the limited data that was previously reported[41], full characterization is provided for the readers convenience. $^1$H NMR (700 MHz, CDCl$_3$) δ 7.39 7.14 (m, 30H), 5.32 (dd, J=10.1, 7.9 Hz, 1H), 5.01 (d, J=10.8 Hz, 1H), 4.96 (d, J=11.4 Hz, 1H), 4.82 (d, J=12.2 Hz, 1H), 4.77 (d, J=10.8 Hz, 1H), 4.71-4.63 (m, 3H), 4.60-4.52 (m, 2H), 4.46 (d, J=12.2 Hz, 1H), 4.43-4.38 (m, 2H), 4.33 (d, J=11.7 Hz, 1H), 4.23 (d, J=11.7 Hz, 1H), 3.94 (d, J=2.8 Hz, 1H), 3.88-3.82 (m, 2H), 3.76 (dd, J=10.6, 3.3 Hz, 1H), 3.67-3.63 (m, 1H), 3.61 (dd, J=10.7, 1.9 Hz, 1H), 3.53 3.45 (m, 2H), 3.38 (s, 3H), 3.35-3.27 (m, 3H), 1.96 (s, 3H). $^{13}$C NMR (176 MHz, CDCl$_3$) δ 169.2, 139.5, 138.7, 138.5, 138.1 (2C), 138.0, 128.4 (3C), 128.3, 128.2, 128.1, 128.0, 127.9 (2C), 127.8, 127.7 (4C), 127.4, 127.3, 126.9, 100.7, 98.4, 80.5, 80.0, 79.0, 76.8, 75.3, 74.6, 73.6, 73.5, 73.4, 73.3, 72.6, 72.1, 71.6, 69.9, 68.0, 67.9, 55.3, 21.1. ESI-HRMS m/z: Calcd. for C$_{56}$H$_{66}$O$_{12}$N [M+NH$_4$]+: 956.4585; found: 956.4581.

Methyl-2,3,6-tri-O-benzyl-4-O-(2-deoxy-2-azido-3,4,6-tri-O-benzyl-α-D-glucopyranosyl)-α-D-glucopyranoside and Methyl-2,3,6-tri-O-benzyl-4-O-(2-deoxy-2-azido-3,4,6-tri-O-benzyl-β-D-glucopyranosyl)-α-D-glucopyranoside (14)

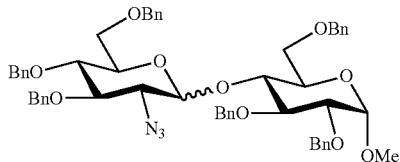

The general experimental procedure, an inseparable mixture of 2-azido-2-deoxy-3,4,6-tri-O-benzyl-β-D-glucopyranosyl fluoride and 2-azido-2-deoxy-3,4,6-tri-O-benzyl-α-D-glucopyranosyl fluoride (100 mg, 0.209 mmol), methyl-2,3,6-tri-O-benzyl-4-O-trimethylsilyl-α-D-glucopyranoside (124 mg, 0.230 mmol), and tris(pentafluorophenyl) borane (5.4 mg, 0.011 mmol) was carried out. Purification by column chromatography eluting with ethyl acetate/hexane (1:19 to 1:4) afforded the desired product as a white foam (117 mg, 0.127 mmol, 61%) in a 1:1 ratio of α:β anomers. The anomers were then characterized as a mixture and the spectral data matched that previously reported (Adhikari et al., J. Carbohydr. 2013, 32 (5-6), 336-359).

Methyl-2,3,6-tri-O-benzyl-4-O-2-deoxy-2-(1,3-dihydro-1,3-dioxo-2H-isoindol-2-yl)-3,4,6-tri-O-benzyl-[3-D-glucopyranosyl]-α-D-glucopyranoside and Methyl-2,3,6-tri-O-benzyl-4-O-[2-deoxy-2-(1,3-dihydro-1,3-dioxo-2H-isoindol-2-yl)-3,4,6-tri-O-benzyl-α-D-glucopyranosyl]-α-D-glucopyranoside (15)

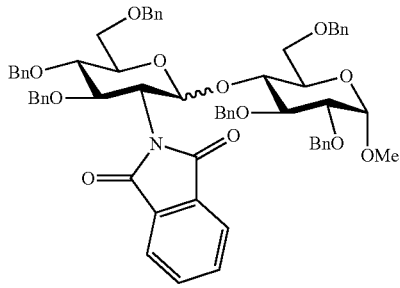

The general experimental procedure utilizing 2-deoxy-2-(1,3-dihydro-1,3-dioxo-2H-isoindol-2-yl)-3,4,6-tris-O-benzyl-β-D-glucopyranosyl fluoride (50 mg, 0.086 mmol), methyl-2,3,6-tri-O-benzyl-4-O-trimethylsilyl-α-D-glucopyranoside (51 mg, 0.095 mmol), and tris(pentafluorophenyl) borane (2.2 mg, 0.004 mmol) was carried out. Purification by column chromatography eluting with ethyl acetate/hexane (1:19 to 1:4) afforded the desired products as a white foam (82 mg, 0.08 mmol, 93%) in a 1:5 ratio of α:β anomers. An aliquot of this anomeric mixture was separated by preparative TLC, eluting with 1:4 ethyl acetate/hexanes (6 elutions) to yield analytically pure α and β anomers for characterization purposes.

α anomer: $^1$H NMR (700 MHz, CDCl$_3$) δ 7.72-7.60 (m, 4H), 7.32-7.18 (m, 20H), 7.15-7.11 (m, 2H), 7.06 (m, 2H), 7.02-6.99 (m, 4H), 5.76 (d, J=4.0 Hz, 1H), 5.03 (dd, J=11.2, 8.6 Hz, 1H), 4.87 (d, J=11.8 Hz, 1H), 4.74 (d, J=10.9 Hz, 1H), 4.68 (d, J=10.9 Hz, 1H), 4.59-4.51 (m, 7H), 4.45-4.42 (m, 2H), 4.28 (d, J=12.1 Hz, 1H), 4.02-3.93 (m, 2H), 3.88 (dd, J=10.9, 4.1 Hz, 1H), 3.84-3.76 (m, 2H), 3.72 (br d, J=9.6 Hz, 1H), 3.69 (d, J=11.1 Hz, 1H), 3.64 (t, J=9.1 Hz, 1H), 3.55 (dd, J=10.9, 2.3 Hz, 1H), 3.51 (dd, J=9.6, 3.6 Hz, 1H), 3.37 (d, J=10.9 Hz, 1H), 3.32 (s, 3H). $^{13}$C NMR (176 MHz, CDCl$_3$) δ 168.5, 167.9, 139.1, 138.5 (2C), 138.1 (2C), 137.9, 134.1, 133.8, 132.3, 131.0, 128.6, 128.5 (2C), 128.4 (2C), 128.3, 128.2, 128.1 (2C), 128.0, 127.8 (2C), 127.5 (2C), 127.3 (2C), 127.1, 127.0, 123.4, 123.3, 97.6 (2C), 82.2, 80.8, 79.8, 76.5, 74.9, 74.3, 74.2, 73.7, 73.4, 73.3, 71.8, 71.3, 69.6, 69.4, 68.2, 55.6, 55.5. ESI-HRMS m/z: Calcd. for C$_{63}$H$_{67}$O$_{12}$N [M+NH$_4$]$^+$: 1043.4689; found: 1043.4700.

β anomer: $^1$H NMR (700 MHz, CDCl$_3$) δ 7.78 (s, 1H), 7.67-7.51 (m, 3H), 7.38 7.34 (m, 2H), 7.32-7.17 (m, 23H), 6.97 6.93 (m, 2H), 6.90-6.82 (m, 3H), 5.40 (d, J=8.4 Hz, 1H), 5.02 (d, J=11.6 Hz, 1H), 4.86 (d, J=11.6 Hz, 1H), 4.81-4.75 (m, 2H), 4.68 (d, J=12.2 Hz, 1H), 4.63 (d, J=10.8 Hz, 1H), 4.54-4.50 (m, 2H), 4.49 4.45 (m, 2H), 4.40 (d, J=12.0 Hz, 1H), 4.32-4.25 (m, 3H), 4.17 (dd, J=10.8, 8.4 Hz, 1H), 3.93 (t, J=9.4 Hz, 1H), 3.85 (t, J=9.2 Hz, 1H), 3.77 (t, J=9.3 Hz, 1H), 3.57-3.51 (m, 2H), 3.48 (dd, J=11.1, 4.1 Hz, 1H), 3.41-3.34 (m, 4H), 3.24 (s, 3H). $^{13}$C NMR (176 MHz, CDCl$_3$) δ 168.6, 167.8, 139.7, 138.6, 138.4 (2C), 138.2, 138.1, 133.8 (2C), 132.0, 131.6, 128.6 (2C), 128.4, 128.3 (2C), 128.2 (3C), 128.1 (2C), 128.0, 127.9, 127.8, 127.5 (2C), 127.4 (2C), 127.3, 127.0, 123.5, 123.4, 98.3, 97.6, 80.3, 79.9, 79.5, 79.3, 75.4, 75.3, 75.0 (2C), 74.9, 73.6, 73.5, 72.9, 69.6, 68.5, 68.3, 56.9, 55.3. ESI-HRMS m/z: Calcd. for C$_{63}$H$_{67}$O$_{12}$N [M+NH$_4$]$^+$: 1043.4689; found: 1043.4692.

Phenyl-2-O-acetyl-3,4,6-tri-O-benzyl-α-D-mannopyranoside (16)

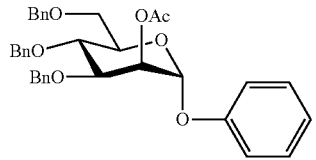

This compound was prepared by following the general experimental procedure (C) using 2-O-acetyl-3,4,6-tri-O-benzyl-α-D-mannopyranosyl fluoride (100 mg, 0.20 mmol), phenoxy(trimethyl)silane (40 μL, 0.22 mmol), and tris(pentafluorophenyl) borane (5.2 mg, 0.01 mmol). Purification by column chromatography eluting with ethyl acetate/hexane (1:19 to 1:4) afforded the desired product (105 mg, 0.18 mmol, 91%) as a white foam. $^1$H NMR (700 MHz, CDCl$_3$) δ 7.44 (d, J=7.0 Hz, 2H), 7.42-7.29 (m, 13H), 7.25 (d, J=7.0 Hz, 2H), 7.14 (d, J=8.1 Hz, 2H), 7.09 (t, J=7.4 Hz, 1H), 5.67 (d, J=2.0 Hz, 1H), 5.64 (dd, J=3.4, 2.0 Hz, 1H), 4.98 (d, J=10.7 Hz, 1H), 4.85 (d, J=11.1 Hz, 1H), 4.74 (d, J=12.0 Hz, 1H), 4.70 (d, J=11.1 Hz, 1H), 4.60 (d, J=10.7 Hz, 1H), 4.51 (d, J=12.0 Hz, 1H), 4.29 (dd, J=9.4, 3.4 Hz, 1H), 4.13 (t, J=9.7 Hz, 1H), 4.01 (ddd, J=10.0, 4.1, 1.9 Hz, 1H), 3.89 (dd, J=11.0, 4.0 Hz, 1H), 3.73 (dd, J=11.0, 2.0 Hz, 1H), 2.25 (s, 3H). $^{13}$C NMR (176 MHz, CDCl$_3$) δ 170.4, 156.0, 138.4, 138.2, 137.9, 129.6, 128.5, 128.4, 128.3, 128.2, 127.9 (3C), 127.8, 127.6, 126.6, 116.6, 96.1, 78.1, 75.3, 74.2, 73.4, 72.1 (2C), 68.7, 68.6, 21.1. ESI-HRMS m/z: Calcd. for C$_{35}$H$_{36}$O$_7$Na [M+Na]$^+$: 591.2359; found: 591.2358.

Methyl-2,3,6-tri-O-benzyl-4-O-[2-O-(2-O-acetyl-3,4,6-tri-O-benzyl-β-D-glucopyranosyl)-3,4,6-tri-O-benzyl-α-D-mannopyranosyl]-α-D-glucopyranoside (17)

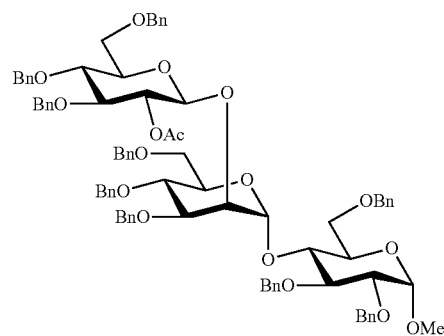

This compound was prepared by following the general experimental procedure (C) using methyl-2,3,6-tri-O-benzyl-4-O-(2-O-trimethylsilyl-3,4,6-tri-O-benzyl-α-D-mannopyranosyl)-α-D-glucopyranoside (100 mg, 0.10 mmol), 2-O-acetyl-3,4,6-tri-O-benzyl-α-D-glucopyranosyl fluoride (56 mg, 0.11 mmol), and tris(pentafluorophenyl) borane (3.0 mg, 0.006 mmol). Purification by column chromatography eluting with ethyl acetate/hexane (1:19 to 1:2) afforded the desired product (106 mg, 0.072 mmol, 75%) as a white foam. $^1$H NMR (700 MHz, CDCl$_3$) δ 7.36 7.15 (m, 45H), 5.15 (br s, 1H), 5.07 (d, J=11.5 Hz, 1H), 4.96 (dd, J=9.8, 8.1 Hz, 1H), 4.89 (d, J=10.9 Hz, 1H), 4.77-4.73 (m, 2H), 4.73-4.68 (m, 2H), 4.65-4.59 (m, 3H), 4.53 (m, 3H), 4.49 (m, 2H), 4.44-4.35 (m, 4H), 4.04 (d, J=8.0 Hz, 1H), 3.97 (t, J=2.6 Hz, 1H), 3.84-3.79 (m, 3H), 3.78-3.74 (m, 2H), 3.73-3.61 (m, 5H), 3.56-3.47 (m, 5H), 3.39 (s, 3H), 3.29 (t, J=9.4 Hz, 1H), 2.82-2.79 (m, 1H), 1.87 (s, 3H). $^{13}$C NMR (176 MHz, CDCl$_3$) δ 169.6, 139.1, 138.8, 138.6, 138.5 (4C), 138.3, 137.9, 128.7, 128.5 (4C), 128.4 (5C), 128.3 (2C), 128.2 (2C), 128.1, 128.0, 127.9, 127.8 (20) 127.7 (2C), 127.6 (3C), 127.5, 127.4, 126.3, 100.3, 100.1, 97.6, 82.5, 81.4, 80.0, 77.7, 77.6, 75.3 (2C), 74.9, 74.8 (4C), 74.7, 74.4, 73.6, 73.3, 73.2, 73.1, 72.7 (2C), 70.8, 70.5, 69.9, 69.4, 55.4, 21.0. ESI-HRMS m/z: Calcd. for C$_{84}$H$_{40}$O$_{17}$N [M+N$_4$]$^+$: 1388.6516; found: 1388.6477.

Methyl-2,3,6-tri-O-benzyl-4-O-(2,3,5-tri-O-acetyl-β-D-ribofuranosyl)-α-D-glucopyranoside (18)

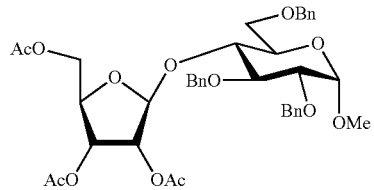

This compound was prepared by following the general experimental procedure (C) using methyl-2,3,6-tri-O-benzyl-4-O-trimethylsilyl-α-D-glucopyranoside (106 mg, 0.2 mmol), a 1:1 mixture of 2,3,5-tri-O-acetyl-α-D-ribofuranosyl fluoride and 2,3,5-tri-O-acetyl-β-D-ribofuranosyl fluoride (50 mg, 0.18 mmol), as well as tris(pentafluorophenyl)

borane (4.6 mg, 0.009 mmol). Purification by column chromatography eluting with ethyl acetate/hexane (1:19 to 1:1) afforded the desired product (121 mg, 0.17 mol, 92%) as a white foam. $^1$H NMR (700 MHz, CDCl$_3$) δ 7.43-7.39 (m, 2H), 7.35-7.24 (m, 13H), 5.35 (d, J=2.2 Hz, 1H), 5.23 (dd, J=6.1, 5.1 Hz, 2H), 5.13 (dd, J=4.9, 2.2 Hz, 1H), 4.92 (d, J=10.4 Hz, 1H), 4.88 (d, J=10.4 Hz, 1H), 4.74 (d, J=12.1 Hz, 1H), 4.62-4.53 (m, 4H), 4.23 (dd, J=11.7, 3.8 Hz, 1H), 4.19 (td, J=5.9, 3.8 Hz, 1H), 4.07 (dd, J=11.7, 5.6 Hz, 1H), 3.90 (t, J=9.2 Hz, 1H), 3.82 (t, J=9.3 Hz, 1H), 3.75 (dd, J=10.7, 3.6 Hz, 1H), 3.73 3.68 (m, 1H), 3.67 (dd, J=10.7, 1.8 Hz, 1H), 3.51 (dd, J=9.5, 3.5 Hz, 1H), 3.37 (s, 3H), 2.02 (s, 3H), 1.99 (s, 3H), 1.98 (s, 3H). $^{13}$C NMR (176 MHz, CDCl$_3$) δ 170.5, 169.6, 169.5, 138.9, 138.1, 138.0, 128.4, 128.2 (2C), 128.1, 128.0, 127.9, 127.5 (2C), 127.4, 106.5, 98.1, 80.4, 79.8, 78.0, 77.5, 75.2, 74.7, 73.4, 73.3, 71.0, 69.5, 68.6, 64.4, 55.3, 20.7, 20.5, 20.5. ESI-HRMS m/z: Calcd. for C$_{39}$H$_{40}$O$_{13}$N [M+NH$_4$]$^+$: 740.3277: found: 740.3280.

Methyl-2,3,6-tri-O-benzyl-4-O-(2,3,5-tri-O-acetyl-β-D-xylofuranosyl)-α-D-glucopyranoside (19)

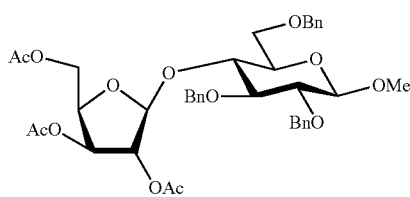

This compound was prepared by following the general experimental procedure (C) using methyl-2,3,6-tri-O-benzyl-4-O-trimethylsilyl-α-D-glucopyranoside (106 mg, 0.2 mmol), a 1:1 mixture of 2,3,5-tri-O-acetyl-α-D-xylofuranosyl fluoride and 2,3,5-tri-O-acetyl-β-D-xylofuranosyl fluoride (50 mg, 0.18 mmol), as well as tris(pentafluorophenyl)borane (4.6 mg, 0.009 mmol). Purification by column chromatography eluting with ethyl acetate/hexane (1:19 to 1:1) afforded the desired product (119 mg, 0.17 mol, 91%) as a colorless oil. $^1$H NMR (700 MHz, CDCl$_3$) δ 7.43-7.41 (m, 2H), 7.35-7.25 (m, 13H), 5.30 (br s, 1H), 5.24 (dd, J=5.1, 1.8 Hz, 1H), 5.06 (br s, 1H), 5.00 (d, J=10.5 Hz, 1H), 4.90 (d, J=10.5 Hz, 1H), 4.74 (d, J=12.2 Hz, 1H), 4.62-4.56 (m, 3H), 4.53 (d, J=12.1 Hz, 1H), 4.42 (q, J=5.7 Hz, 1H), 4.26 (dd, J=11.6, 5.4 Hz, 1H), 4.13 (dd, J=11.6, 6.7 Hz, 1H), 3.93 (t, J=9.2 Hz, 1H), 3.83 (t, J=9.3 Hz, 1H), 3.75 (ddd, J=21.9, 10.5, 3.9 Hz, 2H), 3.68 (s, 1H), 3.53 (dd, J=9.6, 3.5 Hz, 1H), 3.38 (s, 3H), 2.04 (s, 3H), 1.97 (s, 6H). $^{13}$C NMR (176 MHz, CDCl$_3$) δ 170.4, 169.6, 169.3, 139.0, 128.4, 128.3, 128.2, 128.1, 127.9, 127.8, 127.5, 127.5, 127.4, 107.5, 98.1, 80.6, 79.7, 77.7, 76.9, 75.2, 74.4, 73.4, 73.3, 69.7, 68.5, 62.3, 55.3, 20.7, 20.7, 20.6. ESI-HRMS Calcd. for C$_{39}$H$_5$O$_{13}$N [M+NH$_4$]$^+$: 740.3277; found: 740.3273.

Methyl-2,3,4-tri-O-benzyl-6-O-(2-O-acetyl-3,4,6-tri-O-benzyl-β-D-glucopyranosyl)-α-D-glucopyranoside (20)

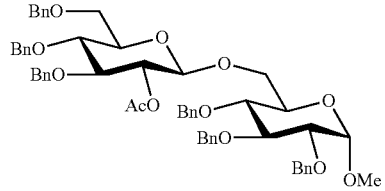

This compound was prepared by following the general experimental procedure (C) using 2-O-acetyl-3,4,6-tri-O-benzyl-β-D-glucopyranosyl fluoride (100 mg, 0.20 mmol), methyl-2,3,4-tri-O-benzyl-6-O-trimethylsilyl-α-D-glucopyranoside (119 mg, 0.22 mmol), and tris(pentafluorophenyl)borane (5.2 mg, 0.01 mmol). Purification by column chromatography eluting with ethyl acetate/hexane (1:19 to 1:3) afforded the desired product (170 mg, 0.18 mmol, 90%) as a white foam. The spectral data matched that previously reported (Koto et al., *Bull. Chem. Soc. Jpn.* 1985, 58 (1), 120-122).

2-O-(Methyl-2,3,4-tri-O-benzyl-6-O-dimethylsilyl-α-D-glucopyranosyl)-3,4,6-tri-O-benzyl-β-D-glucopyranosyl fluoride

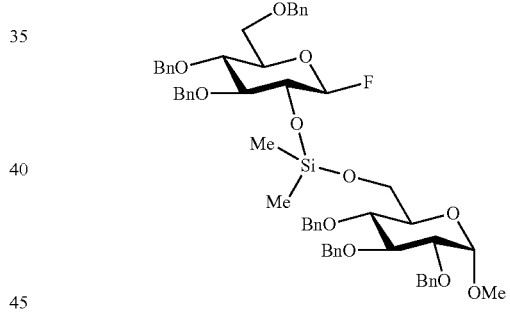

Following a literature procedure (Stork et al., *J. Am. Chem. Soc.* 1996, 118 (1), 247-248), to a stirred solution of methyl-2,3,4-tri-O-benzyl-α-D-glucopyranoside (154 mg, 0.33 mmol) in anhydrous tetrahydrofuran (3.0 mL) was added a 2.5M solution of n-butyllithium in hexanes (141 μL, 0.35 mmol) at −78° C. The reaction mixture was stirred for 0.5 h before dichlorodimethylsilane (0.2 mL, 1.66 mmol) was added rapidly in one portion at −78° C. Then the reaction was slowly allowed to warm to RT and stirring was continued for 1 h at RT. After that the reaction mixture was concentrated to dryness under reduced pressure. The residue as dissolved in anhydrous tetrahydrofuran (1.5 mL) and a solution of 3,4,6-tri-O-benzyl-β-D-glucopyranosyl fluoride (100 mg, 0.22 mmol) and imidazole (75 mg, 1.10 mmol) in anhydrous tetrahydrofuran (1.5 mL) was added at rt, and stirring was continued for 1 hour at rt. Then reaction mixture was diluted with ethyl acetate (50 mL), and ethyl acetate layer was washed with aq. NaHCO$_3$ (2×50 mL), water (50 mL), and brine (30 mL), dried over Na$_2$SO$_4$, and concentrated under reduced pressure. Purification by column chromatography eluting with ethyl acetate/hexane (1:19 to 1:4)

afforded the desired product (145 mg, 0.15 mmol, 67%) as a white foam. ¹H NMR (700 MHz, CDCl₃) δ 7.38-7.23 (m, 28H), 7.11-7.07 (m, 2H), 5.01 (dd, J=53.0, 6.9 Hz, 1H), 4.97 (d, J=10.7 Hz, 1H), 4.89 (d, J=11.3 Hz, 1H), 4.87 (d, J=11.0 Hz, 1H), 4.81 (d, J=10.8 Hz, 1H), 4.79-4.75 (m, 2H), 4.73 (d, J=10.8 Hz, 1H), 4.67-4.58 (m, 4H), 4.53 (d, J=12.2 Hz, 1H), 4.49 (d, J=10.7 Hz, 1H), 3.99 (t, J=9.3 Hz, 1H), 3.93 (dd, J=11.5, 4.0 Hz, 1H), 3.89 (dd, J=11.6, 2.0 Hz, 1H), 3.82-7.07 (m, 1H), 3.74-3.68 (m, 2H), 3.67-3.60 (m, 2H), 3.56 (t, J=9.4 Hz, 1H), 3.53-3.68 (m, 3H), 3.33 (s, 3H), 0.18 (s, 3H), 0.15 (s, 3H). ¹³C NMR (176 MHz, CDCl₃) δ 139.0, 138.7, 138.5, 138.4, 138.0, 137.9, 128.6 (2C) 128.5 (3C), 128.2 (2C) 128.1, 128.0 (2C) 127.9 (2C), 127.8, 127.7 (2C), 127.6, 109.4 (d, J=214.9 Hz), 98.1, 84.5 (d, J=10.7 Hz), 82.2, 80.2, 77.6, 77.0, 75.9, 75.5, 75.1, 75.0, 74.9 (d, J=22.7 Hz), 74.9 (d, J=4.8 Hz), 73.7, 73.5, 71.2, 68.4, 61.8, 55.1, −1.9, −2.7. ESI-HRMS m/z: Calcd. for C₅₇H₆₅FO₁₉Na [M+Na]⁺: 995.4178; found: 995.4171.

Methyl-2,3,4-tri-O-benzyl-6-O-(3,4,6-tri-O-benzyl-α-D-glucopyranosyl)-α-D-glucopyranoside (21)

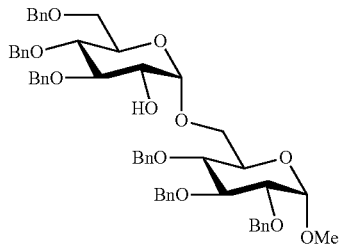

To a stirred solution of 2-O-(methyl-2,3,4-tri-O-benzyl-6-O-dimethylsilyl-α-D-glucopyranosyl)-3,4,6-tri-O-benzyl-β-D-glucopyranosyl fluoride (115 mg, 0.12 mmol) in anhydrous toluene (5.5 mL) was added a solution of tris(pentafluorophenyl) borane (3.1 mg, 0.006 mmol) in anhydrous toluene (0.5 mL) at RT. After stirring for 1 h at RT to the reaction mixture was added a 1 M solution of tetrabutylammonium fluoride in tetrahydrofuran (0.35 mL, 0.35 mmol) and stirring was continued overnight at RT. Then reaction mixture was diluted with ethyl acetate (30 mL), and ethyl acetate layer was washed with aq. NaHCO₃ (30 mL) and brine (30 mL), dried over Na₂SO₄, and concentrated under reduced pressure. Purification by column chromatography eluting with ethyl acetate/hexane (1:19 to 1:1) afforded the desired product (90 mg, 0.10 mmol, 85%) as a white foam. The spectral data matched that previously reported (Aloui et al., *Chem. Eur. J.* 2002, 8 (11), 2608-2621).

Methyl-2,3,4-tri-O-benzyl-6-O-(2-O-acetyl-3,4,6-tri-O-benzyl-α-D-mannopyranosyl)-α-D-glucopyranoside (22)

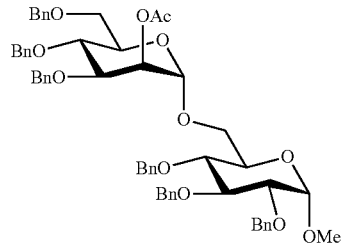

This compound was prepared by following the general experimental procedure (C) using 2-O-acetyl-3,4,6-tri-O-benzyl-α-D-mannopyranosyl fluoride (100 mg, 0.20 mmol), methyl-2,3,4-tri-O-benzyl-6-O-trimethylsilyl-α-D-glucopyranoside (119 mg, 0.22 mmol), and tris(pentafluorophenyl) borane (5.2 mg, 0.01 mmol). Purification by column chromatography eluting with ethyl acetate/hexane (1:19 to 1:3) afforded the desired product (170 mg, 0.18 mmol, 90%) as a white foam. The spectral data matched that previously reported (Ravida et al., *Org. Lett.* 2006, 8 (9), 1815-1818).

2-O-(Methyl-2,3,4-tri-O-benzyl-6-O-dimethylsilyl-α-D-glucopyranosyl)-3,4,6-tri-O-benzyl-α-D-mannopyranosyl fluoride

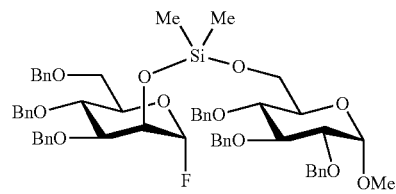

Following a literature procedure (Stork et al., *J. Am. Chem. Soc.* 1996, 118 (1), 247-248), To a stirred solution of methyl-2,3,4-tri-O-benzyl-α-D-glucopyranoside (154 mg, 0.33 mmol) in anhydrous tetrahydrofuran (3.0 mL) was added a 2.5 M solution of n-butyllithium in hexanes (141 μL, 0.35 mmol) at −78° C. The reaction mixture was stirred for 0.5 h before dichlorodimethylsilane (0.2 mL, 1.66 mmol) was added rapidly in one portion at −78° C. Then the reaction was slowly allowed to warm to RT and stirring was continued for 1 h at RT. After that the reaction mixture was concentrated to dryness under reduced pressure. The residue as dissolved in anhydrous tetrahydrofuran (1.5 mL) and a solution of 3,4,6-tri-O-benzyl-α-D-mannopyranosyl fluoride (100 mg, 0.22 mmol) and imidazole (75 mg, 1.10 mmol) in anhydrous tetrahydrofuran (1.5 mL) was added at rt, and stirring was continued for 1 hour at rt. Then reaction mixture was diluted with ethyl acetate (50 mL), and ethyl acetate layer was washed with aq. NaHCO₃ (2×50 mL), water (50 mL), and brine (30 mL), dried over Na₂SO₄, and concentrated under reduced pressure. Purification by column chromatography eluting with ethyl acetate/hexane (1:19 to 1:4) afforded the desired product (155 mg, 0.16 mmol, 72%) as a white foam. ¹H NMR (700 MHz, CDCl₃) δ 7.38-7.23 (m, 28H), 7.16-7.13 (m, 2H), 5.58 (dd, J=50.7, 2.1 Hz, 1H), 4.97 (d, J=10.8 Hz, 1H), 4.86 (d, J=11.0 Hz, 1H), 4.83-4.79 (m, 2H), 4.77 (d, J=12.0 Hz, 1H), 4.72 (d, J=11.7 Hz, 1H), 4.68-4.63 (m, 3H), 4.60-4.57 (m, 2H), 4.53 (d, J=12.1 Hz, 1H), 4.49 (d, J=10.8 Hz, 1H), 4.29 (t, J=2.5 Hz, 1H), 4.01-4.79 (m, 2H), 3.92 (ddd, J=10.0, 4.7, 1.8 Hz, 1H), 3.86 (dd, J=11.5, 2.1 Hz, 1H), 3.83 (dd, J=11.5, 4.5 Hz, 1H), 3.79 (dt, J=9.2, 2.6 Hz, 1H), 3.75 (dd, J=11.1, 4.7 Hz, 1H), 3.70 (dd, J=11.1, 1.9 Hz, 1H), 3.62 (ddd, J=10.0, 4.2, 2.1 Hz, 1H), 3.53-3.48 (m, 2H), 3.33 (s, 3H), 0.17 (s, 3H), 0.15 (s, 3H). $^{13}$C NMR (176 MHz, CDCl$_3$) δ 138.9, 138.5, 138.3 (3C), 138.2, 128.6, 128.5, 128.5 (3C), 128.4, 128.2, 128.1 (2C), 128.0, 127.9, 127.8 (3O) 127.7 (2C), 108.2 (d, J=221.6 Hz), 98.1, 82.2, 80.2, 78.9, 77.6, 75.9, 75.1, 75.0, 74.5 (d, J=1.4 Hz), 73.9, 73.5, 73.4, 72.7, 71.2, 68.8, 68.4 (d, J=37.3 Hz), 62.0, 55.2, −2.0, −2.5. $^{19}$F NMR (377 MHz, CDCl$_3$) δ −136.8 (d, J=50.6 Hz). ESI-HRMS m/z: Calcd. for $C_{57}H_{69}F_{11}N$ [M+NH$_4$]$^+$: 990.4624; found: 990.4609.

Methyl-2,3,4-tri-O-benzyl-6-O-(3,4,6-tri-O-benzyl-β-D-mannopyranosyl)-α-D-glucopyranoside (23)

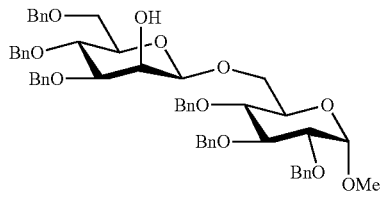

To a stirred solution of 2-O-(methyl-2,3,4-tri-O-benzyl-6-O-dimethylsilyl-α-D-glucopyranosyl)-3,4,6-tri-O-benzyl-α-D-mannopyranosyl fluoride (130 mg, 0.13 mmol) in anhydrous toluene (6 mL) was added a solution of tris (pentafluorophenyl) borane (3.6 mg, 0.007 mmol) in anhydrous toluene (0.5 mL) at RT. After stirring for 1 h at RT to the reaction mixture was added a 1M solution of tetrabutylammonium fluoride in tetrahydrofuran (0.4 mL, 0.4 mmol) and stirring was continued overnight at RT. Then reaction mixture was diluted with ethyl acetate (30 mL), and ethyl acetate layer was washed with aq. NaHCO$_3$ (30 mL) and brine (30 mL), dried over Na$_2$SO$_4$, and concentrated under reduced pressure. Purification by column chromatography eluting with ethyl acetate/hexane (1:19 to 1:1) afforded the desired product (100 mg, 0.12 mmol, 83%) as a white foam. The spectral data matched that previously reported (Stork et al., *J. Am. Chem. Soc.* 1996, 118 (1), 247-248).

Methyl-2,3,4-tri-O-benzyl-6-O-(2-O-acetyl-3,4,6-tri-O-benzyl-α-D-glucopyranosyl)-α-D-glucopyranoside

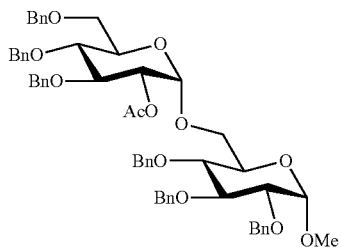

A stirred solution of methyl-2,3,4-tri-O-benzyl-6-O-(3,4,6-tri-O-benzyl-α-D-glucopyranosyl)-α-D-glucopyranoside (80 mg, 0.093 mmol) in dichloromethane (2 mL) was treated with pyridine (20 μL, 0.278 mmol) and acetic anhydride (0.02 mL, 0.185 mmol) at RT and stirring was continued overnight at RT. Then the reaction mixture was diluted with dichloromethane (10 mL), and dichloromethane layer was washed with water (2×10 mL), dried over Na$_2$SO$_4$, and concentrated under reduced pressure. Purification by column chromatography eluting with ethyl acetate/hexane (1:19 to 1:5) afforded the desired product (73 mg, 0.08 mmol, 84%) as a white foam. $^1$H NMR (700 MHz, CDCl$_3$) δ 7.38-7.21 (m, 28H), 7.15-7.10 (m, 2H), 5.13 (d, J=3.6 Hz, 1H), 4.98 (d, J=10.9 Hz, 1H), 4.87 (d, J=10.9 Hz, 1H), 4.83-4.74 (m, 6H), 4.71 (d, J=11.3 Hz, 1H), 4.66 (d, J=12.1 Hz, 1H), 4.61 4.58 (m, 2H), 4.53 (d, J=3.5 Hz, 1H), 4.49 (d, J=10.9 Hz, 1H), 4.46 (d, J=12.1 Hz, 1H), 3.96 (q, J=9.1 Hz, 2H), 3.79 (dd, J=11.9, 4.5 Hz, 2H), 3.71-3.65 (m, 4H), 3.59 (dd, J=10.9, 2.0 Hz, 1H), 3.51 (t, J=9.4 Hz, 1H), 3.41 (dd, J=9.6, 3.5 Hz, 1H), 3.33 (s, 3H), 1.87 (s, 3H). $^{13}$C NMR (176 MHz, CDCl$_3$) δ 170.2, 138.7, 138.5, 138.2 (2C), 138.0 (2C), 128.5, 128.4 (3C), 128.3 (3C), 128.1, 127.9 (2C), 127.8 (4C), 127.7 (2C), 127.6 (20), 97.7, 96.4, 82.0, 79.9 (2C), 77.8, 77.7, 75.7, 75.2, 75.0 (2C), 73.5, 73.4, 73.2, 70.5, 70.1, 68.3, 65.9, 55.0, 20.9. ESI-HRMS m/z: Calcd. for $C_{57}H_{66}O_{12}N$ [M+NH$_4$]$^+$: 956.4585; found: 956.4576.

Methyl-2,3,6-tri-O-benzyl-4-O-(2-O-acetyl-3,4-di-O-benzyl-α-L-rhamnopyranosyl)-α-D-glucopyranoside (24)

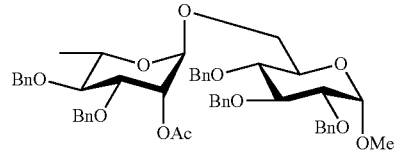

This compound was prepared by following the general experimental procedure (C) using 2-O-acetyl-3,4-di-O-benzyl-α-L-rhamnopyranosyl fluoride (105 mg, 0.27 mmol), methyl-2,3,6-tri-O-benzyl-4-O-trimethylsilyl-α-D-glucopyranoside (160 mg, 0.3 mmol), and tris(pentafluorophenyl) borane (7.0 mg, 0.01 mmol). Purification by column chromatography eluting with ethyl acetate/hexane (1:19 to 1:3) afforded the desired product (201 mg, 0.24 mmol, 89%) as a white foam. $^1$H NMR (700 MHz, CDCl$_3$) δ 7.43-7.22 (m, 25H), 5.30 (s, 1H), 5.01 (d, J=10.8 Hz, 1H), 4.95-4.88 (m, 2H), 4.85-4.77 (m, 2H), 4.70-4.65 (m, 3H), 4.62 (d, J=10.8 Hz, 1H), 4.59 (d, J=3.5 Hz, 1H), 4.55-4.52 (m, 2H), 3.99 (t, J=9.2 Hz, 1H), 3.90 (dd, J=9.4, 3.4 Hz, 1H), 3.82 (d, J=10.8 Hz, 1H), 3.77 (dd, J=9.5, 6.0 Hz, 1H), 3.72 (dd, J=10.4, 5.4 Hz, 1H), 3.52-3.47 (m, 2H), 3.45-3.39 (m, 2H), 3.35 (s, 3H), 2.15 (s, 3H), 1.30 (d, J=6.2 Hz, 3H). $^{13}$C NMR (176 MHz, CDCl$_3$) δ 170.2, 138.7, 138.4, 138.2, 138.1, 137.9, 128.5, 128.4 (4C), 128.1 (2C), 128.0 (2C), 127.9, 127.8, 127.7 (3C), 127.6, 97.8 (2C), 82.1, 80.1, 80.0, 77.8, 77.6, 75.8, 75.5, 75.0, 73.3, 71.8, 69.9, 69.1, 67.7, 66.3, 55.1, 21.1, 17.9. ESI-HRMS m/z: Calcd. for $C_{50}H_{56}O_{11}Na$ [M+Na]$^+$: 859.3715; found: 859.3720.

2-O-(Methyl-2,3,4-tri-O-benzyl-6-O-dimethylsilyl-α-D-glucopyranosyl)-3,4-di-O-benzyl-α-L-rhamnopyranosyl fluoride (S35)

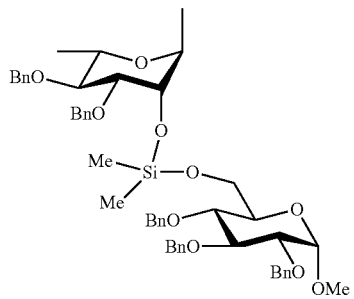

Adapting a literature procedure (Stork et al., *J. Am. Chem. Soc.* 1996, 118 (1), 247-248), to a stirred solution of methyl-2,3,4-tri-O-benzyl-α-D-glucopyranoside (151 mg, 0.33 mmol) in anhydrous tetrahydrofuran (3.0 mL) was added a 2.5 M solution of n-butyllithium in hexanes (139 μL, 0.35 mmol) at −78° C. The reaction mixture was stirred for 0.5 h before dichlorodimethylsilane (0.2 mL, 1.63 mmol) was added rapidly in one portion at −78° C. Then the reaction was slowly allowed to warm to rt and stirring was continued for 1 h at rt. After that the reaction mixture was concentrated to dryness under reduced pressure. The residue as dissolved in anhydrous tetrahydrofuran (1.5 mL) and a solution of 3,4-di-O-benzyl-α-L-rhamnopyranosyl fluoride (75 mg, 0.22 mmol) and imidazole (74 mg, 1.08 mmol) in anhydrous tetrahydrofuran (1.5 mL) was added at RT, and stirring was continued for 1 hour at RT. Then reaction mixture was diluted with ethyl acetate (50 mL), and ethyl acetate layer was washed with aq. NaHCO₃ (2×50 mL), water (50 mL), and brine (30 mL), dried over Na₂SO₄, and concentrated under reduced pressure. Purification by column chromatography eluting with ethyl acetate/hexane (1:19 to 1:4) afforded the desired product (130 mg, 0.15 mmol, 69%) as a white foam. $^1$H NMR (700 MHz, CDCl₃) δ 7.42-7.28 (m, 26H), 5.56 (dd, J=50.7, 2.0 Hz, 1H), 5.03 (d, J=10.8 Hz, 1H), 4.95-4.91 (m, 2H), 4.87 (d, J=10.8 Hz, 1H), 4.82 (d, J=12.0 Hz, 1H), 4.77 (d, J=11.6 Hz, 1H), 4.73-4.69 (m, 2H), 4.68-4.64 (m, 3H), 4.35 (t, J=2.4 Hz, 1H), 4.05 (t, J=9.2 Hz, 1H), 3.95-3.89 (m, 3H), 3.79 (dt, J=9.5, 2.5 Hz, 1H), 3.68 (dt, J=10.0, 2.9 Hz, 1H), 3.64-3.60 (m, 2H), 3.55 (dd, J=9.6, 3.5 Hz, 1H), 3.41 (s, 3H), 1.38 (d, J=6.2 Hz, 3H), 0.22 (s, 3H), 0.21 (s, 3H). $^{13}$C NMR (176 MHz, CDCl₃) δ 138.9, 138.5, 138.4, 138.2, 128.5, 128.5, 128.4, 128.4, 128.4, 128.1, 128.1, 128.0, 127.9, 127.9, 127.8, 127.8, 127.8, 127.7, 127.7, 108.2 (d, J=220.4 Hz), 98.0, 82.1, 80.2, 79.2, 78.9 (d, J=1.8 Hz), 77.4, 75.8, 75.3, 75.0, 73.4, 72.6, 71.1, 70.8 (d, J=2.0 Hz), 68.6 (d, J=37.9 Hz), 61.7, 55.1, 18.0, −1.9, −2.3. $^{19}$F NMR (377 MHz, CDCl₃) δ−136.1 (d, J=50.4 Hz). ESI-HRMS m/z: Calcd. for C₅₀H₆₃FO₁₀NSi [M+NH₄]⁺: 884.4205; found: 884.4202.

Methyl-2,3,4-tri-O-benzyl-6-O-(2-O-acetyl-3,4-di-O-benzyl-β-L-rhamnopyranosyl)-α-D-glucopyranoside (25)

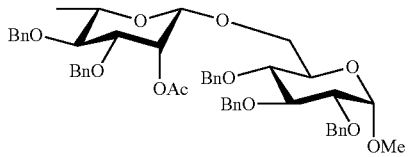

To a stirred solution of 2-O-(Methyl-2,3,4-tri-O-benzyl-6-O-dimethylsilyl-α-D-glucopyranosyl)-3,4-di-O-benzyl-α-L-rhamnopyranosyl fluoride (75 mg, 0.09 mmol) in anhydrous toluene (4 mL) was added a solution of tris(pentafluorophenyl) borane (2.2 mg, 0.004 mmol) in anhydrous toluene (0.5 mL) at RT. After stirring for 1 h at RT to the reaction mixture was added a 1 M solution of tetrabutylammonium fluoride in tetrahydrofuran (0.5 mL, 0.5 mmol) and stirring was continued for 3 additional hours at RT. Then reaction mixture was diluted with ethyl acetate (30 mL), and ethyl acetate layer was washed with aq. NaHCO₃ (30 mL) and brine (30 mL), dried over Na₂SO₄, and concentrated under reduced pressure. The crude residue was dissolved in anhydrous dichloromethane (1.0 ml) to which was added pyridine (0.5 ml) and acetic anhydride (0.5 ml) and stirred overnight. Reaction mixture was concentrated to dryness and purification by column chromatography eluting with ethyl acetate/hexane (1:19 to 1:1) afforded the desired product (48 mg, 0.06 mmol, 67%) as a white foam. $^1$H NMR (700 MHz, CDCl₃) δ 7.42-7.29 (m, 25H), 5.68 (d, J=3.2 Hz, 1H), 4.99 (d, J=11.0 Hz, 1H), 4.94 (d, J=10.8 Hz, 1H), 4.89-4.83 (m, 3H), 4.77 (d, J=11.3 Hz, 1H), 4.70 (d, J=1.7 Hz, 1H), 4.69 (d, J=3.5 Hz, 1H), 4.62 (d, J=10.8 Hz, 1H), 4.61-4.58 (m, 2H), 4.51 (d, J=11.3 Hz, 1H), 4.19 (dd, J=11.5, 3.6 Hz, 1H), 3.98 (t, J=9.3 Hz, 1H), 3.74-3.69 (m, 2H), 3.63 (dd, J=8.9, 3.2 Hz, 1H), 3.58-3.55 (m, 2H), 3.44-3.38 (m, 2H), 3.36 (s, 3H), 2.15 (s, 3H), 1.39 (d, J=5.8 Hz, 3H). $^{13}$C NMR (176 MHz, CDCl₃) δ 170.3, 138.9, 138.4, 138.3, 138.2, 137.6, 128.5, 128.4, 128.4, 128.4, 128.4, 128.3, 128.2, 128.1, 128.0, 128.0, 127.9, 127.8, 127.8, 127.8, 127.6, 98.6, 98.2, 82.0, 80.1, 80.0, 79.8, 77.8, 75.8, 75.4, 75.2, 73.6, 71.7, 71.3, 70.0, 68.1, 67.1, 55.1, 21.1, 18.0. ESI-HRMS m/z: Calcd. for C₅₀H₅₄O₁₁N [M+NH₄]⁺: 850.4161; found: 850.4164.

Methyl-2,3-di-O-benzyl-4-O-(2-O-acetyl-3,4,6-tri-O-benzyl-α-D-mannopyranosyl)-6-O-(2-O-acetyl-3,4,6-tri-O-benzyl-β-D-glucopyranosyl)-α-D-glucopyranoside (31a)

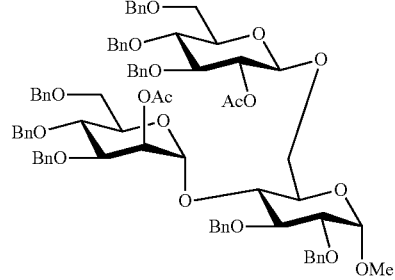

To a stirred solution of 2-O-acetyl-3,4,6-tri-O-benzyl-α-D-mannopyranosyl fluoride (50 mg, 0.10 mmol) and methyl-2,3,-di-O-benzyl-4-O-trimethylsilyl-6-O-tert-butyldimethylsilyl-α-D-glucopyranoside (57 mg, 0.10 mmol) in anhydrous toluene (2.0 mL) was added a solution of tris(pentafluorophenyl) borane (2.6 mg, 0.005 mmol) in anhydrous toluene (0.5 mL) at RT. After stirring for 0.5 h at RT to the reaction mixture was added a solution of 2-O-acetyl-3,4,6-tri-O-benzyl-β-D-glucopyranosyl fluoride (50 mg, 0.10 mmol) in anhydrous toluene (0.5 mL) and stirring was continued for additional 1.5 h at RT. Then the reaction mixture was concentrated to dryness under reduced pressure. Purification by column chromatography eluting with ethyl acetate/hexane (1:19 to 1:1) afforded the desired product (82 mg, 0.061 mmol, 61%) as a white foam. $^1$H NMR (700 MHz, CDCl$_3$) δ 7.39-7.24 (m, 36H), 7.23-7.14 (m, 4H), 5.48 (br s, 1H), 5.31 (br s, 1H), 5.07-5.02 (m, 2H), 4.86 (d, J=10.8 Hz, 1H), 4.82-7.14 (m, 3H), 4.71 (d, J=12.1 Hz, 1H), 4.68 (d, J=11.4 Hz, 1H), 4.66 (d, J=12.2 Hz, 1H), 4.63 (d, J=11.0 Hz, 1H), 4.60-4.54 (m, 4H), 4.49 (t, J=10.8 Hz, 2H), 4.46-4.41 (m, 3H), 4.12 (dd, J=10.8, 1.8 Hz, 1H), 3.96-3.88 (m, 3H), 3.84 (t, J=9.5 Hz, 1H), 3.80 (dd, J=10.7, 4.3 Hz, 1H), 3.77-3.70 (m, 4H), 3.65 (dt, J=14.2, 4.1 Hz, 4H), 3.53 (dd, J=9.6, 3.5 Hz, 1H), 3.40 (dd, J=8.1, 4.7 Hz, 1H), 3.38 (s, 3H), 2.02 (s, 3H), 1.97 (s, 3H). $^{13}$C NMR (176 MHz, CDCl$_3$) δ 169.7, 169.5, 138.6, 138.4 (20) 138.3 (2C), 138.1, 138.0 (2C), 128.5 (3C), 128.4 (40) 128.3, 128.2 (2C), 128.0 (3C), 127.9, 127.8 (2C), 127.7 (3C), 127.6, 127.3 (2C), 101.2, 100.0, 97.6, 83.1, 81.5, 80.1, 78.2, 78.0, 77.6, 75.3 (2C) 75.2, 75.0 (2C) 74.2, 73.5, 73.4, 73.3, 73.2, 72.6, 71.8, 69.6, 69.2, 68.9, 68.8, 68.5, 55.2, 21.0. The stereochemistry at the anomeric linkages was confirmed by extracting the $^1$J[$^{13}$CH(1)] coupling constant and was found to be consistent with the proposed structure. Proton coupled $^{13}$C NMR (176 MHz, CDCl$_3$) δ 101.2 (161 Hz, β-glucoside), 100.0 (172 Hz, α-mannoside), 97.6 (168 Hz, α-glucoside). ESI-HRMS m/z: Calcd. for C$_{79}$H$_{90}$O$_{18}$N [M+NH$_4$]$^+$: 1340.6158; found: 1340.6151.

4-Penten-1-yl-2-O-acetyl-3-O-benzyl-4-O-(2-O-acetyl-3,4,6-tri-O-benzyl-α-D-mannopyranosyl)-6-O-(2-O-acetyl-3,4,6-tri-O-benzyl-β-D-glucopyranosyl)-β-D-glucopyranoside (31b)

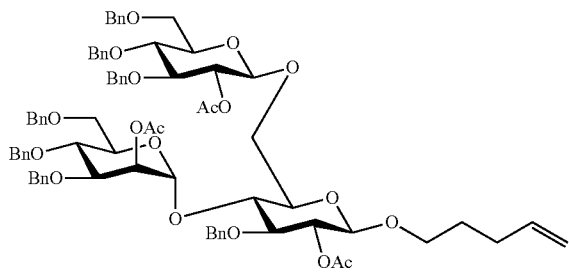

To a stirred solution of 2-O-acetyl-3,4,6-tri-O-benzyl-α-D-mannopyranosyl fluoride (100 mg, 0.20 mmol) and 4-penten-1-yl-2-O-acetyl-3-O-benzyl-4-O-trimethylsilyl-6-O-tert-butyldimethylsilyl-α-D-glucopyranoside (115 mg, 0.20 mmol) in anhydrous toluene (4.5 mL) was added a solution of tris(pentafluorophenyl) borane (5.2 mg, 0.01 mmol) in anhydrous toluene (0.5 mL) at RT. After stirring for 0.5 h at RT to the reaction mixture was added a solution of 2-O-acetyl-3,4,6-tri-O-benzyl-β-D-glucopyranosyl fluoride (100 mg, 0.20 mmol) in anhydrous toluene (1.0 mL) and stirring was continued for additional 1.5 h at RT. Then the reaction mixture was concentrated to dryness under reduced pressure. Purification by column chromatography eluting with ethyl acetate/hexane (1:19 to 1:2) afforded the desired product (113 mg, 0.085 mmol, 42%) as a white foam. $^1$H NMR (700 MHz, CDCl$_3$) δ 7.35-7.22 (m, 31H), 7.18-7.13 (m, 4H), 5.79 (ddt, J=16.9, 10.2, 6.6 Hz, 1H), 5.45 (dd, J=2.9, 1.8 Hz, 1H), 5.29 (d, J=1.9 Hz, 1H), 5.04-4.93 (m, 4H), 4.82 (d, J=10.8 Hz, 1H), 4.77 (d, J=11.4 Hz, 1H), 4.76-4.72 (m, 2H), 4.67 (d, J=11.0 Hz, 1H), 4.65-4.60 (m, 3H), 4.52-4.44 (m, 5H), 4.41 (d, J=8.0 Hz, 1H), 4.34-4.29 (m, 2H), 4.11 (dd, J=11.4, 2.1 Hz, 1H), 3.90-3.79 (m, 4H), 3.78-3.59 (m, 8H), 3.58-3.50 (m, 2H), 3.45-3.39 (m, 1H), 3.33 (dt, J=10.0, 2.9 Hz, 1H), 2.13-2.02 (m, 2H), 2.00 (s, 3H), 1.93 (s, 3H), 1.91 (s, 3H), 1.77-1.52 (m, 2H). $^{13}$C NMR (176 MHz, CDCl$_3$) δ 170.1, 169.5, 138.5, 138.3, 138.2, 138.1, 138.0, 137.9, 128.5 (5C), 128.4 (2C), 128.2, 128.1, 128.0, 127.9, 127.8 (2C), 127.7 (2C), 127.6, 127.5, 115.1, 101.2, 100.7, 99.5, 83.4, 83.0, 78.3, 77.9, 76.1, 75.3, 75.2, 75.1, 75.0, 74.8, 74.6, 74.1, 73.6, 73.4, 73.2, 73.1, 72.9, 72.1, 69.0, 68.9, 68.8 (2C), 68.6, 30.0, 28.8, 21.1 (2C), 20.9. The stereochemistry at the anomeric linkages was confirmed by extracting the $^1$J[$^{13}$CH(1)] coupling constant and was found to be consistent with the proposed structure. Proton coupled $^{13}$C NMR (176 MHz, CDCl$_3$) δ 101.2 (161 Hz, β-glucoside), 100.7 (160 Hz, β-glucoside), 99.5 (174 Hz, α-mannoside). ESI-HRMS m/z: Calcd. for C$_{78}$H$_{88}$O$_{19}$Na [M+Na]$^+$: 1351.5818; found: 1351.5805.

Methyl-2,3-di-O-benzyl-4-O-(2-O-acetyl-3,4,6-tri-O-benzyl-β-D-glucopyranosyl)-6-O-(2-O-acetyl-3,4,6-tri-O-benzyl-α-D-mannopyranosyl)-α-D-glucopyranoside (33)

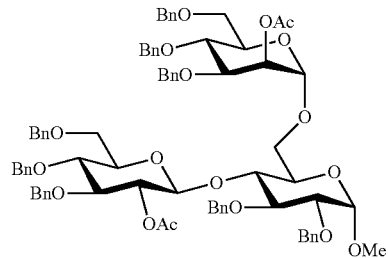

To a stirred solution of 2-O-acetyl-3,4,6-tri-O-benzyl-β-D-glucopyranosyl fluoride (50 mg, 0.10 mmol) and methyl-2,3,-di-O-benzyl-4-O-trimethylsilyl-6-O-tert-butyldimethylsilyl-α-D-glucopyranoside (57 mg, 0.10 mmol) in anhydrous toluene (2.0 mL) was added a solution of tris(pentafluorophenyl) borane (2.6 mg, 0.005 mmol) in anhydrous toluene (0.5 mL) at RT. After stirring for 0.5 h at RT to the reaction mixture was added a solution of 2-O-acetyl-3,4,6-tri-O-benzyl-α-D-mannopyranosyl fluoride (50 mg, 0.10 mmol) in anhydrous toluene (0.5 mL) and stirring was continued for additional 1.5 h at RT. Then the reaction mixture was concentrated to dryness under reduced pressure. Purification by column chromatography eluting with ethyl acetate/hexane (1:19 to 1:1) afforded the desired product (65 mg, 0.049 mmol, 48%) as a white foam. $^1$H NMR (700 MHz, CDCl$_3$) δ 7.38-7.20 (m, 36H), 7.20-7.15 (m, 4H), 5.39 (dd, J=2.9, 1.9 Hz, 1H), 5.05 (d, J=11.5 Hz, 1H), 5.01 (dd, J=9.6, 8.0 Hz, 1H), 4.97 (d, J=1.8 Hz, 1H), 4.89 (d, J=10.9 Hz, 1H), 4.85 (d, J=11.5 Hz, 1H), 4.76-4.71

(m, 2H), 4.72 (d, J=11.2 Hz, 1H), 4.70 (d, J=11.2 Hz, 1H), 4.67 (d, J=12.1 Hz, 1H), 4.64-4.60 (m, 2H), 4.58-4.49 (m, 6H), 4.40 (d, J=12.2 Hz, 1H), 4.36 (d, J=12.1 Hz, 1H), 3.97-3.90 (m, 3H), 3.88-3.84 (m, 1H), 3.82-3.67 (m, 2H), 3.73-3.67 (m, 5H), 3.64-3.60 (m, 2H), 3.50-3.45 (m, 2H), 3.40 (ddd, J=10.1, 4.9, 2.0 Hz, 1H), 3.31 (s, 3H), 2.16 (s, 3H), 1.91 (s, 3H). $^{13}$C NMR (176 MHz, CDCl$_3$) δ 170.3, 169.5, 139.6, 138.5, 138.4, 138.3 (3C), 138.1, 137.9, 128.5 (3C), 128.4 (2C), 128.2 (2C), 128.1 (3C), 127.9 (2C), 127.8 (3C), 127.7 (3C), 127.5, 127.4, 127.1, 100.8, 98.2, 97.9, 83.3, 80.0, 79.6, 78.2, 78.1, 77.8, 75.5, 75.3, 75.2 (2C), 75.0, 74.3, 73.8, 73.6, 73.5, 73.4, 71.8, 71.7, 69.6, 69.0, 68.7, 68.5, 65.6, 55.2, 21.2, 21.0. The stereochemistry at the anomeric linkages was confirmed by extracting the $^1$J[$^{13}$CH(1)] coupling constant and was found to be consistent with the proposed structure. Proton coupled $^{13}$C NMR (176 MHz, CDCl$_3$) δ 100.8 (159 Hz, β-glucoside), 98.2 (172 Hz, α-mannoside), 97.9 (169 Hz, α-glucoside). ESI-HRMS m/z: Calcd. for C$_{79}$H$_{86}$O$_{18}$Na [M+Na]$^+$: 1345.5712; found: 1345.5712.

Methyl-2,4,6-tri-O-benzyl-3-O-[2-O-acetyl-3-O-benzyl-4-O-(2-O-acetyl-3,4,6-tri-O-benzyl-α-D-mannopyranosyl)-6-O-benzoyl-α-D-mannopyranosyl]-α-D-glucopyranoside (32a)

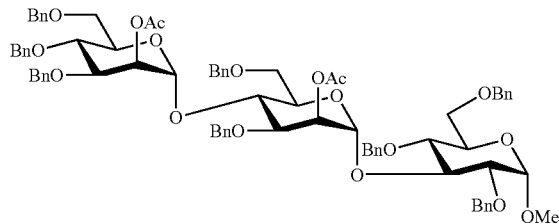

A round bottom flask was charged with 2-O-acetyl-3-O-benzyl-4-O-triethylsilyl-6-O-benzoyl-α-D-mannopyranosyl fluoride (100 mg, 0.19 mmol), methyl-2,4,6-tri-O-benzyl-3-O-trimethylsilyl-α-D-glucopyranoside (101 mg, 0.19 mmol), and 2,6-di-tert-butyl-4-methylpyridine (4.1 mg, 0.02). Then the mixture was co-evaporated with toluene three times and then dried under reduced pressure overnight. Then to the mixture was added anhydrous toluene (3.5 mL) followed by addition of a solution of tris(pentafluorophenyl)borane (10.2 mg, 0.02 mmol) in anhydrous toluene (0.5 mL) at RT. After stirring for 0.5 h at RT to the reaction mixture was added a solution of 2-O-acetyl-3,4,6-tri-O-benzyl-α-D-mannopyranosyl fluoride (104 mg, 0.21 mmol) in anhydrous toluene (1.0 mL) and stirring was continued for additional 1.5 h at RT. Then the reaction mixture was concentrated to dryness under reduced pressure. Purification by column chromatography eluting with ethyl acetate/hexane (1:19 to 1:2) afforded the desired product (125 mg, 0.093 mmol, 50%) as a white foam. $^1$H NMR (700 MHz, CDCl$_3$) δ 8.17 (d, J=7.5 Hz, 2H), 7.60 (t, J=7.5 Hz, 1H), 7.47 (t, J=7.6 Hz, 2H), 7.45-7.25 (m, 31H), 7.23-7.20 (m, 4H), 5.65 (dd, J=3.2, 1.9 Hz, 1H), 5.58 (dd, J=3.1, 1.9 Hz, 1H), 5.53 (d, J=1.8 Hz, 1H), 5.38 (d, J=1.8 Hz, 1H), 4.87 (d, J=10.9 Hz, 1H), 4.85 (d, J=3.5 Hz, 1H), 4.81 (d, J=10.9 Hz, 1H), 4.80 (d, J=10.7 Hz, 1H), 4.76 (d, J=10.9 Hz, 1H), 4.70 (d, J=12.0 Hz, 1H), 4.64 (d, J=11.6 Hz, 1H), 4.62-4.46 (m, 9H), 4.28 (t, J=9.6 Hz, 1H), 4.26-4.21 (m, 2H), 4.13-4.07 (m, 2H), 4.00 (t, J=9.6 Hz, 1H), 3.91 (dd, J=9.5, 3.2 Hz, 1H), 3.84-3.75 (m, 4H), 3.74-3.68 (m, 2H), 3.54 (dd, J=9.8, 3.5 Hz, 1H), 3.43 (s, 3H), 3.43-3.40 (m, 1H), 2.10 (s, 3H), 2.07 (s, 3H). $^{13}$C NMR (176 MHz, CDCl$_3$) δ 170.0, 169.9, 166.2, 138.6, 138.3, 138.1, 137.8, 137.7, 137.5, 137.4, 132.9, 130.4, 129.9, 128.6 (3C), 128.5, 128.4 (2C), 128.3 (4C), 128.2, 128.1, 128.0, 127.9, 127.8 (3C), 127.7, 127.6, 127.5 (2C), 99.7, 97.8, 97.4, 79.1, 78.2, 78.1, 77.6, 76.2, 75.0, 74.5, 73.8, 73.7, 73.4, 72.7, 72.3, 72.2, 71.8, 71.3, 69.7, 69.0, 68.7, 68.3, 68.2, 67.9, 63.7, 55.2, 21.1, 20.8. The stereochemistry at the anomeric linkages was confirmed by extracting the $^1$J[$^{13}$CH(1)] coupling constant and was found to be consistent with the proposed structure. Proton coupled $^{13}$C NMR (176 MHz, CDCl$_3$) δ 99.7 (174 Hz, α-mannoside), 97.8 (174 Hz, α-mannoside), 97.4 (167 Hz, α-glucoside). ESI-HRMS m/z: Calcd. for C$_{79}$H$_{84}$O$_{19}$Na [M+]$^+$: 1359.5505; found: 1359.5498.

Methyl-2,4,6-tri-O-benzyl-3-O-[2-O-acetyl-3-O-benzyl-4-O-(2-O-acetyl-3,4,6-tri-O-benzyl-α-D-mannopyranosyl)-6-O-triisopropylsilyl-α-D-mannopyranosyl]-α-D-glucopyranoside (32b)

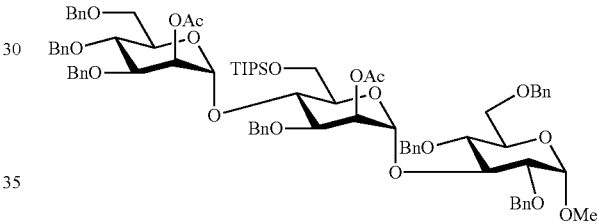

A round bottom flask was charged with 2-O-acetyl-3-O-benzyl-4-O-triethylsilyl-6-O-triisopropylsilyl-α-D-mannopyranosyl fluoride (170 mg, 0.29 mmol), methyl-2,4,6-tri-O-benzyl-3-O-trimethylsilyl-α-D-glucopyranoside (156 mg, 0.29 mmol), and 2,6-di-tert-butyl-4-methylpyridine (6.2 mg, 0.03). Then the mixture was co-evaporated with toluene three times and then dried under reduced pressure overnight. Then to the mixture was added anhydrous toluene (5.0 mL) followed by addition of a solution of tris(pentafluorophenyl)borane (15.2 mg, 0.03 mmol) in anhydrous toluene (0.5 mL) at RT. After stirring for 0.5 h at RT to the reaction mixture was added a solution of 2-O-acetyl-3,4,6-tri-O-benzyl-α-D-mannopyranosyl fluoride (144 mg, 0.29 mmol) in anhydrous toluene (1.0 mL) and stirring was continued for additional 1.5 h at RT. Then the reaction mixture was concentrated to dryness under reduced pressure. Purification by column chromatography eluting with ethyl acetate/hexane (1:19 to 1:3) afforded the desired product (160 mg, 0.115 mmol, 40%) as a white foam. $^1$H NMR (700 MHz, CDCl$_3$) δ 7.43-7.15 (m, 35H), 5.59 (br s, 1H), 5.54 (br s, 1H), 5.48 (br s, 1H), 5.32 (br s, 1H), 4.88 (d, J=11.0 Hz, 1H), 4.78-4.64 (m, 6H), 4.60 (d, J=11.9 Hz, 1H), 4.58-4.50 (m, 4H), 4.47 (d, J=12.1 Hz, 1H), 4.43 (d, J=10.6 Hz, 1H), 4.39 (d, J=11.1 Hz, 1H), 4.27 (t, J=9.5 Hz, 1H), 4.16 (t, J=9.2 Hz, 1H), 4.05 (t, J=9.7 Hz, 1H), 4.02-3.98 (m, 2H), 3.91 (dd, J=9.5, 3.2 Hz, 1H), 3.87 (dd, J=11.0, 2.9 Hz, 1H), 3.83-3.64 (m, 8H), 3.45 (dd, J=9.6, 3.6 Hz, 1H), 3.38 (s, 3H), 2.09 (s, 3H), 1.97 (s, 3H), 1.15-1.01 (m, 21H). $^{13}$C NMR (176 MHz, CDCl$_3$) δ 170.2 (2C), 138.9, 138.5, 138.2, 137.9, 137.8, 137.7, 137.6, 128.6 (2C), 128.5 (2C), 128.4 (2C), 128.3 (2C), 128.2, 128.1, 128.0, 127.9 (2C), 127.7, 127.6 (3C), 127.5, 127.4 (2C), 98.7, 97.6, 97.5, 79.2, 78.3, 78.2, 77.7, 75.8, 74.9, 74.3, 73.9, 73.7 (2C), 72.7, 72.4, 72.1, 71.7, 71.1, 70.6, 69.6, 68.7, 68.6, 68.4, 67.9, 62.4, 55.2, 21.1, 20.7, 18.1, 18.0, 12.2. ESI-HRMS m/z: Calcd. for $C_{81}H_{104}O_{18}NSi$ [M NH$_4$]$^+$: 1406.7023; found: 1406.7014.

Methyl-2,4,6-tri-O-benzyl-3-O-[2-O-acetyl-3-O-benzyl-4-O-(2-O-acetyl-3,4,6-tri-O-benzyl-α-D-mannopyranosyl)-α-D-mannopyranosyl]-α-D-glucopyranoside (32c)

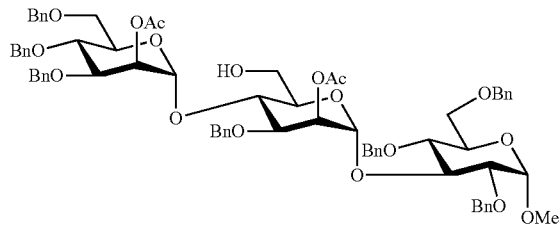

To a stirred solution of methyl-2,4,6-tri-O-benzyl-3-O-[2-O-acetyl-3-O-benzyl-4-O-(2-O-acetyl-3,4,6-tri-O-benzyl-α-D-mannopyranosyl)-6-O-triisopropylsilyl-α-D-mannopyranosyl]-α-D-glucopyranoside (150 mg, 0.108 mmol) in anhydrous tetrahydrofuran (1.5 mL) was added a 1 M solution of tetrabutylammonium fluoride in tetrahydrofuran (0.32 mL, 0.32 mmol) at RT and stirring was continued for 24 h at RT. Then the reaction mixture was diluted with ethyl acetate (50 mL) and ethyl acetate layer was washed with water (2×50 mL) and brine (50 mL), dried over Na$_2$SO$_4$, and concentrated under reduced pressure. Purification by column chromatography eluting with ethyl acetate/hexane (1:19 to 1:1) afforded the desired product (100 mg, 0.081 mmol, 75%) as a white foam. $^1$H NMR (700 MHz, CDCl$_3$) δ 7.41-7.12 (m, 35H), 5.57 (dd, J=3.2, 1.8 Hz, 1H), 5.53 (dd, J=3.3, 1.7 Hz, 1H), 5.38 (d, J=1.8 Hz, 1H), 5.34 (br s, 1H), 4.85 (d, J=10.9 Hz, 1H), 4.76 (d, J=11.1 Hz, 1H), 4.74 (d, J=3.5 Hz, 1H), 4.71 (d, J=11.0 Hz, 1H), 4.70 (d, J=10.5 Hz, 1H), 4.65 (d, J=12.0 Hz, 1H), 4.62 (d, J=12.3 Hz, 1H), 4.57-4.53 (m, 4H), 4.52 (d, J=12.0 Hz, 1H), 4.48-4.43 (m, 3H), 4.18-4.13 (m, 2H), 4.06 (dt, J=10.0, 2.5 Hz, 1H), 3.96 (dd, J=9.4, 3.3 Hz, 1H), 3.84 (dd, J=9.2, 3.2 Hz, 1H), 3.80-3.63 (m, 8H), 3.63-3.54 (m, 2H), 3.47 (dd, J=9.7, 3.5 Hz, 1H), 3.38 (s, 3H), 2.67 (br s, 1H), 2.06 (s, 3H), 2.01 (s, 3H). $^{13}$C NMR (176 MHz, CDCl$_3$) δ 170.2, 169.9, 138.3, 138.0, 137.8 (2C), 137.7, 137.6, 137.5, 128.6 (3C), 128.5, 128.4 (4C), 128.3 (2C), 128.1 (3C), 127.9 (2C), 127.8 (2C), 127.7, 127.6, 127.4, 99.6, 98.2, 97.5, 79.1, 78.4, 78.2, 77.7, 76.2, 75.1, 74.4, 74.3, 73.7, 73.5, 72.7, 72.5, 71.8, 71.4, 71.3, 71.2, 69.7, 68.9, 68.6, 68.3, 68.0, 60.8, 55.2, 21.0, 20.9. The stereochemistry at the anomeric linkages was confirmed by extracting the $^1J[^{13}CH(1)]$ coupling constant and was found to be consistent with the proposed structure. Proton coupled $^{13}$C NMR (176 MHz, CDCl$_3$) δ 99.6 (175 Hz, α-mannoside), 98.2 (174 Hz, α-mannoside), 97.5 (168 Hz, α-glucoside). ESI-HRMS m/z: Calcd. for $C_{72}H_{84}O_{18}N$ [M+NH$_4$]$^+$: 1250.5688; found: 1250.5672.

Methyl-2,4,6-tri-O-benzyl-3-O-[2-O-acetyl-3-O-benzyl-4-O-(2-O-acetyl-3,4,6-tri-O-benzyl-α-D-mannopyranosyl)-6-O-[2-O-acetyl-3-O-benzyl-4-O-(2-O-acetyl-3,4,6-tri-O-benzyl-α-D-mannopyranosyl)-6-O-(2-O-acetyl-3,4,6-tri-O-benzyl-β-D-glucopyranosyl)-β-D-glucopyranosyl]-α-D-mannopyranosyl]-α-D-glucopyranoside (34)

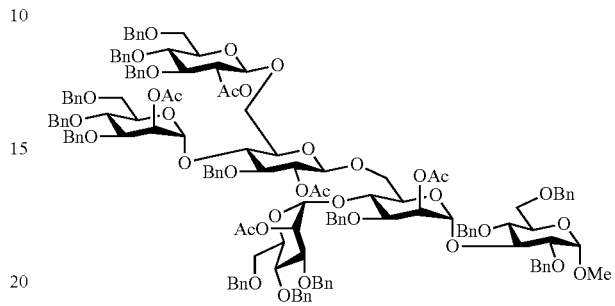

A flask was charged with methyl-2,4,6-tri-O-benzyl-3-O-[2-O-acetyl-3-O-benzyl-4-O-(2-O-acetyl-3,4,6-tri-O-benzyl-α-D-mannopyranosyl)-α-D-mannopyranosyl]-α-D-glucopyranoside (90 mg, 0.073 mmol) and 4-penten-1-yl-2-O-acetyl-3-O-benzyl-4-O-(2-O-acetyl-3,4,6-tri-O-benzyl-α-D-mannopyranosyl)-6-O-(2-O-acetyl-3,4,6-tri-O-benzyl-β-D-glucopyranosyl)-β-D-glucopyranoside (126 mg, 0.095 mmol). The mixture was co-evaporated with toluene three times and dried under high vacuum overnight. Then to the flask was added freshly activated 4 Å molecular sieves, and it was evacuated and backfilled with nitrogen three times. Then to the mixture was added anhydrous dichloromethane (1.5 mL) and the mixture was stirred for 1 hour at rt. Then to the reaction mixture was added N-iodosuccinimide (33 mg, 0.146 mmol) at rt and the reaction was immediately cooled to −20° C. before the addition of triethylsilyl trifluoromethanesulfonate (5 μL, 0.022 mmol) and stirring was continued for 2 hours at −20° C. Then the temperature was raised up to 0° C. and stirring was continued for 1 hour before it was quenched by the addition of aq. NaHCO$_3$ (5 mL) and aq. Na$_2$S$_2$O$_3$ (5 mL). After that reaction mixture was filtered to remove insoluble materials and extracted with dichloromethane (3×20 mL). Combined dichloromethane layer was washed with water (20 mL), dried over Na$_2$SO$_4$, and concentrated under reduced pressure. Purification by column chromatography eluting with ethyl acetate/hexane (1:19 to 1:2) afforded the desired product (110 mg, 0.044 mmol, 61%) as a white foam. $^1$H NMR (700 MHz, CDCl$_3$) δ 7.40-7.05 (m, 70H), 5.52 (br s, 1H), 5.44 (br s, 1H), 5.41 (br s, 1H), 5.37 (br s, 1H), 5.27 (br s, 1H), 5.19 (br s, 1H), 5.10 (t, J=8.7 Hz, 1H), 4.98 (t, J=8.8 Hz, 1H), 4.82 (d, J=10.8 Hz, 1H), 4.81 (d, J=10.9 Hz, 1H), 4.73 (d, J=11.3 Hz, 1H), 4.72-4.54 (m, 13H), 4.52 (d, J=12.3 Hz, 1H), 4.50-4.42 (m, 11H), 4.38 (d, J=7.9 Hz, 1H), 4.28-4.24 (m, 2H), 4.21 (d, J=12.2 Hz, 1H), 4.18 (d, J=9.4 Hz, 1H), 4.11-4.09 (m, 1H), 4.03 (t, J=9.5 Hz, 1H), 4.02 (d, J=11.8 Hz, 1H), 3.99 (t, J=9.2 Hz, 1H), 3.95 (dd, J=9.2, 2.8 Hz, 1H), 3.89-3.74 (m, 6H), 3.73-3.53 (m, 14H), 3.51 (d, J=10.5 Hz, 1H), 3.44-3.40 (m, 1H), 3.33 (dd, J=9.8, 3.3 Hz, 1H), 3.26 (dt, J=9.9, 2.6 Hz, 1H), 3.19 (s, 3H), 2.07 (s, 3H), 2.02 (s, 3H), 1.98 (s, 3H), 1.98 (s, 3H), 1.88 (s, 3H). $^{13}$C NMR (176 MHz, CDCl$_3$) δ 170.7, 170.1, 170.0, 169.6, 169.4, 138.7 (2C), 138.5 (2C), 138.4 (3C), 138.1 (2C), 137.9 (3C), 137.7, 128.7, 128.6, 128.5 (4C), 128.4 (6C), 128.3 (4C), 128.2 (2C), 128.1 (2C), 128.0, 127.9 (2C), 127.8 (4C), 127.7 (4C), 127.6 (2C), 127.5 (2C), 101.2, 100.6, 100.2, 99.4, 97.6, 97.5, 83.6, 83.1, 79.4, 78.5, 78.4, 77.7, 77.2, 76.1, 75.7, 75.3, 75.2 (3C), 75.0, 74.9, 74.7, 74.4, 74.2, 74.1, 73.9, 73.8 (2C), 73.7, 73.5, 73.4, 73.0, 72.9 (2C), 72.6, 72.4, 72.1, 71.7, 70.8, 70.4, 69.8, 69.2, 69.1, 69.0 (3C), 68.6, 68.4, 67.9, 67.2, 55.0, 21.2, 21.1 (2C), 20.9, 20.8. The stereochemistry at the anomeric linkages was confirmed by extracting the $^1J[^{13}CH(1)]$ coupling constant and was found to be consistent with the proposed structure. Proton coupled $^{13}C$ NMR (176 MHz, CDCl$_3$) δ 101.2 (162 Hz, β-glucoside), 100.6 (162 Hz, β-glucoside), 100.2 (175 Hz, α-mannoside), 99.4 (173 Hz, α-mannoside), 97.6 (169 Hz, α-glucoside), 97.5 (175 Hz, α-mannoside). ESI-HRMS m/z: Calcd. for $C_{145}H_{162}O_{36}N$ $[M+NH_4]^+$: 2493.0877; found: 2493.0816.

Methyl-4-O-(2-O-acetyl-3,4,6-tri-O-benzyl-α-D-mannopyranosyl)-2-O-benzyl-4,6-O-benzylidene-α-D-glucopyranoside

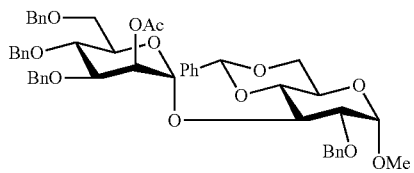

By following the general experimental procedure 2-O-acetyl-3,4,6-tri-O-benzyl-α-D-mannopyranosyl fluoride (100 mg, 0.20 mmol), methyl-2-O-benzyl-3-O-trimethylsilyl-4,6-O-benzylidene-α-D-glucopyranoside (99 mg, 0.22 mmol), and tris-(pentafluorophenyl) borane (5.2 mg, 0.01 mmol) gave the desired product as a white foam (155 mg, 0.18 mmol, yield was 91%). $^1H$ NMR (700 MHz, CDCl$_3$) δ 7.51-7.46 (m, 2H), 7.41-7.18 (m, 23H), 5.60 (br s, 1H), 5.58 (br s, 1H), 5.46 (br s, 1H), 4.91 (d, J=10.9 Hz, 1H), 4.74 (dd, J=11.7, 3.2 Hz, 2H), 4.70-4.66 (m, 2H), 4.57-4.51 m, 3H), 4.40 (d, J=12.0 Hz, 1H), 4.33-4.28 (m, 2H), 4.21-4.51 (m, 1H), 4.08-4.01 (m, 2H), 3.85 (td, J=10.0, 4.9 Hz, 1H), 3.78-3.69 (m, 2H), 3.68-3.61 (m, 2H), 3.51 (dd, J=9.5, 3.6 Hz, 1H), 3.42 (s, 3H), 2.14 (s, 3H). $^{13}C$ NMR (176 MHz, CDCl$_3$) δ 170.3, 139.0, 138.5, 138.2, 137.5, 137.2, 128.9, 128.6, 128.5, 128.4, 128.2, 128.2, 128.1, 128.1, 128.1, 128.0, 127.7, 127.7, 127.5, 127.4, 126.1, 101.2, 98.7, 98.1, 82.5, 78.0, 75.0, 74.2, 73.6, 73.4, 73.4, 71.6, 71.4, 69.0, 68.6, 68.4, 61.9, 55.3, 21.1. ESI-HRMS m/z: Calcd. for $C_{50}H_{54}O_{12}Na$ $[M+Na]^+$: 869.3499; found: 869.3513.

4-Penten-1-yl-4-O-(2-O-acetyl-3,4,6-tri-O-benzyl-α-D-mannopyranosyl)-2,3,6-tri-O-benzyl-β-D-glucopyranoside

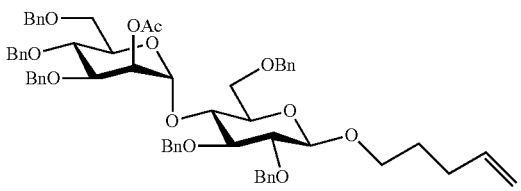

By following the general experimental procedure 2-O-acetyl-3,4,6-tri-O-benzyl-α-D-mannopyranosyl fluoride (100 mg, 0.20 mmol), 4-penten-1-yl-2,3,6-tri-O-benzyl-4-O-trimethylsilyl-α-D-glucopyranoside (131 mg, 0.22 mmol), and tris-(pentafluorophenyl) borane (5.2 mg, 0.01 mmol) gave the desired product as a white foam (166 mg, 0.17 mmol, yield was 83%). $^1H$ NMR (400 MHz, CDCl$_3$) δ 7.32-7.19 (m, 28H), 7.16-7.12 (m, 2H), 5.88-5.75 (m, 1H), 5.46-5.39 (m, 2H), 5.07-4.89 (m, 4H), 4.80 (d, J=10.7 Hz, 1H), 4.71-4.59 (m, 4H), 4.53 (q, J=12.1 Hz, 2H), 4.45-4.36 (m, 4H), 3.95 (dt, J=9.7, 6.4 Hz, 1H), 3.85-3.75 (m, 5H), 3.69-3.62 (m, 2H), 3.61-3.52 (m, 2H), 3.50-3.41 (m, 3H), 2.16 (q, J=7.1 Hz, 2H), 1.96 (s, 3H), 1.75 (p, J=7.2 Hz, 2H). $^{13}C$ NMR (176 MHz, CDCl$_3$) δ 138.5, 138.4, 138.1, 128.4, 128.4, 128.4, 128.3, 128.3, 128.1, 128.1, 128.0, 127.9, 127.7, 127.7, 127.7, 127.6, 127.6, 127.5, 127.4, 127.3, 115.0, 103.6, 99.1, 84.7, 82.3, 78.3, 75.3, 75.2, 74.9, 74.7, 74.5, 74.1, 73.5, 73.5, 72.5, 71.8, 69.6, 69.4, 68.8, 68.7, 30.3, 29.1, 21.0. ESI-HRMS m/z: Calcd. for $C_{61}H_{72}O_{12}N$ $[M NH_4]^+$: 1010.5049; found: 1010.5061.

Methyl-4-O-(2-O-acetyl-3,4,6-tri-O-benzyl-α-D-mannopyranosyl)-2,3-di-O-benzyl-6-O-triisopropyl-silyl-α-D-glucopyranoside

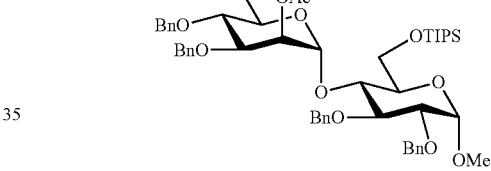

By following the general experimental procedure 2-O-acetyl-3,4,6-tri-O-benzyl-α-D-mannopyranosyl fluoride (100 mg, 0.20 mmol), methyl-2,3-di-O-benzyl-4-O-trimethylsilyl-6-O-triisopropylsilyl-α-D-glucopyranoside (134 mg, 0.22 mmol), and tris-(pentafluorophenyl) borane (5.2 mg, 0.01 mmol) gave the desired product as a white foam (180 mg, 0.18 mmol, yield was 89%). $^1H$ NMR (700 MHz, CDCl$_3$) δ 7.36-7.23 (m, 23H), 7.18-7.15 (m, 2H), 5.50 (br s, 2H), 5.07 (d, J=11.1 Hz, 1H), 4.86 (d, J=11.0 Hz, 1H), 4.75 (d, J=11.1 Hz, 1H), 4.72 (d, J=12.1 Hz, 1H), 4.69 (d, J=12.2 Hz, 1H), 4.67 (d, J=11.0 Hz, 1H), 4.61 (d, J=12.0 Hz, 1H), 4.59 (d, J=3.5 Hz, 1H), 4.49 (d, J=10.6 Hz, 1H), 4.48 (d, J=11.8 Hz, 1H), 4.44 (d, J=11.0 Hz, 1H), 3.99-3.95 (m, 2H), 3.93-3.87 (m, 2H), 3.87-3.82 (m, 1H), 3.82-3.77 (m, 2H), 3.70-3.63 (m, 3H), 3.52 (dd, J=9.8, 3.5 Hz, 1H), 3.41 (s, 3H), 1.99 (s, 3H), 1.10-1.15 (m, 3H), 1.04 (d, J=6.6 Hz, 18H). $^{13}C$ NMR (176 MHz, CDCl$_3$) δ 169.9, 138.7, 138.6, 138.3, 138.0, 138.0, 128.4, 128.3, 128.3, 128.2, 128.2, 128.0, 127.9, 127.8, 127.6, 127.5, 127.5, 127.3, 127.3, 127.3, 98.8, 97.3, 81.9, 80.2, 78.3, 75.1, 75.0, 74.8, 73.9, 73.6, 73.2, 72.7, 71.8, 71.4, 68.8, 68.7, 63.5, 54.9, 20.95, 18.0, 12.0. ESI-HRMS m/z: Calcd. for $C_{59}H_{80}O_{12}NSi$ $[M+NH_4]^+$: 1022.5450; found: 1022.5442.

Methyl-4-O-(2-O-acetyl-3,4,6-tri-O-benzyl-α-D-mannopyranosyl)-2,3-di-O-benzyl-6-O-tert-butyldimethylsilyl-α-D-glucopyranoside

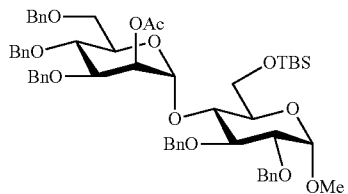

By following the general experimental procedure 2-O-acetyl-3,4,6-tri-O-benzyl-α-D-mannopyranosyl fluoride (100 mg, 0.20 mmol), methyl-2,3-di-O-benzyl-4-O-trimethylsilyl-6-O-tert-butyldimethylsilyl-α-D-glucopyranoside (124 mg, 0.22 mmol), and tris-(pentafluorophenyl) borane (5.2 mg, 0.01 mmol) gave the desired product as a white foam (156 mg, 0.16 mmol, yield was 80%). $^1$H NMR (700 MHz, CDCl$_3$) δ 7.44-7.23 (m, 23H), 7.21-7.17 (m, 2H), 5.52 (br s, 1H), 5.48 (br s, 1H), 5.08 (d, J=11.1 Hz, 1H), 4.87 (d, J=10.9 Hz, 1H), 4.77 (d, J=11.1 Hz, 1H), 4.73 (d, J=12.1, 1H), 4.72 (d, J=12.1, 1H), 4.68 (d, J=11.1 Hz, 1H), 4.63 (d, J=12.0 Hz, 1H), 4.60 (d, J=3.5 Hz, 1H), 4.54-4.49 (m, 2H), 4.46 (d, J=11.0 Hz, 1H), 3.98 (t, J=9.1 Hz, 1H), 3.95-3.86 (m, 4H), 3.84 (dd, J=10.6, 3.5 Hz, 1H), 3.79 (dd, J=11.4, 5.5 Hz, 1H), 3.75-3.70 (m, 2H), 3.63-3.58 (m, 1H), 3.53 (dd, J=9.6, 3.4 Hz, 1H), 3.41 (s, 3H), 2.02 (s, 3H), 0.91 (s, 9H), 0.06 (s, 3H), 0.06 (s, 3H). $^{13}$C NMR (176 MHz, CDCl$_3$) δ 169.9, 138.7, 138.6, 138.3, 138.0, 138.0, 128.4, 128.3, 128.3, 128.2, 128.2, 128.0, 127.9, 127.8, 127.6, 127.5, 127.5, 127.3, 127.3, 127.3, 98.8, 97.3, 81.9, 80.2, 78.3, 75.1, 75.0, 74.8, 73.9, 73.6, 73.2, 72.7, 71.8, 71.4, 68.8, 68.7, 63.5, 54.9, 20.9, 18.0, 12.0, 11.9. ESI-HRMS m/z: Calcd. for C$_{56}$H$_{70}$O$_{12}$NaSi [M+Na]$^+$: 985.4513; found: 985.4522.

Methyl-4-O-(2,3,4,6-tetra-O-acetyl-α-D-mannopyranosyl)-2,3,6-tri-O-benzyl-α-D-galactopyranoside

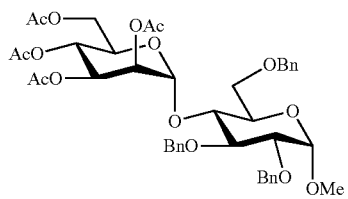

By following the general experimental procedure 2-O-acetyl-3,4,6-tri-O-benzyl-α-D-mannopyranosyl fluoride (100 mg, 0.20 mmol), methyl-2,3,6-tri-O-benzyl-4-O-trimethylsilyl-α-D-galactopyranoside (119 mg, 0.22 mmol), and tris-(pentafluorophenyl) borane (5.2 mg, 0.01 mmol) gave the desired product as a white foam (142 mg, 0.15 mmol, yield was 75%). $^1$H NMR (700 MHz, CDCl$_3$) δ 7.46-7.05 (m, 30H), 5.43 (d, J=3.3 Hz, 1H), 5.03 (s, 1H), 4.90-4.84 (m, 2H), 4.82 (d, J=11.9 Hz, 1H), 4.77-4.74 (m, 2H), 4.71 (d, J=11.4 Hz, 2H), 4.68-4.58 (m, 5H), 4.51-4.43 (m, 2H), 4.28-4.19 (m, 3H), 4.09 (t, J=9.7 Hz, 1H), 3.97 (dd, J=9.7, 3.2 Hz, 1H), 3.92-3.84 (m, 3H), 3.67-3.55 (m, 2H), 3.51 (dd, J=11.1, 2.3 Hz, 1H), 3.39 (s, 3H), 3.14 (d, J=10.8 Hz, 1H), 2.16 (s, 3H). $^{13}$C NMR (176 MHz, CDCl$_3$) δ 170.7, 138.8, 138.8, 138.3, 138.2, 138.2, 137.8, 128.5, 128.5, 128.4, 128.4, 128.3, 128.3, 128.1, 127.9, 127.9, 127.8, 127.8, 127.6, 127.6, 127.4, 127.4, 99.3, 98.9, 78.2, 77.0, 75.8, 75.1, 75.1, 74.1, 73.4, 73.4, 73.4, 72.7, 72.1, 71.6, 69.3, 68.7, 67.9, 67.9, 55.5, 21.3. ESI-HRMS m/z: Calcd. for C$_{57}$H$_{62}$O$_{12}$Na [M+Na]$^+$: 961.4133; found: 961.4134.

Methyl-4-O-(2-O-acetyl-3,4,6-tri-O-benzyl-β-D-glucopyranosyl)-2,3,6-tri-O-benzyl-α-D-glucopyranoside

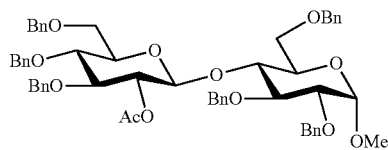

By following the general experimental procedure 2-O-acetyl-3,4,6-tri-O-benzyl-β-D-glucopyranosyl fluoride (100 mg, 0.20 mmol), methyl-2,3,6-tri-O-benzyl-4-O-trimethylsilyl-α-D-glucopyranoside (119 mg, 0.22 mmol), and tris-(pentafluorophenyl) borane (5.2 mg, 0.01 mmol) gave the desired product as a white foam (155 mg, 0.165 mmol, yield was 82%). Methyl-4-O-(2-O-acetyl-3,4,6-tri-O-benzyl-β-D-glucopyranosyl)-2,3,6-tri-O-benzyl-α-D-glucopyranoside was characterized according to Micheli, E.; Nicotra, F.; Panza, L.; Ronchetti, F.; Toma, L. Carbohydr. Res. 1985, 139, C1-C3, Padungros, P.; Alberch, L.; Wei, A. J. Org. Chem. 2014, 79, 2611-2624, Shu, P.; Xiao, X.; Zhao, Y.; Xu, Y.; Yao, W.; Tao, J.; Wang, H.; Yao, G.; Lu, Z.; Zeng, J. Angew. Chem., Int. Ed. Engl. 2015, 54, 14432-14436, and Du, S.; Ragains, J. R. Org. Lett. 2019, 21, 980-983.

Methyl-4-O-(2-O-acetyl-3,4,6-tri-O-benzyl-β-D-glucopyranosyl)-2,3,6-tri-O-benzyl-α-D-galactopyranoside

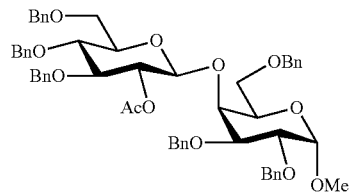

By following the general experimental procedure 2-O-acetyl-3,4,6-tri-O-benzyl-β-D-glucopyranosyl fluoride (100 mg, 0.20 mmol), methyl-2,3,6-tri-O-benzyl-4-O-trimethylsilyl-α-D-galactopyranoside (119 mg, 0.22 mmol), and tris-(pentafluorophenyl) borane (5.2 mg, 0.01 mmol) gave the desired product as a white foam (162 mg, 0.17 mmol, yield was 85%). Methyl-4-O-(2-O-acetyl-3,4,6-tri-O-benzyl-β-D-glucopyranosyl)-2,3,6-tri-O-benzyl-α-D-galactopyranoside was characterized according to Shu, P.; Xiao, X.; Zhao, Y.; Xu, Y.; Yao, W.; Tao, J.; Wang, H.; Yao, G.; Lu, Z.; Zeng, J. Angew. Chem., Int. Ed. Engl. 2015, 54, 14432-14436, Xiao, X.; Zhao, Y.; Shu, P.; Zhao, X.; Liu, Y.; Sun, J.; Zhang, Q.; Zeng, J.; Wan, Q. J. Am. Chem. Soc. 2016, 138, 13402-13407, and Du, S.; Ragains, J. R. Org. Lett. 2019, 21, 980-983.

Methyl-4-O-(2,3,4,6-tetra-O-acetyl-β-D-glucopyranosyl)-2,3,6-tri-O-benzyl-α-D-glucopyranoside

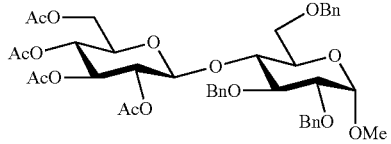

By following the general experimental procedure 2,3,4,6-tetra-O-acetyl-β-D-glucopyranosyl fluoride (70 mg, 0.20 mmol), methyl-2,3,6-tri-O-benzyl-4-O-trimethylsilyl-α-D-glucopyranoside (119 mg, 0.22 mmol), and tris-(pentafluorophenyl) borane (5.2 mg, 0.01 mmol) gave the desired product as a white foam (100 mg, 0.13 mmol, yield was 62%). Methyl-4-O-(2,3,4,6-tetra-O-acetyl-β-D-glucopyranosyl)-2,3,6-tri-O-benzyl-α-D-glucopyranoside was characterized according to Konradsson, P.; Mootoo, D. R.; McDevitt, R. E.; Fraser-Reid, B. *J. Chem. Soc., Chem. Commun.* 1990, 3, 270-272, Mukhopadhyay, B.; Maurer, S. V.; Rudolph, N.; Van Well, R. M.; Russell, D. A.; Field, R. A. *J. Org. Chem.* 2005, 70, 9059-9062, Xiao, X.; Zhao, Y.; Shu, P.; Zhao, X.; Liu, Y.; Sun, J.; Zhang, Q.; Zeng, J.; Wan, Q. *J. Am. Chem. Soc.* 2016, 138, 13402-13407, and Du, S.; Ragains, J. R. *Org. Lett.* 2019, 21, 980-983.

Methyl-4-O-(2,3,4-tri-O-acetyl-α-L-rhamnopyranosyl)-2,3,6-tri-O-benzyl-α-D-galactopyranoside

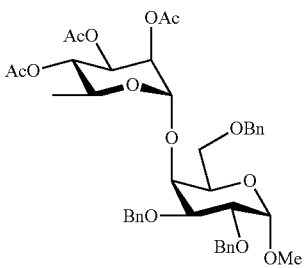

By following the general experimental procedure 2,3,4-Tri-O-acetyl-α-D-rhamnopyranosyl fluoride (100 mg, 0.34 mmol), methyl-2,3,6-tri-O-benzyl-4-O-trimethylsilyl-α-D-galactopyranoside (202 mg, 0.38 mmol), and tris-(pentafluorophenyl) borane (8.8 mg, 0.017 mmol) gave the desired product as a white foam (176 mg, 0.24 mmol, yield was 70%). $^1$H NMR (500 MHz, CDCl$_3$) δ 7.49-7.38 (m, 2H), 7.36-7.18 (m, 13H), 5.50 (s, 1H), 5.32 (dd, J=10.2, 3.2 Hz, 1H), 5.16 (s, 1H), 5.03 (t, J=9.9 Hz, 1H), 4.90-4.76 (m, 2H), 4.73-4.64 (m, 2H), 4.64-4.60 (m, 1H), 4.55 (s, 2H), 4.12 (d, J=2.7 Hz, 1H), 4.03-3.84 (m, 4H), 3.70-3.53 (m, 2H), 3.37 (s, 3H), 2.04 (s, 3H), 2.02 (s, 3H), 1.99 (s, 3H), 1.13 (d, J=6.2 Hz, 3H). $^{13}$C NMR (126 MHz, CDCl$_3$) δ 170.0, 169.9, 169.6, 138.5, 138.4, 138.0, 128.5, 128.5, 128.4, 127.8, 127.7, 127.5, 99.2, 99.0, 78.3, 76.5, 75.5, 74.1, 73.6, 71.1, 69.8, 69.3, 69.3, 68.8, 67.1, 55.5, 21.0, 20.9, 20.9, 17.5. ESI-HRMS m/z: Calcd. for C$_{40}$H$_{48}$O$_{13}$Na [M+Na]$^+$: 759.2987; found: 759.2985.

Methyl-3-O-(2-O-acetyl-3-O-benzyl-4-O-tributylsilyl-6-O-triisopropylsilyl-α-D-mannopyranosyl)-2,4,6-tri-O-benzyl-α-D-glucopyranoside

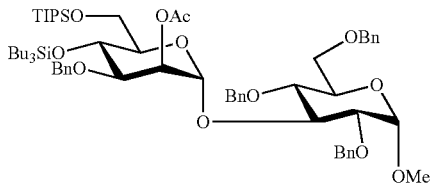

By following the general experimental procedure 2-O-acetyl-3-O-benzyl-4-O-tributylsilyl-6-O-triisopropylsilyl-α-D-mannopyranosyl fluoride (100 mg, 0.15 mmol), methyl-2,4,6-tri-O-benzyl-3-O-trimethylsilyl-α-D-galactopyranoside (89 mg, 0.16 mmol), and tris-(pentafluorophenyl) borane (3.8 mg, 0.007 mmol) gave the desired product as a white foam (150 mg, 0.13 mmol, yield was 90%). $^1$H NMR (400 MHz, CDCl$_3$) δ 7.38-7.17 (m, 18H), 7.14-7.07 (m, 2H), 5.42 (br s, 1H), 5.28 (br s, 1H), 4.69 (d, J=11.9 Hz, 1H), 4.68 (d, J=11.3 Hz, 1H), 4.67 (d, J=11.1 Hz, 1H), 4.62-4.55 (m, 2H), 4.53-4.39 (m, 3H), 4.30 (d, J=11.1 Hz, 1H), 4.17 (t, J=9.3 Hz, 1H), 4.13 (t, J=9.2 Hz, 1H), 3.88 (d, J=9.4 Hz, 1H), 3.84-3.75 (m, 2H), 3.75-3.66 (m, 3H), 3.66-3.56 (m, 2H), 3.38 (dd, J=9.6, 3.7 Hz, 1H), 3.32 (s, 3H), 1.90 (s, 3H), 1.27-1.13 (m, 12H), 1.12-1.00 (m, 3H), 1.04 (d, J=4.2 Hz, 18H), 0.84-0.73 (t, J=6.8 Hz, 9H), 0.64-0.44 (m, 6H). ESI-HRMS m/z: Calcd. for C$_{60}$H$_{100}$O$_{12}$NSi$_2$[M+NH$_4$]$^+$: 1130.6784; found: 1130.6778.

Methyl-4-O-(2,3,4,6-tetra-O-acetyl-α-D-mannopyranosyl)-6-O-(2-O-acetyl-3,4,6-tri-O-benzyl-β-D-glucopyranosyl)-2,3-di-O-benzyl-α-D-glucopyranoside

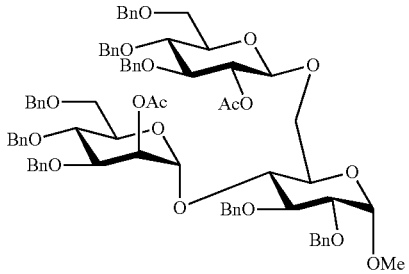

To a stirred solution of 2-O-acetyl-3,4,6-tri-O-benzyl-α-D-mannopyranosyl fluoride (50 mg, 0.10 mmol) and methyl-2,3,-di-O-benzyl-4-O-trimethylsilyl-6-O-tert-butyldimethylsilyl-α-D-glucopyranoside (119 mg, 0.22 mmol) in dry toluene (2.0 mL) was added a solution of tris-(pentafluorophenyl) borane (2.6 mg, 0.005 mmol) in dry toluene (0.5 mL) at RT. After stirring for 0.5 h at RT to the reaction mixture was added a solution of 2-O-acetyl-3,4,6-tri-O-benzyl-β-D-glucopyranosyl fluoride (50 mg, 0.10 mmol) in dry toluene (0.5 mL) and stirring was continued for additional 1 h at RT. Then the reaction mixture was concentrated under reduced pressure and the residue was subjected to column chromatography on silica gel using ethyl acetate/hexane solvent system to give the desired product as a white foam (82 mg, 0.061 mmol, yield was 61%). $^1$H NMR (700 MHz, CDCl$_3$) δ 7.39-7.24 (m, 36H), 7.23-7.14 (m, 4H), 5.48 (br s, 1H), 5.31 (br s, 1H), 5.07-5.02 (m, 2H), 4.86 (d, J=10.8 Hz, 1H), 4.82-7.14 (m, 3H), 4.71 (d, J=12.1 Hz, 1H), 4.68 (d, J=11.4 Hz, 1H), 4.66 (d, J=12.2 Hz, 1H), 4.63 (d, J=11.0 Hz, 1H), 4.60-4.54 (m, 4H), 4.49 (t, J=10.8 Hz, 2H), 4.46-4.41 (m, 3H), 4.12 (dd, J=10.8, 1.8 Hz, 1H), 3.96-3.88 (m, 3H), 3.84 (t, J=9.5 Hz, 1H), 3.80 (dd, J=10.7, 4.3 Hz, 1H), 3.77-3.70 (m, 4H), 3.65 (dt, J=14.2, 4.1 Hz, 4H), 3.53 (dd, J=9.6, 3.5 Hz, 1H), 3.40 (dd, J=8.1, 4.7 Hz, 1H), 3.38 (s, 3H), 2.02 (s, 3H), 1.97 (s, 3H). $^{13}$C NMR (176 MHz, CDCl$_3$) δ 169.7, 169.4, 138.6, 138.4, 138.3, 138.3, 138.2, 138.1, 138.0, 137.9, 128.5, 128.4, 128.4, 128.4, 128.5, 128.3, 128.3, 128.2, 128.2, 128.1, 128.0, 128.0, 127.9, 127.8, 127.7, 127.7, 127.7, 127.6, 127.6, 127.5, 127.3, 127.2, 101.2, 100.0, 97.5, 83.0, 81.4, 80.0, 78.1, 77.9, 77.5, 75.2, 75.2, 75.1, 75.0, 74.9, 74.1, 73.4, 73.4, 73.2, 73.1, 72.5, 71.8, 69.5, 69.1, 68.9, 68.7, 68.5, 55.2, 21.0. ESI-HRMS m/z: Calcd. for C$_{79}$H$_{90}$O$_{18}$N [M+NH$_4$]$^+$: 1340.6158; found: 1340.6121.

Methyl-3-O-[2-O-acetyl-3-O-benzyl-4-O-(2-O-acetyl-3,4,6-tri-O-benzyl-α-D-mannopyranosyl)-6-O-triisopropylsilyl-α-D-mannopyranosyl]-2,4,6-tri-O-benzyl-α-D-glucopyranoside

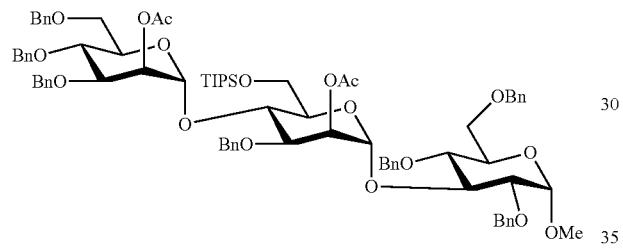

To a stirred solution of 2-O-acetyl-3-O-benzyl-4-O-tributylsilyl-6-O-triisopropylsilyl-α-D-mannopyranosyl fluoride (100 mg, 0.15 mmol), methyl-2,4,6-tri-O-benzyl-3-O-trimethylsilyl-α-D-glucopyranoside (81 mg, 0.15 mmol), in dry toluene (2.5 mL) was added a solution of tris-(pentafluorophenyl) borane (3.8 mg, 0.007 mmol) in dry toluene (0.5 mL) at RT. After stirring for 0.5 h at RT to the reaction mixture was added a solution of 2-O-acetyl-3,4,6-tri-O-benzyl-α-D-mannopyranosyl fluoride (75 mg, 0.15 mmol) in dry toluene (0.5 mL) and stirring was continued for additional 1 h at RT. ESI-HRMS m/z: Calcd. for C$_{81}$H$_{104}$O$_{18}$NSi [M NH$_4$]$^+$: 1406.7023; found: 1406.6679, indicated formation of the desired product.

Methyl-6-O-(3,4,6-tri-O-benzyl-β-D-mannopyranosyl)-2,3,4-tri-O-benzyl-α-D-glucopyranoside

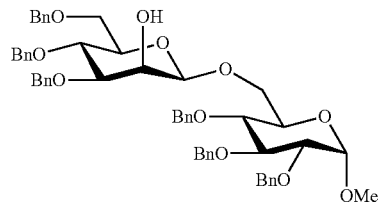

To a stirred solution of 2-O-(Methyl-2,3,4-tri-O-benzyl-6-O-dimethylsilyl-α-D-glucopyranosyl)-3,4,6-tri-O-benzyl-α-D-mannopyranosyl fluoride (130 mg, 0.13 mmol) in dry toluene (6 mL) was added a solution of tris-(pentafluorophenyl) borane (3.6 mg, 0.007 mmol) in dry toluene (0.5 mL) at RT. After stirring for 1 h at RT to the reaction mixture was added a 1 M solution of tetrabutylammonium fluoride in tetrahydrofuran (0.4 mL, 0.4 mmol) and stirring was continued overnight at RT. Then reaction mixture was diluted with ethyl acetate (30 mL), washed with aq-NaHCO$_3$ (30 mL) and brine (30 mL), dried over Na$_2$SO$_4$, and concentrated under reduced pressure. The residue was subjected to column chromatography on silica gel using ethyl acetate/hexane solvent system to give the desired product as a white foam (100 mg, 0.12 mmol, yield was 83%). Methyl-6-O-(3,4,6-tri-O-benzyl-β-D-mannopyranosyl)-2,3,4-tri-O-benzyl-α-D-glucopyranoside as characterized according to Barresi, F.; Hindsgaul, O. *J. Am. Chem. Soc.* 1991, 113, 9376-9377, Stork, G.; Kim, G. *J. Am. Chem. Soc.* 1992, 114, 1087-1088, Stork, G.; La Clair, J. J. *J. Am. Chem. Soc.* 1996, 118, 247-248, Aloui, M.; Chambers, D. J.; Cumpstey, I.; Fairbanks, A. J.; Redgrave, A J.; Seward, C. M. P. *Chem.: Eur. J.* 2002, 8, 2608-2621, Chayajarus, K.; Chambers, D. J.; Chughtai, M. J.; Fairbanks, A. J. *Org. Lett.* 2004, 6, 3797-3800.

Methyl-6-O-(3,4,6-tri-O-benzyl-α-D-glucopyranosyl)-2,3,4-tri-O-benzyl-α-D-glucopyranoside

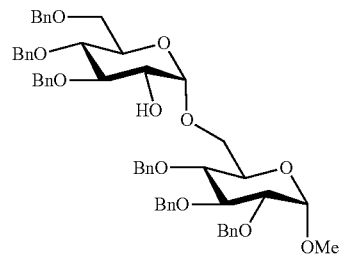

To a stirred solution of 2-O-(Methyl-2,3,4-tri-O-benzyl-6-O-dimethylsilyl-α-D-glucopyranosyl)-3,4,6-tri-O-benzyl-β-D-glucopyranosyl fluoride (115 mg, 0.12 mmol) in dry toluene (5.5 mL) was added a solution of tris-(pentafluorophenyl) borane (3.1 mg, 0.006 mmol) in dry toluene (0.5 mL) at RT. After stirring for 1 h at RT to the reaction mixture was added a 1 M solution of tetrabutylammonium fluoride in tetrahydrofuran (0.35 mL, 0.35 mmol) and stirring was continued overnight at RT. Then reaction mixture was diluted with ethyl acetate (30 mL), washed with aq-NaHCO$_3$ (30 mL) and brine (30 mL), dried over Na$_2$SO$_4$, and concentrated under reduced pressure. The residue was subjected to column chromatography on silica gel using ethyl acetate/hexane solvent system to give the desired product as a white foam (90 mg, 0.10 mmol, yield was 85%). Methyl-6-O-(3,4,6-tri-O-benzyl-α-D-glucopyranosyl)-2,3,4-tri-O-benzyl-α-D-glucopyranoside was characterized according to Aloui, M.; Chambers, D. J.; Cumpstey, I.; Fairbanks, A. J.; Redgrave, A J.; Seward, C. M. P. *Chem.: Eur. J.* 2002, 8, 2608-2621, Chayajarus, K.; Chambers, D. J.; Chughtai, M. J.; Fairbanks, A. J. *Org. Lett.* 2004, 6, 3797-3800, Singh, G. P.; Watson, A. J. A.; Fairbanks, A. J. *Org. Lett.* 2015, 17, 4376-4379, Izumi, Sanae; Kobayashi, Yusuke; Takemoto, Yoshiji *Org. Lett.* 2019, 21, 665-670.

Example 3: Catalyst Loading Screening

TABLE 1

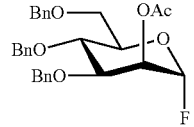

| Catalyst loading (mol %) | Isolated yield |
|---|---|
| 5 | 84%[a] |
| 1 | 91%[a] |
| 0.5 | 89%[a] |

[a]Reactions were conducted by following the general experimental procedure (C) but the substrates were co-evaporated with toluene three times then dried under high vacuum overnight.

TABLE 2

Comparison of various glycosylation conditions

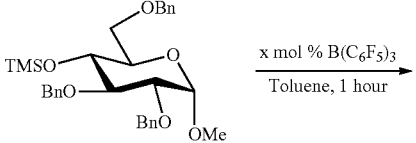

| Conditions | Isolated yield |
|---|---|
| General Procedure C | 84% |
| General Procedure D | 79% |
| General Procedure D on 2.02 mmol scale | 87% |
| General Procedure D with undried ACS-grade dichloromethane, open to ambient conditions | 77% |
| General Procedure C with catalyst stored on the benchtop for 24 h prior to use, Sigma Aldrich Sure/Seal™ Toluene, and the reaction run open to ambient conditions | 90% |

TABLE 3

Control experiments

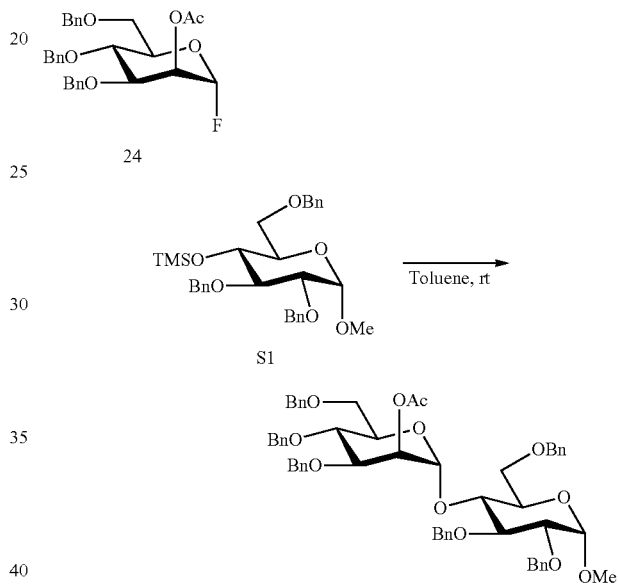

| Conditions | Isolated yield |
|---|---|
| No catalyst | 0%, no conversion |
| 5 mol % HCl in Et$_2$O | 0%, no conversion |

TABLE 4

Effects of hindered base

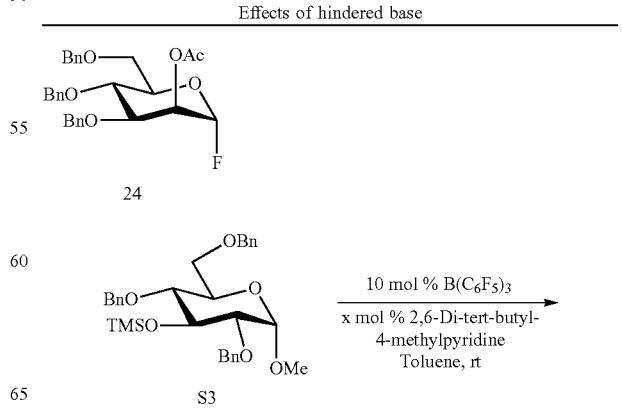

TABLE 4-continued

[Structure: Disaccharide with BnO, OAc, OBn, OMe groups, labeled 2]

| Conditions | Isolated yield |
| --- | --- |
| 10 mol % 2,6-Di-tert-butyl-4-methylpyridine | 87% |
| 20 mol % 2,6-Di-tert-butyl-4-methylpyridine | 71% |

TABLE 5

Comparison between silyl ether acceptor and free alcohol acceptor.

[Reaction scheme: Glycosyl fluoride with TMSO/BnO/OAc/OMe groups + OBn-substituted sugar acceptor → disaccharide product, using 10 mol % B(C$_6$F$_5$)$_3$, x mol % 2,6-Di-tert-butyl-4-methylpyridine, Toluene, rt]

| R = | Isolated yield | Time till complete conversion |
| --- | --- | --- |
| —TMS | 83% | >1 h |
| —H | 74% | 3 h |

Example 4—Catalyst Comparison

Figure 3:
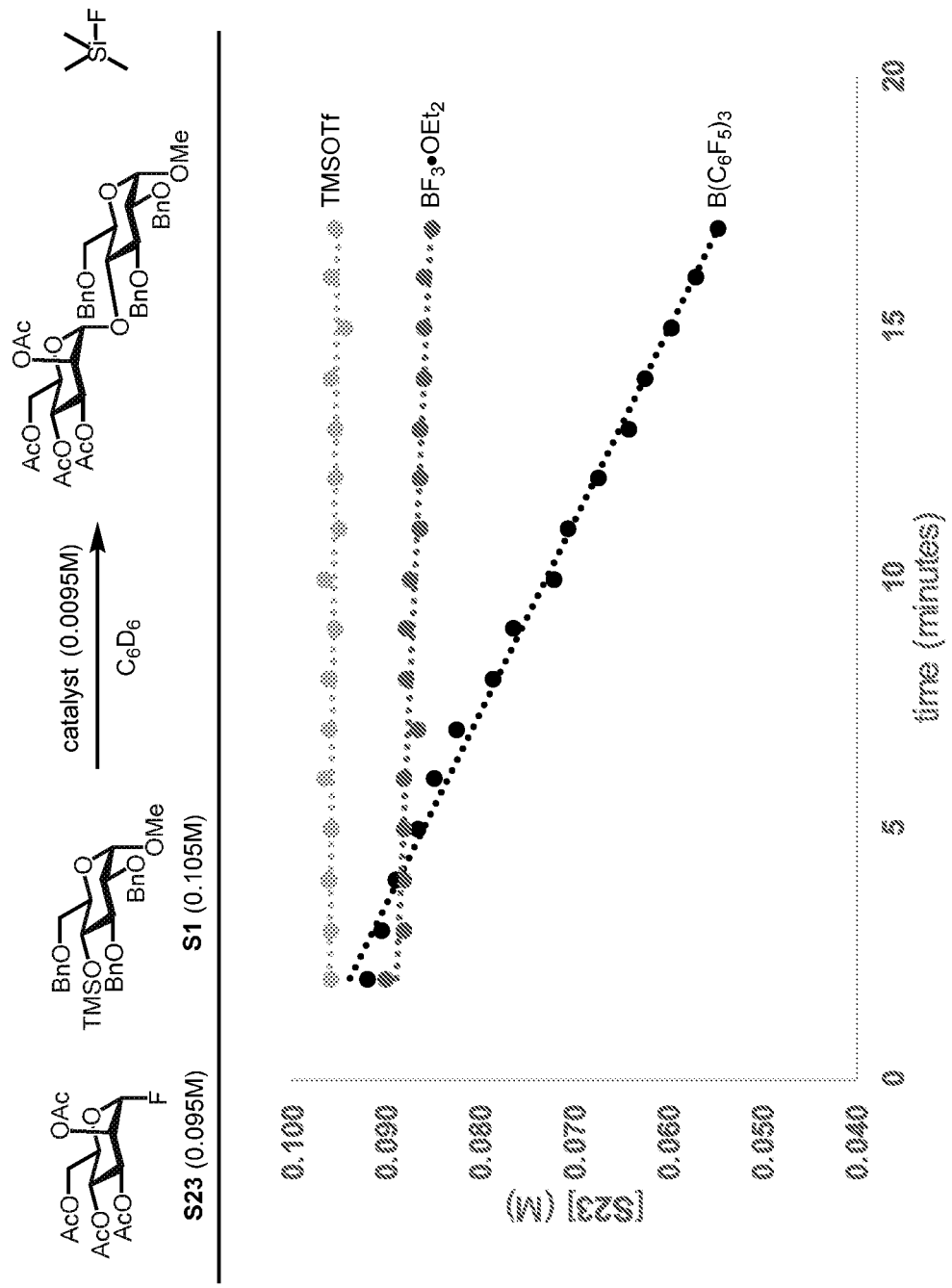
FIG. 3 depicts a graph of a comparison of the reaction progressions using various Lewis acids over time by measuring the disappearance of the $^{19}F$ NMR signal arising from the glycosyl fluoride compared to the internal standard, α,α,α-trifluorotoluene.

Reaction progression on a disarmed glycosyl fluoride: General procedure—$^{19}$F reaction progressions of experiments catalyzed by TMS-OTf, BF$_3$·OEt$_2$ and B(C$_6$F$_5$)$_3$ were followed using the general procedure as seen in FIG. 3. The reactions were performed in duplicate, and the concentration at a given time point averaged.

What is claimed:

1. A method comprising admixing at least one fluoroglycoside of formula (I) and a silyl ether glycoside, in the presence of a catalyst having a formula B (Ar$^1$)(Ar$^2$)(Ar$^3$) under conditions sufficient to form a glycoside product:

[Structure of Formula (I): pyranose ring with R$^6$, R$^4$, R$^3$, R$^2$, F substituents, and m]

wherein each of R$^2$, R$^3$, R$^4$, and R$^6$ is independently H, C$_{1-6}$ alkyl, —N(R$^1$)$_2$, —N$_3$, CO$_2$H, CO$_2$C$_{1-6}$alkyl, or —OR$^{PG}$, or two of R$^2$, R$^3$, R$^4$, and R$^6$, together with the atoms to which they are attached form a five to eight membered heterocycloalkyl having 1 to 3 ring heteroatoms selected from O, N, and S;

each of Ar$^1$, Ar$^2$, Ar$^3$ is independently a halophenyl;

each R$^1$ is independently H, C(O)C$_{1-6}$alkyl, or an amino protecting group;

m is 0 or 1; and each R$^{PG}$ is independently a hydroxyl protecting group or a saccharide.

2. The method of claim 1, wherein at least one R$^2$, R$^3$, R$^4$, and R$^6$ is —OR$^{PG}$ or C$_{1-6}$alkyl.

3. The method of claim 2, wherein at least one R$^{PG}$ is benzyl, acetyl, or methyl, and/or wherein at least one R$^{PG}$ comprises a saccharide, and/or wherein one R$^{PG}$ comprises a connection to a solid support or fluorinated alkyl chain.

4. The method of claim 1, wherein at least one of R$^2$, R$^3$, R$^4$, and R$^6$ is CO$_2$H or CO$_2$C$_{1-6}$alkyl.

5. The method of claim 1, wherein the silyl ether glycoside has a structure of Formula (II):

[Structure of Formula (II): pyranose ring with R$^{6A}$, R$^{4A}$, R$^{3A}$, R$^{2A}$, R$^{1A}$ substituents, and n]

wherein each of R$^{1A}$, R$^{2A}$, R$^{3A}$, R$^{4A}$, and R$^{6A}$ independently is H, an O-silyl ether, OR$^{PG}$, CO$_2$H, CO$_2$C$_{1-6}$alkyl, or C$_{1-6}$alkyl, each R$^{PG}$ is independently a hydroxyl protecting group or a saccharide; and n is 0 or 1;

with the proviso that at least one of R$^{1A}$, R$^{2A}$, R$^{3A}$, R$^{4A}$, and R$^{6A}$ comprises an O-silyl ether.

6. The method of claim 5, wherein if more than one of R$^{1A}$, R$^{2A}$, R$^{3A}$, and R$^{4A}$ comprises an O-silyl ether, then no two O-silyl ethers are identical, or wherein R$^{6A}$ and one of R$^{1A}$, R$^{2A}$, R$^{3A}$, and R$^{4A}$ comprise the same O-silyl ether, or two of R$^{1A}$, R$^{2A}$, R$^{3A}$, R$^{4A}$, and R$^{6A}$ comprise an O-silyl ether.

7. The method of claim 5, wherein one O-silyl ether comprises OTMS, OTBS, or OTIPS.

8. The method of claim 5, wherein one O-silyl ether comprises a di-silyl ether having a structure of

[Structure: —O—Si(—)(—)—O—GLYC]

wherein GLYC is a glycoside moiety.

9. The method of claim 8, wherein GLYC has a structure selected from the group consisting of:

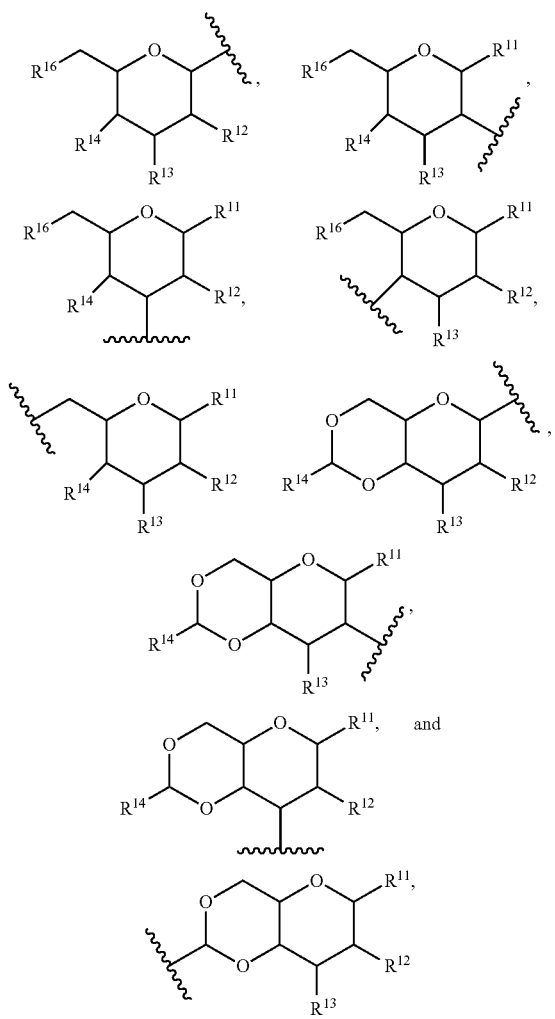

and each of $R^{11}$, $R^{12}$, $R^{13}$, $R^{14}$, $R^{15}$, and $R^{16}$ is independently H, —$OR^{PG}$, $C_{1-6}$ alkyl, $CO_2H$, $CO_2C_{1-6}$alkyl, $Ar^4$, or —$N(R^1)_2$, or two of $R^{11}$, $R^{12}$, $R^{13}$, $R^{14}$, $R^{15}$, and $R^{16}$, together with the atoms to which they are attached form a five to eight member heterocycloalkyl comprising 1 to 3 ring heteroatoms selected from O, N, and S, and each $Ar^4$ is independently selected from $C_6$-$C_{22}$ aryl or a 5-12 membered heteroaryl comprising from 1 to 3 ring heteroatoms selected from O, N, and S.

10. The method of claim 9, wherein at least one of $R^{11}$, $R^{12}$, $R^{13}$, $R^{14}$, $R^{15}$, and $R^{16}$ is —$OR^{PG}$ or $C_{1-6}$ alkyl, or $Ar^4$.

11. The method of claim 10, wherein at least one $R^{PG}$ is benzyl, acetyl, or methyl.

12. The method of claim 10, wherein at least one $Ar^4$ is phenyl.

13. The method of claim 5, wherein at least one of $R^{1A}$, $R^{2A}$, $R^{3A}$, $R^{4A}$, and $R^{6A}$ is $C_{1-6}$alkyl, $CO_2H$ or $CO_2C_{1-6}$alkyl.

14. The method of claim 1, wherein at least one of $Ar^1$, $Ar^2$, and $Ar^3$ is a fluorophenyl or chlorophenyl.

15. The method of claim 1, wherein the catalyst is

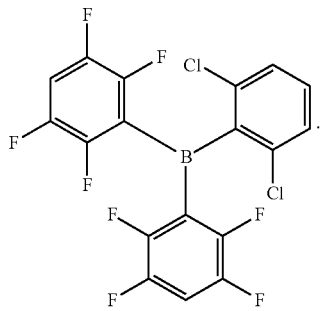 [SMILES: Fc1cc(F)c(F)c(B(c2c(Cl)cccc2Cl)c2c(F)c(F)cc(F)c2F)c1F]

16. The method of claim 1, wherein the catalyst is present in an amount of less than 10 mol %.

17. The method of claim 1, wherein the glycoside product is formed stereoselectively and a single stereoisomer of the glycoside product is formed in 80% yield or more.

18. The method of claim 1, wherein the fluoroglycoside and the silyl ether glycoside are present in a molar ratio of 0.9 to 1 to 1.1 to 1.

19. The method of claim 1, wherein the glycoside product is selected from the group consisting of

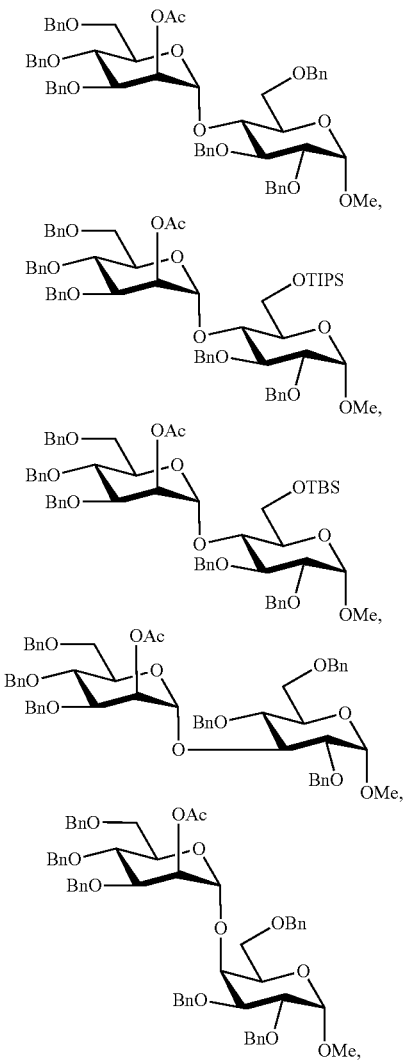

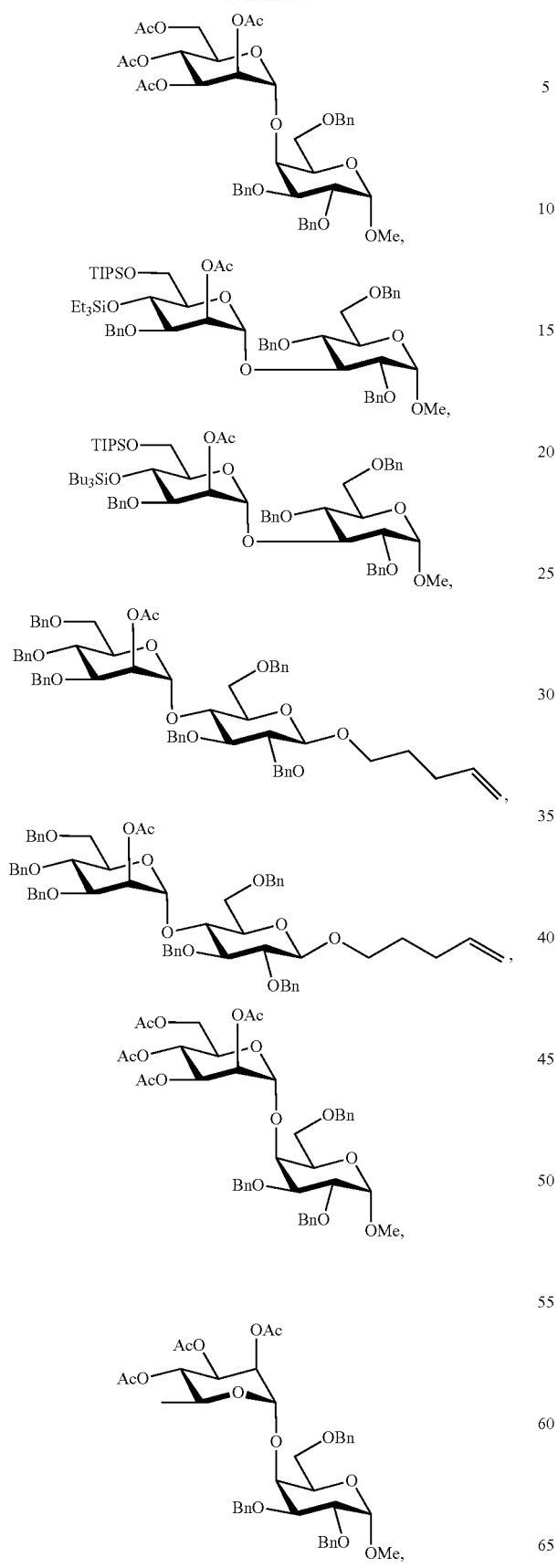
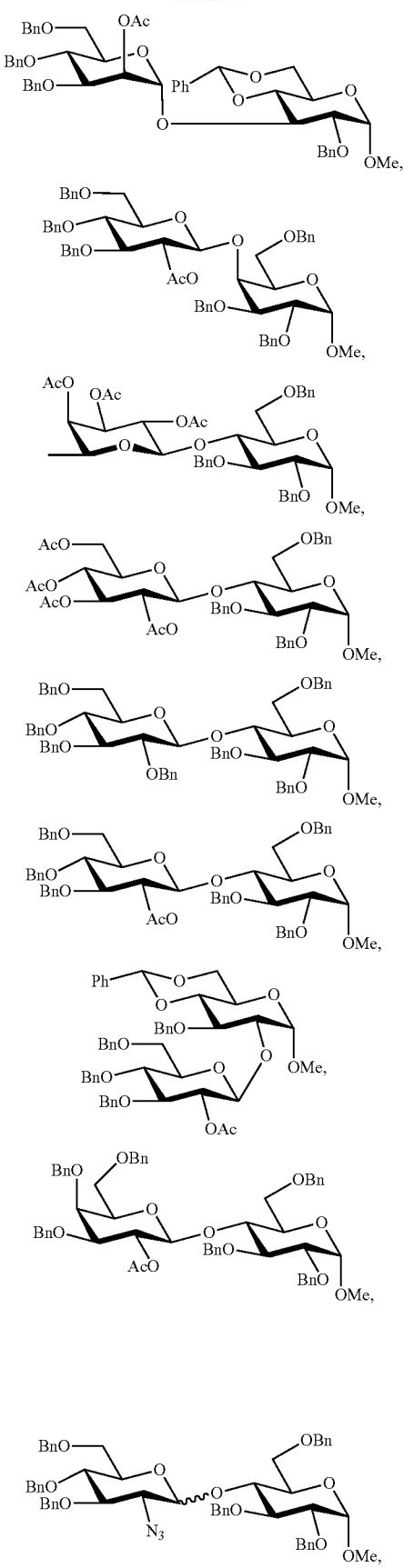

89
-continued

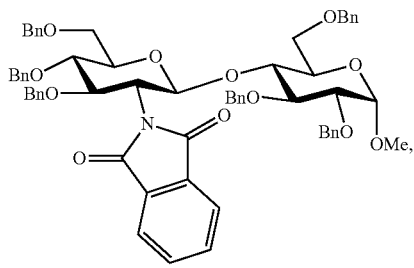

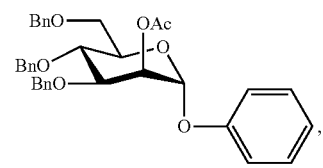

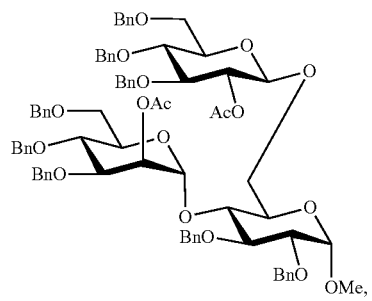

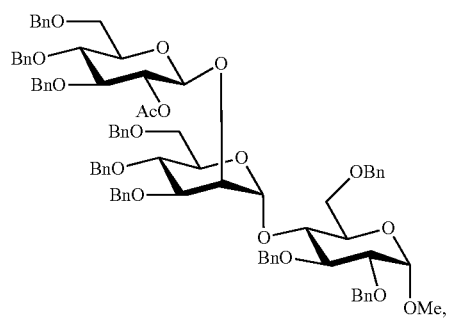

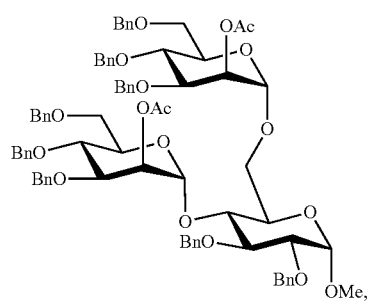

90
-continued

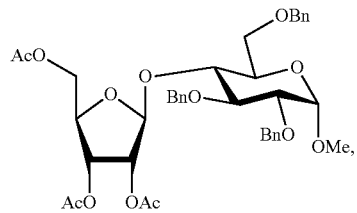

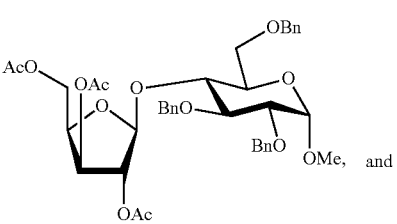

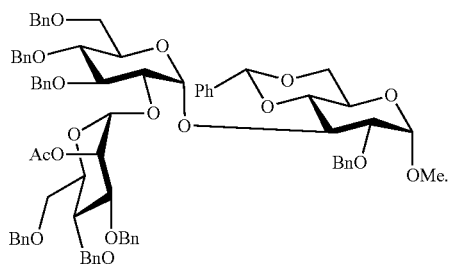

and

20. The method of claim 1, when the glycoside product comprises a second silyl ether, further comprising admixing a second fluoroglycoside with the glycoside product to form a second glycoside product between the second fluoroglycoside and the second silyl ether on the glycoside product.

21. The method of claim 20, wherein the second glycoside product is a trisaccharide or a tetrasaccharide.

22. The method of claim 21, wherein the second glycoside product is

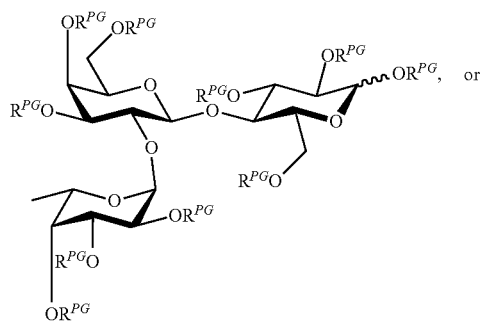

or

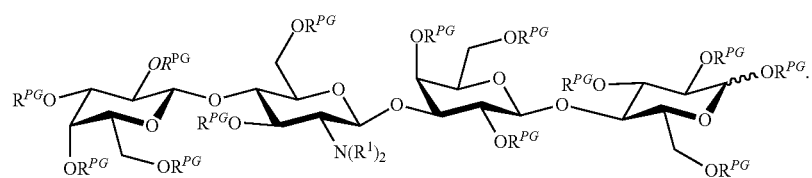
* * * * *